US009868952B2

(12) United States Patent
Lu et al.

(10) Patent No.: US 9,868,952 B2
(45) Date of Patent: Jan. 16, 2018

(54) COMPOSITIONS AND METHODS FOR "RESISTANCE-PROOF" SIRNA THERAPEUTICS FOR INFLUENZA

(71) Applicant: Sirnaomics, Inc., Gaithersburg, MD (US)

(72) Inventors: Patrick Y. Lu, Potomac, MD (US); David M. Evans, North Potomac, MD (US); John J. Xu, Germantown, MD (US); Alan Y. Lu, Baltimore, MD (US); Qing Ge, Gaithersburg, MD (US)

(73) Assignee: Sirnaomics, Inc., Gaithersburg, MD (US)

( * ) Notice: Subject to any disclaimer, the term of this patent is extended or adjusted under 35 U.S.C. 154(b) by 0 days.

(21) Appl. No.: 14/418,432

(22) PCT Filed: Jul. 7, 2013

(86) PCT No.: PCT/US2013/049505

§ 371 (c)(1),
(2) Date: Jan. 29, 2015

(87) PCT Pub. No.: WO2014/011512

PCT Pub. Date: Jan. 16, 2014

(65) Prior Publication Data

US 2016/0068843 A1 Mar. 10, 2016

Related U.S. Application Data

(60) Provisional application No. 61/669,108, filed on Jul. 8, 2012.

(51) Int. Cl.

| | |
|---|---|
| ***C12N 15/11*** | (2006.01) |
| ***C12N 15/113*** | (2010.01) |
| ***A61K 9/00*** | (2006.01) |
| ***A61K 31/713*** | (2006.01) |

(52) U.S. Cl.

CPC .......... *C12N 15/1131* (2013.01); *A61K 9/007* (2013.01); *A61K 31/713* (2013.01); *C12N 2310/14* (2013.01); *C12N 2310/17* (2013.01); *C12N 2320/11* (2013.01); *C12N 2320/31* (2013.01); *C12N 2320/32* (2013.01)

(58) Field of Classification Search

CPC ........................ C12N 15/1131; C12N 2310/14

See application file for complete search history.

(56) References Cited

U.S. PATENT DOCUMENTS

| | | | | |
|---|---|---|---|---|
| 7,070,807 | B2 | 7/2006 | Mixson | |
| 7,163,695 | B2 | 1/2007 | Mixson | |
| 7,199,109 | B2 | 4/2007 | Pal et al. | |
| 7,297,786 | B2 | 11/2007 | McCray et al. | |
| 7,772,201 | B2 | 8/2010 | Mixson | |
| 8,691,781 | B2 | 4/2014 | Tang et al. | |
| 2002/0095692 | A1 | 7/2002 | Thomas et al. | |
| 2005/0008617 | A1* | 1/2005 | Chen | A61K 9/5146 424/93.2 |
| 2006/0025366 | A1 | 2/2006 | MacLachlan et al. | |
| 2006/0134787 | A1 | 6/2006 | Zamore et al. | |
| 2006/0160759 | A1 | 7/2006 | Chen et al. | |
| 2007/0197460 | A1 | 8/2007 | Fougerolles et al. | |
| 2007/0213293 | A1* | 9/2007 | McSwiggen | C12N 15/1131 514/44 A |
| 2008/0287385 | A1 | 11/2008 | Harel-Bellan et al. | |
| 2010/0166661 | A1 | 7/2010 | Zheng et al. | |

FOREIGN PATENT DOCUMENTS

| | | | |
|---|---|---|---|
| WO | WO 01/47496 | A1 | 7/2001 |
| WO | WO 03/040399 | A2 | 5/2003 |
| WO | WO 03/070918 | A2 | 8/2003 |
| WO | WO 03/090719 | A1 | 11/2003 |
| WO | WO 2004/028471 | A2 | 4/2004 |
| WO | WO 2005/076999 | A2 | 8/2005 |
| WO | WO 2006/060182 | A2 | 6/2006 |

OTHER PUBLICATIONS

Barik, Sailen, "Control of nonsegmented negative-strand RNA virus replication by siRNA," Virus Research, vol. 102, 2004, pp. 27-35.
Bitko, Vira, et al, "Phenotypic silencing of cytoplasmic genes using sequence-specific double-stranded short interfering RNA and its application in the reverse genetics of wild type negative-strand RNA viruses" BMC Microbiology, vol. 1, No. 34, Dec. 20, 2001, pp. 1-11.
Bitko, Vira, et al, "Inhibition of respiratory viruses by nasally administered siRNA," Nature Medicine, vol. 11, No. 1, Jan. 2005, pp. 50-55.
Ge, Qing, et al, "RNA interference of influenza virus production by directly targeting mRNA for degradation and indirectly inhibiting all viral RNA transcription," PNAS, vol. 100, No. 5, Mar. 4, 2003, pp. 2718-2723.
Ge, Qing, et al, "Inhibition of influenza virus production in virus-infected mice by RNA interference," PNAS, vol. 101, No. 23, Jun. 8, 2004, pp. 8676-8681.
Ge, Qing, et al, "Use of siRNAs to prevent and treat influenza virus infection," Virus Research, Elsevier, Amsterdam, NL, vol. 102, 2004, pp. 37-42.
De Wolf, Holger, et al., "Effect of Cationic Carriers on the Pharmacokinetics and Tumor Localization of Nucleic Acids after Intravenous Administration," International Journal of Pharmaceutics, 331, 2007, pp. 167-175.
Pickering, Lulu, "Progress in RNA-based therapeutics," Spectrum Drug Discovery and Design, Decision Resources, Inc., Waltham, Massachusetts, Aug. 4, 2005, pp. 6-1 to 6-20.

(Continued)

*Primary Examiner* — Brian Whiteman
(74) *Attorney, Agent, or Firm* — Geoffrey M. Karny

(57) ABSTRACT

The present invention relates to compositions and methods for development of resistance-proof siRNA therapeutics for prevention and treatment of influenza viral infections. The compositions include a pharmaceutical composition comprising siRNA molecules that target conserved regions of an influenza virus gene and a pharmaceutically acceptable polymeric carrier. In one embodiment, the polymeric carrier condenses the molecules to form a nanoparticle.

22 Claims, 34 Drawing Sheets

(56) References Cited

OTHER PUBLICATIONS

Leng, Qixin, et al., "Highly Branched HK Peptides Are Effective Carriers of siRNA," The Journal of Gene Medicine, 2005, 7, pp. 977-986.

Wang, et al., "Co-Delivery of Drugs and DNA from Cationic Core-Shell Nanoparticles Self-Assembled from a Biodegradable Copolymer," Nature Materials 2006, 5:791-796.

International Search Report and Written Opinion of the International Searching Authority, USPTO, on International App. No. PCT/US2013/049505 of Sirnaomics, Inc. for "Compositions and Methods for "Resistant-Proof" SiRNA Therapeutics for Influenza," dated Nov. 23, 2013.

* cited by examiner

A. Flow cytometry analysis of MEF

B. Florescent image of MEF

SEQUENCE LISTING

```
<160> NUMBER OF SEQ ID NOS: 84

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

gagcgaggac ugcagcguag acgcu                                          25


<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
```

-continued

```
guguggaugg caugccacuc ugctg                                          25


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3

uggcaaaugu ugugagaaat t                                              21


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4

ugagaaagau gaugacuaat t                                              21


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5

ugacaugagu auuggaguat t                                              21


<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6

ccugcaaguu agugggaaut t                                              21


<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
```

```
ggauagaacu ugaugaaaut t                                                21


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8

gagaagaucc caaggacaat t                                                21


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9

ggaaggcucu auugggaaat t                                                21


<210> SEQ ID NO 10
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10

acgcugcagu ccucgcucac uggg                                             24


<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11

cccagugagc gaggacugca gcgua                                            25


<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12

gcaauugagg agugccugat t                                                21


<210> SEQ ID NO 13
```

-continued

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 13
ucaggcacuc cucaauugct t 21

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
uacgcugcag uccucgcuca cuggg 25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
ccatcgttcc aagggtacgg cataa 25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
ccatcgttcc aagggtacgt cataa 25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
ccatcgttcc aagggtacgt tccgg 25

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
atacatgcga tcgcatgagt cttctaacc 29

-continued

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
attaatgcga tcgccggaat ggatcccag 29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
attaatgcga tcgcatggac tccaacacc 29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
attaatgcga tcgcttcaat ggtggaaca 29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gcgcgtgcga tcgcatggag agaataaaa 29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
atacatgcga tcgcatgaat ccaaaccaa 29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
atacatgcga tcgcatgaag gcaatacta 29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
agcgccgttt aaacgaggat cacttgaat 29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
agcgccgttt aaactcctca actgtcata 29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
agcgccgttt aaactttcat ttctgctct 29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggcgccgttt aaacagtcat aaagagatt 29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
agcgccgttt aaacattgat ggccatccg 29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
agcgccgttt aaacttactt gtcaatggt 29

<210> SEQ ID NO 31

<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
ggcgccgttt aaacaataca tattctaca 29

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32
gcccagugag cgaggacugc agcgu 25

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
gauucacagc aucggucuca cagac 25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 34
cgaaugggag ugcagaugca gcgau 25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
cagaugcagc gauucaagug auccu 25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
auggcgucuc aaggcaccaa acgau 25

<210> SEQ ID NO 37
<211> LENGTH: 25

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aaugaugcca cauaucagag aacaa 25

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccaaugaucg ucgagcuugc ggaaa 25

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cuugccgacc aaagucuccc accga 25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ccaccgaacu ucuccagccu ugaaa 25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gagagcauga uugaggccga gucuu 25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggcuuuccuu gaagaauccc accca 25

<210> SEQ ID NO 43
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 43

gaugccguug gaauaugaug ccguu                                          25


<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44

ggggaauucu ugaggaugaa cagau                                          25


<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45

gcauggugga ggccauggug ucuag                                          25


<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

gaccaggagt ggaggaaaca                                                20


<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

cggccataat ggtcactctt                                                20


<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

cgtcgcttta aatacggttt g                                              21


<210> SEQ ID NO 49
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 49

cgtcaacatc cacagcattc                                                20


<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

cgtaccactg gcatcgtgat                                                20


<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

gtgttggcgt acaggtcttt g                                              21


<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52

uuucucacaa cauuugccat t                                              21


<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53

uuagucauca ucuuucucat t                                              21


<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
```

uacuccaaua cucaugucat t 21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 55
auucccacua acuugcaggt t 21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 56
ggaccaaacu uauacaauat t 21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 57
uauuguauaa guuuggucct t 21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 58
auuucaucaa guucuaucct t 21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 59
uuguccuugg gaucuucuct t 21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 60
uuucccaaua gagccuucct t 21

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 61
auggccaucc gaauucuuuu ggucg 25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
uugauggcca uccgaauucu uuugg 25

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
gcugacccug aaguucaucu gcauu 25

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 64
auccacagca uucugcugut t 21

<210> SEQ ID NO 65
<211> LENGTH: 21
<212> TYPE: DNA

-continued

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
uucgaccucg guuagaagat t 21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
gggaacagau guacacucct t 21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
ggaucuuauu ucuucggagt t 21

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
cgaccaaaag aauucggaug gccau 25

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ccaaaagaau ucggauggcc aucaa 25

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 70
aaugcagaug aacuucaggg ucagc 25

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 71
acagcagaau gcuguggaut t 21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 72
ucuucuaacc gaggucgaat t 21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 73
ggaguguaca ucuguuccct t 21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 74
cuccgaagaa auaagaucct t 21

<210> SEQ ID NO 75
<211> LENGTH: 839
<212> TYPE: DNA
<213> ORGANISM: Influenza A virus

<400> SEQUENCE: 75
atggactcca acaccatgtc aagctttcag gtagactgtt tcctttggca tatccgcaag 60
cgatttgcag acaatggatt gggtgatgcc ccattccttg atcggctccg ccgagatcaa 120

-continued

```
aagtccttaa aaggaagagg caacaccctt ggcctcgata tcgaaacagc cactcttgtt    180

gggaaacaaa tcgtggaatg gatcttgaaa gaggaatcca gcgagacact tagaatgaca    240

attgcatctg tacctacttc gcgctacctt tctgacatga ccctcgagga aatgtcacga    300

gactggttca tgctcatgcc taggcaaaag ataataggcc ctctttgcgt gcgattggac    360

caggcgatca tggaaaagaa catagtactg aaagcgaact tcagtgtaat ctttaaccga    420

ttagagacct tgatactact aagggctttc actgaggagg gagcaatagt tggagaaaat    480

tgaatggtaa cacggttcga gtctctgaaa atatacagag attcgcttgg agaaactgtg    540

atgagaatgg gagaccttca cgaatggtaa cacggttcga gtctctgaaa atatacagag    600

attcgcttgg agaaactgtg atgagaatgg gagaccttca ctacctccag agcagaaatg    660

aaaagtggcg agagcaattg ggacagaaat ttgaggaaat aaggtggtta attgaagaaa    720

tgcggcacag attgaaagcg acagagaata gtttcgaaca aataacattt atgcaagcct    780

tacaactact gcttgaagta gaacaagaga taagagcttt ctcgtttcag cttatttaa     839
```

<210> SEQ ID NO 76
<211> LENGTH: 661
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
atggactcca acaccatgtc aagctttcag gtagactgtt tcctttggca tatccgcaag     60

cgatttgcag acaatggatt gggtgatgcc ccattccttg atcggctccg ccgagatcaa    120

aagtccttaa aaggaagagg caacaccctt ggcctcgata tcgaaacagc cactcttgtt    180

gggaaacaaa tcgtggaatg gatcttgaaa gaggaatcca gcgagacact tagaatgaca    240

attgcatctg tacctacttc gcgctacctt tctgacatga ccctcgagga aatgtcacga    300

gactggttca tgctcatgcc taggcaaaag ataataggcc ctctttgcgt gcgattggac    360

caggcgatca tggaaaagaa catagtactg aaagcgaact tcagtgtaat ctttaaccga    420

ttagagacct tgatactact aagggctttc actgaggagg gagcaatagt tggagaaaat    480

tgaatggtaa cacggttcga gtctctgaaa atatacagag attcgcttgg agaaactgtg    540

atgagaatgg gagaccttca cgaatggtaa cacggttcga gtctctgaaa atatacagag    600

attcgcttgg agaaactgtg atgagaatgg gagaccttca ctacctccag agcagaaatg    660

a                                                                    661
```

<210> SEQ ID NO 77
<211> LENGTH: 1211
<212> TYPE: DNA
<213> ORGANISM: Influenza A virus

<400> SEQUENCE: 77

```
atatcgtctc gtattagtag aaacaaggca ttttttcatg aaggacaagt taaattcatt     60

atttttgccg tctgagttct tcaatggtgg aacagatctt catgatctca gagaactctt    120

ctttcttgat ccgtccagac tcgaagtcga ccctggcatc aatccgggcc ctagacacca    180

tggcctccac catgctagaa attccaaccg gtctcctata tgaactgcta gggaaaaatt    240

tctcgaatag attgcagcac ttctggtaca tctgttcatc ctcaaraatt cccctttggc    300

ttgkgttgag aatagaacga ttcctcttgg aagggcttca ggggattgca aagtcttccc    360
```

-continued

```
cgataatcat catccattag ctcccatttt aagcagactt caggcctgtg aagattccgt    420

atattgtata agtttggtcc tccatctgat actaatagcc ctacctttga ttgggtttga    480

tcccacagct tctttaactc aaatgatctt ctcgtctgaa tttgtgtgtc tcccctatgg    540

cacctatatg tgtatctgta gtctttgatg aacaattgaa gagccatctg ggccgttgca    600

ggtccaaggt cattgtttat catgttgttc tttatcactg ttactccaat actcatgtca    660

gctgattcat ttactccaga cactccaaag ctgggtagct ccatgctaaa attagccaca    720

aatccatagc gataaaaaaa gcttgtgaat tcaaatgtcc ctgtcttatt tatataggac    780

ttctttttgc tcatgttgat tcccactaac ttgcaggtcc tgtagaatct gtccactcct    840

gcttgtattc cctcatggtt tggtgcattc actatgagag caaaatcgtc ggatgattgg    900

agcccatccc accagtatat tgtcttggtg tatttctttt gtccaagatt cagtatcgag    960

actcccaaga ccgtacttag catgttgaac atgcccatca tcatcccagg actcagtgat   1020

gctgtgccat ctattagaag aggccttaat tttctcaatt ttcttctttg ttgattcatt   1080

gaagtacttc aggtcaatgc ttgctagcat ttctgctggt atttgagttc gaatcttcat   1140

tcttttactc tcgaacatgt accctttccc tagtcttgcc attttgtttg agaacattat   1200

gggtgccatg c                                                        1211
```

```
<210> SEQ ID NO 78
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

ttcaatggtg gaacagatct tcatgatctc agagaactct tctttcttga tccgtccaga     60

ctcgaagtcg accctggcat caatccgggc cctagacacc atggcctcca ccatgctaga    120

aattccaacc ggtctcctat atgaactgct agggaaaaat ttctcgaata gattgcagca    180

cttctggtac atctgttcat cctcaagaat tcccctttgg cttgtgttga gaatagaacg    240

attcctcttg g                                                         251
```

```
<210> SEQ ID NO 79
<211> LENGTH: 981
<212> TYPE: DNA
<213> ORGANISM: Influenza A virus

<400> SEQUENCE: 79

atgagtcttc taaccgaggt cgaaacgtac gttctttcta tcatcccgtc aggccccctc     60

aaagccgaga tcgcgcagag actggaaagt gtctttgcag gaaagaacac agatcttgag    120

gctctcatgg aatggctaaa gacaagacca atcttgtcac ctctgactaa gggaatttta    180

ggatttgtgt tcacgctcac cgtgcccagt gagcgaggac tgcagcgtag acgctttgtc    240

caaaatgccc taaatgggaa tggggacccg aacaacatgg atagagcagt taaactatac    300

aagaagctca aaagagaaat aacgttccat ggggccaagg aggtgtcact aagctattca    360

actggtgcac ttgccagttg catgggcctc atatacaaca ggatgggaac agtgaccaca    420

gaagctgctt ttggtctagt gtgtgccact tgtgaacaga ttgctgattc acagcatcgg    480

tctcacagac agatggctac taccaccaat ccactaatca ggcatgaaaa cagaatggtg    540

ctggctagca ctacggcaaa ggctatggaa cagatggctg gatcgagtga acaggcagcg    600
```

```
gaggccatgg aggttgctaa tcagactagg cagatggtac atgcaatgag aactattggg    660

actcatccta gctccagtgc tggtctgaaa gatgaccttc ttgaaaattt gcaggcctac    720

cagaagcgaa tgggagtgca gatgcagcga ttcaagtgat cctctcgtca ttgcagcaaa    780

tatcattggg atcttgcacc tgatattgtg gattactgat cgtctttttt tcaaatgtat    840

ttatcgtcgc tttaaatacg gttgaaaaga gggccttcta cggaaggagt gcctgagtcc    900

atgagggaag aatatcaaca ggaacagcag agtgctgtgg atgttgacga tggtcatttt    960

gtcaacatag agctagagta a                                              981


<210> SEQ ID NO 80
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

atacatgcga tcgcatgagt cttctaaccg aggtcgaaac gtacgttctt tctatcatcc     60

cgtcaggccc cctcaaagcc gagatcgcgc agagactgga aagtgtcttt gcaggaaaga    120

acacagatct tgaggctctc atggaatggc taaagacaag accaatcttg tcacctctga    180

ctaagggaat tttaggattt gtgttcacgc tcaccgtgcc cagtgagcga ggactgcagc    240

gtagacgctt tgtccaaaat gccctaaatg ggaatgggga cccgaacaac atggatagag    300

cagttaaact atacaagaag ctcaaaagag aaataacgtt ccatggggcc aaggaggtgt    360

cactaagcta ttcaactggt gcacttgcca gttgcatggg cctcatatac aacaggatgg    420

gaacagtgac cacagaagct gcttttggtc tagtgtgtgc cacttgtgaa cagattgctg    480

attcacagca tcggtctcac agacagatgg ctactaccac caatccacta atcaggcatg    540

aaaacagaat ggtgctggct agcactacgg caaaggctat ggaacagatg gctggatcga    600

gtgaacaggc agcggaggcc atggaggttg ctaatcagac taggcagatg gtacatgcaa    660

tgagaactat tgggactcat cctagctcca gtgctggtct gaaagatgac cttcttgaaa    720

atttgcaggc ctaccagaag cgaatgggag tgcagatgca gcgattcaag tgatcctcgt    780

ttaaacggcg ct                                                        792


<210> SEQ ID NO 81
<211> LENGTH: 1321
<212> TYPE: DNA
<213> ORGANISM: Influenza A virus
<220> FEATURE:
<221> NAME/KEY: modified_base
<222> LOCATION: (1140)..(1140)
<223> OTHER INFORMATION: a, c, t, g, unknown or other
<220> FEATURE:
<221> NAME/KEY: modified_base
<222> LOCATION: (1143)..(1143)
<223> OTHER INFORMATION: a, c, t, g, unknown or other
<220> FEATURE:
<221> NAME/KEY: modified_base
<222> LOCATION: (1248)..(1248)
<223> OTHER INFORMATION: a, c, t, g, unknown or other
<220> FEATURE:
<221> NAME/KEY: modified_base
<222> LOCATION: (1254)..(1254)
<223> OTHER INFORMATION: a, c, t, g, unknown or other
<220> FEATURE:
<221> NAME/KEY: modified_base
<222> LOCATION: (1263)..(1263)
<223> OTHER INFORMATION: a, c, t, g, unknown or other
```

<220> FEATURE:
<221> NAME/KEY: modified_base
<222> LOCATION: (1271)..(1271)
<223> OTHER INFORMATION: a, c, t, g, unknown or other
<220> FEATURE:
<221> NAME/KEY: modified_base
<222> LOCATION: (1287)..(1287)
<223> OTHER INFORMATION: a, c, t, g, unknown or other
<220> FEATURE:
<221> NAME/KEY: modified_base
<222> LOCATION: (1293)..(1293)
<223> OTHER INFORMATION: a, c, t, g, unknown or other
<220> FEATURE:
<221> NAME/KEY: modified_base
<222> LOCATION: (1311)..(1311)
<223> OTHER INFORMATION: a, c, t, g, unknown or other
<220> FEATURE:
<221> NAME/KEY: modified_base
<222> LOCATION: (1315)..(1315)
<223> OTHER INFORMATION: a, c, t, g, unknown or other

<400> SEQUENCE: 81
tgttcgcacc ggaatggatc ccagaatgtg ctctctaatg caaggttcaa cacttcccag 60
aaggtctggt gccgcaggtg ctgcggtgaa aggagttgga acaatagcaa tggagttaat 120
cagaatgatc aaacgtggaa tcaatgaccg aaatttctgg aggggtgaaa atggacgaag 180
gacaagggtt gcttatgaaa gaatgtgcaa tatcctcaaa ggaaaatttc aaacagctgc 240
ccagagggca atgatggatc aagtaagaga aagtcgaaac ccaggaaacg ctgagattga 300
agacctcatt ttcctggcac ggtcagcact cattctgagg ggatcagttg cacataaatc 360
ctgcctgcct gcttgtgtgt atgggcttgc agtagcaagt gggcatgact ttgaaaggga 420
agggtactca ctggtcggga tagacccatt caaattactc caaaacagcc aagtggtcag 480
cctgatgaga ccaaatgaaa acccagctca caagagtcaa ttggtgtgga tggcatgcca 540
ctctgctgca tttgaagatt taagagtatc aagtttcata agaggaaaga aagtaattcc 600
aagaggaaag ctttccacaa gaggggtcca gattgcttca aatgagaatg tggaaatcat 660
ggactccaat accctggaac tgagaagcag atactgggcc ataaggacca ggagtggagg 720
aaataccaat caacaaaagg catccgcagg ccagatcagt gtgcagccta cattctcagt 780
gcagcggaat ctccctttg aaagagcaac cgttatggca gcattcagcg ggaacaatga 840
aggacggaca tccgacatgc gaacagaagt tataagaatg atggaaagtg caaagccaga 900
agatttgtcc ttccaggggc ggggagtctt cgagctctcg gacgaaaagg caacgaaccc 960
gatcgtgcct tcctttgaca tgagtaatga agggtcttat ttcttcggag acaatgcaga 1020
ggagtatgac agttgaggaa aaataccctt ggtttctact taatgcgtgg ctctcgtgcc 1080
agagggtctg atgcggcctg agctggggta caacgtggtg gattttaaca atttgatgan 1140
agnctatgct cacaagtgaa tacaatgacc gatctttctg gaagggtgta gctagcgcaa 1200
ggacagaggt tacttctgaa agaggggatt tatcttcaac ggaaaccntc aaanagaggg 1260
ccngacggga nggaggaaac gagtacnaga aantcaaacc tcccgagaag ntganatgga 1320
a 1321

<210> SEQ ID NO 82
<211> LENGTH: 1030
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82

```
cggaatggat cccagaatgt gctctctaat gcaaggttca acacttccca gaaggtctgg     60

tgccgcaggt gctgcggtga aaggagttgg aacaatagca atggagttaa tcagaatgat    120

caaacgtgga atcaatgacc gaaatttctg gaggggtgaa aatggacgaa ggacaagggt    180

tgcttatgaa agaatgtgca atatcctcaa aggaaaattt caaacagctg cccagagggc    240

aatgatggat caagtaagag aaagtcgaaa cccaggaaac gctgagattg aagacctcat    300

tttcctggca cggtcagcac tcattctgag gggatcagtt gcacataaat cctgcctgcc    360

tgcttgtgtg tatgggcttg cagtagcaag tgggcatgac tttgaaaggg aagggtactc    420

actggtcggg atagacccat tcaaattact ccaaaacagc caagtggtca gcctgatgag    480

accaaatgaa aacccagctc acaagagtca attggtgtgg atggcatgcc actctgctgc    540

atttgaagat ttaagagtat caagtttcat aagaggaaag aaagtaattc caagaggaaa    600

gctttccaca agaggggtcc agattgcttc aaatgagaat gtggaaatca tggactccaa    660

taccctggaa ctgagaagca gatactgggc cataaggacc aggagtggag gaaataccaa    720

tcaacaaaag gcatccgcag gccagatcag tgtgcagcct acattctcag tgcagcggaa    780

tctccctttt gaaagagcaa ccgttatggc agcattcagc gggaacaatg aaggacggac    840

atccgacatg cgaacagaag ttataagaat gatggaaagt gcaaagccag aagatttgtc    900

cttccagggg cggggagtct tcgagctctc ggacgaaaag gcaacgaacc cgatcgtgcc    960

ttcctttgac atgagtaatg aagggtctta tttcttcgga gacaatgcag aggagtatga   1020

cagttgagga                                                          1030
```

<210> SEQ ID NO 83
<211> LENGTH: 1696
<212> TYPE: DNA
<213> ORGANISM: Influenza A virus

<400> SEQUENCE: 83

```
atgaaggcaa tactagtagt tctgctatat acatttgcaa ccgcaaatgc agacacatta     60

tgtataggtt atcatgcgaa caattcaaca gacactgtag acacagtact agaaaagaat    120

gtaacgtaac acactctgtt aaccttctag aagacaagca taacgggaaa ctatgcaaac    180

taagaggagt agccccattg catttgggta aatgtaacat tgctggctgg atcctgggaa    240

atccagagtg tgaatcactc tccacagcaa gctcatggtc ctacattgtg gaaacatcta    300

gttcagacaa tggaacgtgt tacccaggag atttcatcga ttatgaggag ctaagagagc    360

aattgagctc agtgtcatca tttgaaaggt ttgagatatt ccccaagaca agttcatggc    420

ccaatcatga ctcgaacaaa ggtgtaacgg cagcatgtcc tcatgctgga gcaaaaagct    480

tctacaaaaa tttaatatgg ctagttaaaa aagaaaattc atacccaaag ctcagcaaat    540

cctacattaa tgataaaggg aaagaagtcc tcgtgctatg ggcattcac catccatcta     600

ctagtgctga ccaacaaagt ctctatcaga atgcagatgc atatgttttt gtggggtcat    660

caagatatag caagaagttc aagccggaaa tagcaataag acccaaagtg agggatcaag    720

aagggagaat gaactattac tggacactag tagagccggg agacaaaata acattcgaag    780

caactggaaa tctagtggta ccgagatatg cattcgcaat ggaaagaaat gctggatctg    840

gtattatcat ttcagataca ccagtccacg attgcaatac aacttgtcag acacccaagg    900

gtgctataaa caccagcctc ccatttcatt gaagggggt ggacagggat ggtagatgga     960

tggtacggtt atcaccatca aatgagactg gccacaggat tgaggaatgt cccgtctatt   1020
```

-continued

```
caatctagag gcctatttgg ggccattgcc ggtttcattg aagggggggtg gacagggatg   1080

gtagatggat ggtacggtta tcaccatcaa aatgagcagg ggtcaggata tgcagccgac   1140

ctgaagagca cacagaatgc cattgacgag attactaaca aagtaaattc tgttattgaa   1200

aagatgaata tacagttcac agcagtaggt aaagagttca accacctgga aaaaagaata   1260

gagaatttaa ataaaaaagt tgatgatggt ttcctggaca tttggactta caatgccgaa   1320

ctgttggttc tattggaaaa tgaaagaact ttggactacc acgattcgaa tgtgaagaac   1380

ttatatgaaa aggtaagaag ccagctaaaa aacaatgcca aggaaattgg aaacggctgc   1440

tttgaatttt accacaaatg cgataacacg tgcatggaaa gtgtcaaaaa tgggacttat   1500

gactacccaa aatactcaga ggaagcaaaa ttaaacagaa gaaatagatg gggtaaagct   1560

ggaatcaaca aggatttacc agattttggc gatctattca actgtcgcca gttcattggt   1620

actggtagtc tccctggggg caatcagttt ctggatgtgc tctaatgggt ctctacagtg   1680

tagaatatgt atttaa                                                     1696


<210> SEQ ID NO 84
<211> LENGTH: 1796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

cagtgattcg agctcggtac ccggggatcc tctagagatt atacatgcga tcgcatgaag     60

gcaatactag tagttctgct atatacattt gcaaccgcaa atgcagacac attatgtata    120

ggttatcatg cgaacaattc aacagacact gtagacacag tactagaaaa gaatgtaacg    180

taacacactc tgttaacctt ctagaagaca agcataacgg gaaactatgc aaactaagag    240

gagtagcccc attgcatttg ggtgaatgta acattgctgg ctggatcctg ggaaatccag    300

agtgtgaatc actctccaca gcaagctcat ggtcctacat tgtggaaaca tctagttcag    360

acaatggaac gtgttaccca ggagatttca tcgattatga ggagctaaga gagcaattga    420

gctcagtgtc atcatttgaa aggtttgaga tattccccaa gacaagttca tggcccaatc    480

atgactcgaa caaaggtgta acggcagcat gtcctcatgc tggagcaaaa agcttctaca    540

aaaatttaat atggctagtt aaaaaagaaa attcataccc aaagctcagc aaatcctaca    600

ttaatgataa agggaaagaa gtcctcgtgc tatggggcat tcaccatcca tctactagtg    660

ctgaccaaca aagtctctat cagaatgcag atgcatatgt ttttgtgggg tcatcaagat    720

atagcaagaa gttcaagccg gaaatagcaa taagacccaa agtgagggat caagaaggga    780

gaatgaacta ttactggaca ctagtagagc cgggagacaa aataacattc gaagcaactg    840

gaaatctagt ggtaccgaga tatgcattcg caatggaaag aaatgctgga tctggtatat    900

catttcagat acaccagtcc acgattgcaa tacaactgtc agacacccaa gggtgctata    960

aacaccagcc tcccatttca ttgaaggggg gtggacaggg atggtagatg gatggtacgg   1020

ttatcaccat caaatgagac tggccacagg attgaggaat gtcccgtcta ttcaatctag   1080

aggcctattt ggggccattg ccggtttcat tgaagggggg tggacaggga tggtagatgg   1140

atggtacggt tatcaccatc aaaatgagca ggggtcagga tatgcagccg acctgaagag   1200

cacacagaat gccattgacg agattactaa caaagtaaat tctgttattg aaaagatgaa   1260

tatacagttc acagcagtag gtaaagagtt caaccacctg gaaaaaagaa tagagaattt   1320
```

-continued

| | |
|---|---|
| aaataaaaaa gttgatgatg gtttcctgga catttggact tacaatgccg aactgttggt | 1380 |
| tctattggaa aatgaaagaa ctttggacta ccacgattcg aatgtgaaga acttatatga | 1440 |
| aaaggtaaga agccagctaa aaaacaatgc caaggaaatt ggaaacggct gctttgaatt | 1500 |
| ttaccacaaa tgcgataaca cgtgcatgga aagtgccaaa aatgggactt atgactaccc | 1560 |
| aaaatactca gaggaagcaa aattaaacag aagaaataga tggggtaaag ctggaatcaa | 1620 |
| caaggattta ccagattttg gcgatctatt caactgtcgc cagttcattg gtactggtag | 1680 |
| tctccctggg ggcaatcagt ttctggatgt gctctaatgg gtctctacag tgtagaatat | 1740 |
| gtattgttta aacggcgcca atcgtcgacc tgcaggcatg caagcttggc gtaatc | 1796 |

COMPOSITIONS AND METHODS FOR "RESISTANCE-PROOF" SIRNA THERAPEUTICS FOR INFLUENZA

CROSS-REFERENCE TO RELATED PATENT APPLICATIONS

This application claims the benefit of and priority to U.S. Provisional Patent Application No. 61/669,108, filed Jul. 8, 2012, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 5, 2015, is named SIR-011_P001-US_SL.txt and is 36,318 bytes in size.

FIELD OF THE INVENTION

The present invention relates to compositions and methods for use of resistance-proof siRNA therapeutics for prevention and treatment of influenza viral infections.

BACKGROUND

1. Influenza: Biology and Current Prophylaxis and Therapeutics

Influenza A virus is one of the most prevalent respiratory tract infections in humans (Michaelis et al. 2009). Twenty to fifty million U.S. citizens are infected annually resulting in 40,000 deaths. In addition, respiratory virus infections, including flu, are considered to be the leading cause of exacerbation of asthma (Cohen and Castro 2003). For these reasons, the flu virus is considered a significant health threat and a top priority biodefense pathogen by the CDC and National Institutes of Health (NIH). The high risk associated with natural and artificial (bioweapon) flu infection is derived from a number of sources including (1) the ease by which the virus is distributed via aerosol, (2) its ability to escape protective immunity by frequent changes in viral antigens (antigenic drift) and (3) the periodic emergence of new virulent strains resulting from the reassortment of RNA segments between viruses from two different species (antigenic shift). Antigenic drift is the virologic basis for seasonal flu epidemics, while antigenic shift is theorized to be the source of pandemic infections.

Recently, the World Health Organization (WHO) has reported a disturbing increase in the incidence of H5N1 avian influenza infections in human populations. Since 1995, multiple countries have reported outbreaks of H5N1 (Balicer et al. 2007; Uyeki 2009). While the majority of documented cases involve direct viral transfer from wildfowl to human, the WHO and CDC are sufficiently concerned about potential human-to-human transmission to have issued repeated alerts of a H5N1 pandemic. In April 2009, a so-called swine-origin influenza A (H1N1) virus (2009 H1N1 or S-OIV), was identified in Mexico (Dawood et al. 2009). This viral strain originates from triple-reassortant swine flu and is readily transmitted between humans. After its discovery, 2009 H1N1 rapidly spread throughout the world within few weeks. From April to October 17, it was estimated by CDC that 14 million to 34 million infectious cases, 63,000 to 153,000 hospitalizations, and 2,500 to 6,000 2009 H1N1-related deaths occurred. In addition, the epidemiological data indicates that this disease primarily affects people younger than 65 years old, very different from seasonal influenza. Although the death rate caused by 2009 H1N1 was only about 0.45%, lower than the 1918 pandemic (an estimate of 2.5%) and avian flu outbreaks (about 60%), multiple concerns exist. First, mutations in the virus may lead to a more pathogenic strain that increases mortality. Second, since the more deadly avian flu (H5N1; >62%) has also been demonstrated in swine and humans, it is possible that recombination between the 2 strains in either species may result in a highly pathogenic and deadly strain that can migrate readily between species. Third, 2009 H1N1 may reassort with the seasonal flu strains that are resistant to some of the antivirals. This will result in significant difficulties in treating the infected patients.

Currently, two strategies, vaccines and small molecule therapeutics, are utilized to control the spread of flu. Vaccines are predominantly developed from killed or cold-adapted viruses and take advantage of the host immune system to provide limited immunity. While reductions in flu related illness and deaths can be attributed to this approach, especially among high-risk individuals, there are several reasons why vaccines offer limited protection from pandemics. First, the most commonly developed vaccines are based on inactivated viruses. These reagents induce only weak immunity that provides protection for brief (6 month) periods. In light of the facts that 1) only 60-80% of the immunocompetent population and 30-40% of individuals with chronic respiratory ailments (e.g. COPD, asthma) or compromised immune systems receive sufficient protection from vaccination (Kunisaki and Janoff 2009), and 2) vaccines fail to provide protection if administered after infection, alternative approaches are needed to adequately protect the population. A second shortcoming of vaccines involves the complex relationship that exists between the rapid evolution of flu and the limitations associated with reformulating and producing sufficient quantities of vaccines for large populations. The constant evolution of viral antigens frequently renders the previous year's vaccine ineffective and places significant reliance on epidemiological/surveillance data to accurately predict future circulating strains. While these approaches are frequently adequate, the flu outbreak of 2003 and the pandemic in 2009, where predictive models failed to accurately forecast the circulating serotypes and vaccine production capabilities were incapable of responding in a timely manner, demonstrate the need for alternative technologies that can rapidly counter newly emerging serotypes.

In addition to vaccines, there are currently four antiviral drugs approved by the U.S. Food and Drug Administration (US FDA). Two of these agents, amantadine and rimantadine, target the viral ion channel protein, M2. The remaining drugs, zanamivir and oseltamivir, inhibit the function of neuraminidase (NA). While both classes of compounds effectively reduce the severity and duration of flu infections, their efficacy is only limited to the first 24-48 hours after the development of symptoms and can often be associated with side effects. Of still greater concern is the emergence of stable and transmissible drug resistant flu strains (Griffiths 2009; Schirmer and Holodniy 2009). Though the frequency at which NA-targeting drug resistance arises can vary considerably and the associated virulence of resistant strains is often attenuated, exceptions (e.g. the E116G mutation) have been documented (Lackenby et al. 2008). Resistance to oseltamivir has also been identified in the 2009 pandemic virus (www.who.int). Thus, development of a new and flexible anti-flu therapeutic platform is essential.

2. siRNA: A Flexible Molecular Platform for Influenza Prophylaxis and Therapeutics RNA interference (RNAi) is a naturally occurring, highly specific mode of gene regulation. The mechanics of RNAi are both exquisite and highly discriminating (Siomi and Siomi 2009). At the onset, short (19-25 bp) double stranded RNA sequences (referred to as short interfering RNAs, siRNAs) associate with the cytoplasmically localized RNA Interference Silencing Complex (RISC) (Jinek et al. 2009). The resultant complex then searches messenger RNAs (mRNAs) for complementary sequences, eventually degrading (and/or attenuating translation of) these transcripts. Scientists have co-opted the endogenous RNAi machinery to advance a wide range of basic studies. As siRNAs can be designed to target virtually any gene and can be introduced into cells by a variety of methods, RNAi, represents a highly flexible platform by which researchers and clinicians can control diseases including viral infectious diseases. RNAi has been employed to target a wide range of human pathogenic viruses, including flu and other emerging respiratory infectious viruses (Ge et al. 2003 and 2004; Tompkins et al. 2004; Li et al. 2005, Zhou et al. 2007; McSwiggen and Seth 2008; Zhou et al. 2008; Cheng et al. 2009; Sui et al. 2009). The ability of RNAi to 1) efficiently limit viral replication without reliance on host immune functions, and 2) target multiple genes and/or sequences simultaneously, makes this an ideal therapeutic approach for pathogens that have rapidly evolving genomes (e.g. flu). In particular, siRNA therapeutics may benefit specific patient populations such as infants or the elderly who do not produce a strong immune response to a vaccine and may not have full protection from such a program.

3. Challenges Associated with siRNA Therapeutic Development—Resistant Viral Mutants The mutation rate of the influenza virus is estimated to be 1.5×10-5 per nucleotide per infection cycle (Parvin et al. 1986). This high frequency of mutation is the underlying basis behind the emergence of variants (escapers) that are resistant to current M2- and NA-targeting chemotherapeutics (Lackenby et al. 2008; Colman 2009). Though RNAi mediated gene knockdown exhibits a degree of resilience to changes in the siRNA target sequence, mismatches in key positions (including nucleotides localized to the siRNA sequence (positions 2-7 of the antisense strand) and target cleavage (positions 9-11) regions can significantly disrupt siRNA efficacy. Multiple studies in which single siRNAs have been developed to target viral pathogens (e.g. HIV, polio virus, Hepatitis B and C viruses) have documented the emergence of escapers. In most of these cases, resistant virus contains one or more changes in the sequence of the siRNA target site (Gitlin et al. 2005; Grimm et al. 2006; von Eije et al. 2008). Mutations in the sequence outside of the siRNA target site were also found in HIV resistant mutants (Leonard et al. 2008). The changes in the RNA secondary structure or/and an evolutionary tuning of viral transcriptional regulation may serve as evasion mechanisms. As escaper populations appear rapidly, novel strategies must be identified if effective RNAi-based viral therapeutics are to become a reality.

Therapeutic strategies that may prevent and/or reduce the emergence of resistant variants include: (1) targeting regions of essential (viral) genes that are highly conserved, and (2) targeting two or more viral genes simultaneously. Moreover, as the rate at which two resistance inducing mutations occur is the product of the frequency of either mutation occurring separately (i.e. 2.25×10-10 per infection cycle), multigene targeting is expected to lessen the frequency at which resistant viral pathogens appear (Gitlin et al. 2005; Grimm et al. 2006; von Eije et al. 2008). We predict that strategies that incorporate both approaches: multiple-gene targeting of conserved regions, will yield the most effective therapeutic platform to combat influenza by RNAi.

4. Challenges Associated with siRNA Therapeutic Development-Delivery Barriers

There are many biological barriers and factors that protect the lungs from foreign particles, such as a thick and elastic mucus layer that may bind inhaled drugs and remove them via mucus clearance mechanism, low basal and stimulated rates of endocytosis on the apical surfaces of well-differentiated airway epithelial cells, the presence of RNase extra- and intra-cellularly, and the presence of endosomal degradation systems in the target cells, among others. Overcoming the difficulties concerning respiratory tract delivery and effective cellular entry and function will pave the way for siRNA as a pulmonary flu therapeutic. In addition, the delivery vehicle and mode of administration must be chosen to be appropriate to the stage of the infection and provide the fastest onset of silencing at the required site of action, e.g. early stage infection/prophylaxis at the lungs and later stage disease through systemic administration. Among them, pulmonary delivery through inhalation provides a noninvasive means for site specific administration to different regions of the lung—resulting in increased bioavailability and fewer adverse effects than with intravenous administration. In a pandemic setting this delivery approach will allow ease of administration directly by patients. In addition, the findings that flu virus is capable of infecting vascular endothelial cells and that endothelial cells express both human and avian flu receptors have urged the development of vascular endothelial cell-directed delivery of antiviral to control some of the systemic syndromes caused by the virus (Sumikoshi et al. 2008; Yao et al. 2008).

Intranasal (i.n.) delivery of siRNA in a mouse model system has successfully reduced expression of a number of endogenous pulmonary targets. Similarly, i.n. delivery of siRNAs targeting a range of viral pathogens (including flu, SARS, and RSV) have successfully knocked down viral gene expression and diminished viral titers (Ge et al. 2004; Bitko et al. 2005; Li et al. 2005). Some delivery carriers were also shown to deliver siRNAs to the mouse lungs via intravenous injection (Ge et al. 2004). In summary, development of formulations for pulmonary delivery of siRNA should be further advanced.

DESCRIPTION OF THE INVENTION

Figure 1:
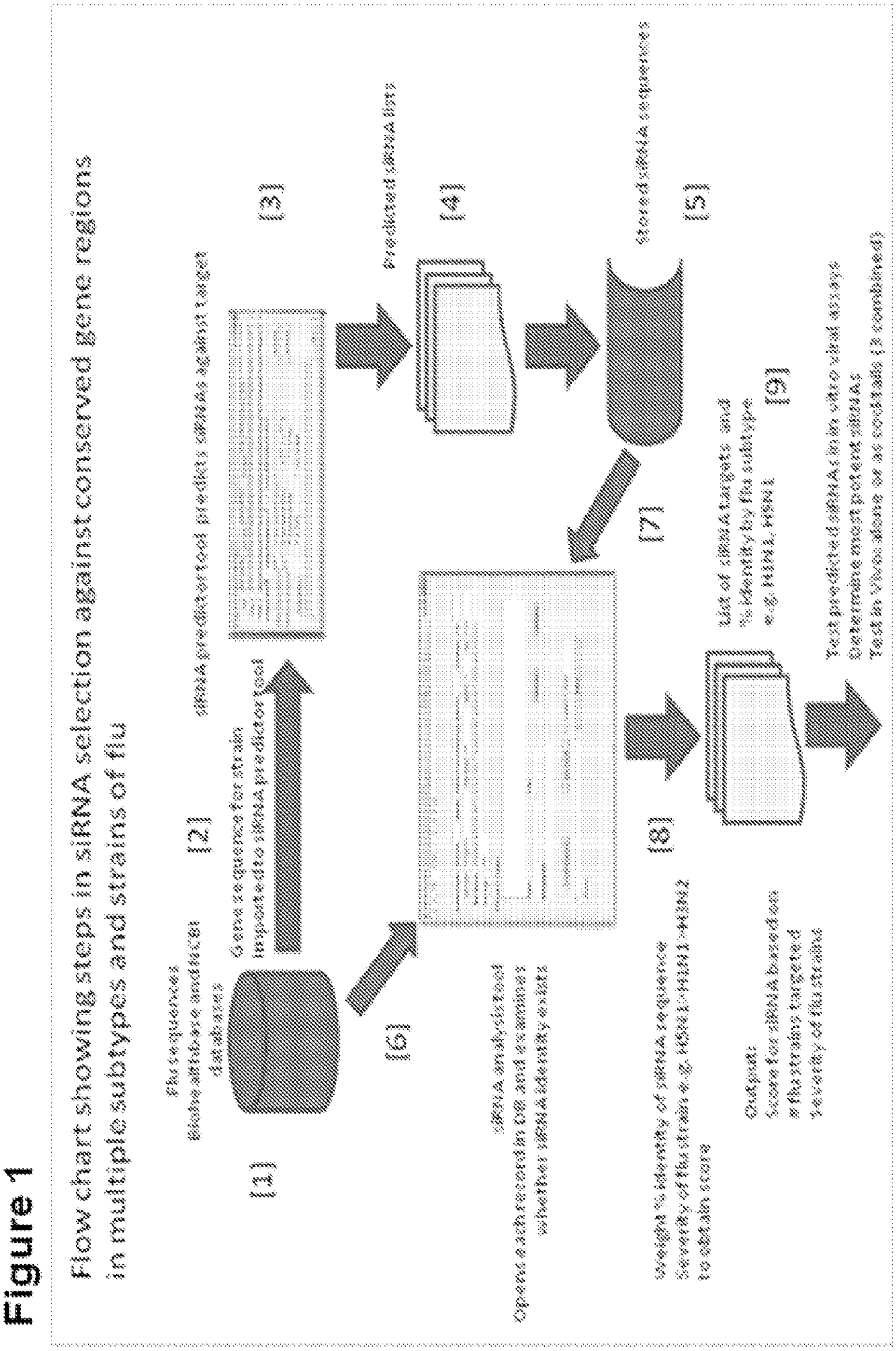
FIG. 1. Flow chart showing steps in siRNA selection against conserved gene regions in multiple subtypes and strains of influenza A virus.

The present invention relates to compositions and methods for use of resistance-proof siRNA therapeutics for prevention and treatment of influenza viral infections. As used herein, the term "resistance-proof" means able to meet the challenge of viral resistance due to viral mutations and antigenic drift by continuing to target the changed viruses.

The compositions include a pharmaceutical composition comprising an siRNA molecule that targets a conserved region of an influenza virus gene and a pharmaceutically acceptable polymeric carrier. In one embodiment, the polymeric carrier condenses the molecules to form a nanoparticle.

In a preferred embodiment, the composition comprises at least two different siRNA molecules and a pharmaceutically acceptable carrier. One of the siRNA molecules targets a conserved region of an influenza virus gene and the other siRNA molecule targets a conserved region of a different influenza virus gene. The genes can be in the same virus strain or in two different virus strains. The composition can include one or more additional siRNA molecules that target still other influenza virus genes in the same virus strain or in different virus strains.

As used herein, an "siRNA molecule" or an "siRNA duplex" is a duplex oligonucleotide, that is a short, double-stranded polynucleotide, that interferes with the expression of a gene in a cell, after the molecule is introduced into the cell, or interferes with the expression of a viral gene. SiRNA molecules are chemically synthesized or otherwise constructed by techniques known to those skilled in the art. Such techniques are described in U.S. Pat. Nos. 5,898,031, 6,107,094, 6,506,559, 7,056,704 and in European Pat. Nos. 1214945 and 1230375, which are incorporated herein by reference in their entireties.

Whenever a single siRNA molecule is described herein, it should be understood that the description can apply to more than one of the molecules in the preferred composition. Except for structural differences because the two or more siRNA molecules target conserved regions in different viral genes, the molecules can be the same in structure. For example, they can have the same number of base pairs. The molecules can also have additional structural differences. For example, they may differ in length, i.e., the number of base pairs that each contains.

One or more of the ribonucleotides comprising the molecule can be chemically modified by techniques known in the art. In addition to being modified at the level of one or more of its individual nucleotides, the backbone of the oligonucleotide can be modified. Additional modifications include the use of small molecules (e.g. sugar molecules), amino acids, peptides, cholesterol, and other large molecules for conjugation onto the siRNA molecule.

In the present invention, the siRNA molecules target conserved regions of influenza virus genes. As used herein, "target" or "targets" means that the molecule binds to a complementary nucleotide sequence in an influenza virus gene, which is an RNA molecule, or it binds to mRNA produced by the gene. This inhibits or silences the expression of the viral gene and/or its replication. As used herein, a "conserved region" of an influenza virus gene is a nucleotide sequence that is found in more than one strain of the virus, is identical among the strains, rarely mutates, and is critical for viral infection and/or replication and/or release from the infected cell.

In one embodiment, the siRNA molecule is a double-stranded oligonucleotide with a length of about 16 to about 35 base pairs. In one aspect of this embodiment, the molecule is a double-stranded oligonucleotide with a length of about 19 to about 27 base pairs. In another aspect of this embodiment, it is a double-stranded oligonucleotide with a length of about 21 to about 25 base pairs. In still another aspect of this embodiment, it is a double-stranded oligonucleotide with a length of about 25 base pairs. In all of these aspects, the molecule may have blunt ends at both ends, or sticky ends with overhangs at both ends (unpaired bases extending beyond the main strand), or a blunt end at one end and a sticky end at the other. In one particular aspect, it has blunt ends at both ends.

In one embodiment, the sequences comprising the siRNA molecule have no homology to a mammalian gene. In one aspect of this embodiment, the mammal is a human, mouse, ferret, or monkey.

The siRNA molecule targets any influenza virus, including influenza A and influenza B. In one embodiment, the influenza virus is an influenza A virus. This virus includes subtypes H1N1, H3N2, H5N1, H7N2, H7N9, and H9N2 among others of the form HxNy denoting the types of hemagglutinin and neuraminidase sequences.

The siRNA molecule targets the conserved region of any influenza virus gene. In one embodiment, the virus gene is an influenza A virus gene selected from the group consisting of M2, PA, PB (including PB1 and PB2), and NP.

In one aspect of this embodiment, the siRNA molecule targets the M2 gene of the influenza A H1N1, H3N2, H5N1, H7N2, H7N9, and H9N2 subtypes. In a further aspect of this embodiment, the siRNA molecule comprises the sense sequence: 5'-GAGCGAGGACUGCAGCGUAGACGCU-3' (SEQ ID NO: 1).

In another aspect of this embodiment, the siRNA molecule targets the NP gene of the influenza A H1N1, H3N2, H5N1, H7N2, H7N9, and H9N2 subtypes. In a further aspect of this embodiment, the siRNA molecule comprises the sense sequence: 5'-GUGUGGAUGGCAUGCCACUCUGCTG-3' (SEQ ID NO: 2).

In still another aspect of this embodiment, the siRNA molecule targets the influenza A PB1 gene. In a further aspect, the influenza A PB1 gene is the H1N1 PB1 gene, and the siRNA molecule is selected from the group consisting of PB1a, 5'-UGGCAAAUGUUGUGAGAAAdTdT-3' (SEQ ID NO: 3) (sense sequence), PB1b, 5'-UGAGAAAGAUGAUGACUAAdTdT-3' (SEQ ID NO: 4) (sense sequence), PB1c, 5'-UGACAUGAGUAUUGGAGUAdTdT-3' (SEQ ID NO: 5) (sense sequence), and PB1d, 5'-CCUGCAAGUUAGUGGGAAUdTdT-3' (SEQ ID NO: 6) (sense sequence).

In still another aspect of this embodiment, the siRNA molecule targets the influenza A PA gene. In a further aspect, the influenza PA gene is the H1N1 PA gene, and the siRNA molecule is selected from the group consisting PAa, 5'-GGAUAGAACUUGAUGAAAUdTdT-3' (SEQ ID NO: 7) (sense sequence), PAb,5'-GAGAAGAUCCCAAGGACAAdTdT-3' (SEQ ID NO: 8) (sense sequence), and PAc, 5'-GGAAGGCUCUAUUGGGAAAdTdT-3' (SEQ ID NO: 9) (sense sequence).

In one embodiment, the siRNA molecule of the composition is selected from the molecules listed in Tables 2, 4, and 5. In one aspect of this embodiment, the siRNA molecule comprises the sense sequence: 5'-ACGCUGCAGUCCUCGCUCACUGGG-3' (SEQ ID NO: 10) and the antisense sequence: 5'-CCCAGUGAGCGAGGACUGCAGCGUA-3' (SEQ ID NO: 11). In another aspect, the siRNA molecule comprises the sense sequence: 5'-GCAAUUGAGGAGUGCCUGAdTdT-3' (SEQ ID NO: 12) and the antisense sequence: 5'-UCAGGCACUCCUCAAUUGCdTdT-3' (SEQ ID NO: 13).

The siRNA molecules of the invention also include ones derived from those listed in Tables 2, 4, and 5 and otherwise herein. The derived molecules can have less than the 25 base pairs shown for each molecule, down to 16 base pairs, so long as the "core" contiguous base pairs remain. That is, once given the specific sequences shown herein, a person skilled in the art can synthesize molecules that, in effect, "remove" one or more base pairs from either or both ends in any order, leaving the remaining contiguous base pairs, creating shorter molecules that are 24, 23, 22, 21, 20, 19, 18, 17, or 16 base pairs in length. Thus, the derived molecules consist of: a) 24 contiguous base pairs of any one or more of the molecules in Tables 2, 4, and 5; b) 23 contiguous base pairs of any one or more of the molecules in Tables 2, 4, and 5; c) 22 contiguous base pairs of any one or more of the molecules in Tables 2, 4, and 5; b) 21 contiguous base pairs of any one or more of the molecules in Tables 2, 4, and 5; d) 20 contiguous base pairs of any one or more of the molecules in Tables 2, 4, and 5; e) 19 contiguous base pairs of any one or more of the molecules in Tables 2, 4, and 5; f) 18 contiguous base pairs of any one or more of the molecules in Tables 2, 4, and 5; g) 17 contiguous base pairs of any one or more of the molecules in Tables 2, 4, and 5; and h) 16 contiguous base pairs of any one or more of the molecules in Tables 2, 4, and 5. It is not expected that molecules shorter than 16 base pairs would have sufficient activity or sufficiently low off-target effects to be pharmaceutically useful; however, if any such constructs did, they would be equivalents within the scope of this invention.

Alternatively, the derived molecules can have more than the 25 base pairs shown for each molecule, so long as the 25 contiguous base pairs remain. That is, once given the specific sequences shown in the tables, a person skilled in the art can synthesize molecules that, in effect, "add" one or more base pairs to either or both ends in any order, creating molecules that are 26 or more base pairs in length and containing the original 25 contiguous base pairs.

In one embodiment, the siRNA molecule includes a potency enhancing motif. As used herein, the term "potency-enhancing motif" means an RNA sequence included in the siRNA molecule that increases the therapeutic effect of the molecule in an animal model compared to the same molecule without the sequence. For example, when the molecules are tested in a virus-challenged mouse model, they exhibit much more potent antiviral activity than other influenza-specific siRNA molecules not containing this motif, even though the two types of influenza-specific siRNA molecules have the same antiviral activity in a cell culture test. An example of such a motif is the sequence: sense, 5'-ACUCC-3'; antisense, 5'-GGAGU-3'.

The siRNA molecule may also include an immune-stimulating motif. Such motifs can include specific RNA sequences such as 5'-UGUGU-3' (Judge et al., *Nature Biotechnology* 23, 457-462 (1 Apr. 2005)), 5'-GUCCUUCAA-3' (Hornung et al., *Nat. Med.* 11, 263-270(2005). See Kim et al., *Mol Cell* 24; 247-254 (2007). These articles are incorporated herein by reference in their entireties. These are siRNA sequences that specifically activate immune responses through Toll-like receptor (TLR) activation or through activation of key genes such as RIG-I or PKR. In one embodiment, the motif induces a TH1 pathway immune response. In another embodiment, the motif comprises 5'-UGUGU-3', 5'-GUCCUUCAA-3', 5'-GGGxGG-3' (where x is A, T, G and C), or CpG motifs 5'-GTCGTT-3'.

The pharmaceutical compositions of the invention preferably contain more than one type of siRNA molecule, wherein each molecule targets a different conserved region of an influenza virus gene or a conserved region of different influenza virus genes. In one embodiment comprising a composition with two different siRNA molecules, one siRNA molecule comprises the sense sequence: 5'-UACGCUGCAGUCCUCGCUCACUGGG-3' (SEQ ID NO: 14); and the antisense sequence: 5'-CCCAGUGAGCGAGGACUGCAGCGUA-3,' (SEQ ID NO: 11) and the other siRNA molecule comprises the sense sequence: 5'-GCAAUUGAGGAGUGCCUGAdTdT-3' (SEQ ID NO: 12) and the antisense sequence: 5'-UCAGGCACUCCUCAAUUGCdTdT-3' (SEQ ID NO: 13).

The pharmaceutically acceptable carrier is a polymer. Examples of polymers include a biodegradable histidine-lysine polymer, a biodegradable polyester, such as poly (lactic acid) (PLA), poly(glycolic acid) (PGA), and poly (lactic-co-glycolic acid) (PLGA), a polyamidoamine (PAMAM) dendrimer, (Polyallylamine (PAA) and poly(dimethylaminoethyl methacrylate) (PDMAEM), a cationic lipid, or a PEGylated PEI. Cationic lipids include DOTAP, DOPE, DC-Chol/DOPE, DOTMA, and DOTMA/DOPE.

In one embodiment, the carrier is a histidine-lysine copolymer that forms a nanoparticle with the siRNA molecule. In one aspect of this embodiment, the diameter of the nanoparticle is about 100 nm to about 400 nm. In another aspect of this embodiment, the composition is a lyophilized powder.

In one embodiment, the polymeric carrier further comprises a Pegylated-PEI with a molecular weight smaller than 6KD.

The compositions of the invention are used prophylactically or therapeutically against influenza infections, especially influenza A infections. A prophylactically or therapeutically effective amount of the composition is administered to the subject. The term "subject" refers to any animal, including humans. Thus, the invention includes a prophylactic method of preventing an influenza infection in a subject or reducing the severity of a subsequent infection, and it includes a therapeutic method of treating an influenza infection in a subject. In one embodiment, the subject is a mammal. In one aspect of this embodiment, the mammal is a laboratory animal, such as a rodent, ferret, or non-human primate. In a particular embodiment, the mammal is a human.

The compositions are administered by techniques known to those skilled in the art. For example, they may be administered intravenously, intraperitoneally, and via the airway, such as intranasally. The dosages are determinable by those skilled in the art, given the teachings contained herein.

As used herein, the singular forms "a," "an," and "the" refer to one or more, unless the context clearly indicates otherwise.

The following examples illustrate certain aspects of the invention and should not be construed as limiting the scope thereof.

EXAMPLES

Example 1. Create a Novel Algorithm for Identification of siRNA Sequences Covering Multiple Influenza Viral Strains Gene sequences are obtained from the databases of sequenced flu genes (1) and imported into the siRNA predictor tool (2). The predictor tool identifies all potential siRNAs of a given length (e.g. 25mer) against the gene and the list is exported and saved. Using an siRNA analysis tool, each gene in the database is evaluated to determine identity with the siRNA sequence. A score is applied to each strain of influenza based on degree of identity with the siRNA sequence and region of identity.

SiRNA therapeutics may benefit specific patient populations such as infants or the elderly who do not produce a strong immune response to a vaccine and may not have full protection from such a program. The cross reactivity between siRNA against H1N1 and H5N1 strains of the virus will hopefully provide a significant benefit should the rapid ability to spread evidenced by the former virus be combined with the highly pathogenic and lethal effects of the latter.

Using our bioinformatics programs we have identified 25mer blunt ended siRNAs against key regions of genes important to the replication lifecycle of influenza viruses. These genes included M2, PB and PA genes but each and every gene of all influenza viruses can be included in this list. The software for siRNA prediction determines siRNAs of a given length (19-25 base blunt ended duplex RNAs) that have identity to a gene that we are aiming to silence. A flow chart showing the process can be found in FIG. 1.

The score is further adjusted based on the need to cover specific viral strains e.g. a higher weighting (100%) can be applied for H1N1 and H5N1 strains than, say H3N2 which may not be prevalent in an outbreak or pandemic. The output is a list of siRNA sequences and the range of viral strains that may respond to gene silencing by the siRNA. At this point we would refine the algorithm by empirically evaluating the activity of the most interesting siRNAs for each molecular viral target by measuring the effect of single siRNAs transfected in MDCK cells in vitro on viral titer in these cells. Upon identification of the most potent siRNAs we would then examine combinations of 2 or 3 of these with in vivo models (animal models) to observe effects on decreasing viral titer of H5N1 or H1N1 strains after intranasal administration of the siRNA either as a single entity or as a cocktail (of 3 distinct siRNAs).

The software predicts siRNAs with appropriate thermodynamic properties, removes known immune stimulating motifs and those siRNAs which were not within the appropriate range for GC content (35-65%). A list of the siRNA sequences that meet our final criteria is exported to a file and saved on a computer hard drive. Another software tools then opens the siRNA list file and sequentially examines each record in the database for identity between the predicted siRNA sequence and the gene sequence for the viral strain and gene. Two searches can be made: 1) for exact identity between siRNA sequence and gene sequence across all bases and 2) a partial match—where specific bases within the siRNA do not match exactly with the paired gene sequence. In the latter case the software outputs the region of the siRNA where there is an exact match in capital letters e.g. CCATCGTTCCAAGGGTACGGCATAA (SEQ ID NO: 15) would imply that an siRNA with this sequence would match exactly with the complementary sequence in the targeted gene. In this case the match would be 100%. If a region is not identical with the predicted gene sequence it is represented by small case letters for the bases. E.g. an siRNA against the same sequence as the first case but which differed at the last base would be written as CCATCGTTCCAAGGGTACGGCATAa (SEQ ID NO: 15). It is well known that the minimum effective length of an siRNA that can silence a gene with high potency is a 19 base duplex. In the example given this was predicting a 25mer siRNA.

We have previously demonstrated that a 25mer is more potent than a 19mer in silencing a gene in vitro. To ensure optimal thermodynamic properties for the siRNAs it is important that the first 2 bases do not include a T or A while it is better that the last 2 bases in the siRNA ARE a T or A. The reason for this is that it is believed that such bases allow the duplex siRNA to unwind more easily and pairing of the antisense strand within Dicer. While a region of identity in many siRNAs can include both a T and an A base at the terminus, it is sometimes not feasible to identify an siRNA with absolute identity in this region. Consequently, if the base pairing in the terminal region is not exact this may help with efficacy of the siRNA. Therefore our algorithm for scoring predicted siRNA sequences provides a weighting for siRNAs that meet all of our criteria (exact identity along entire length AND have the correct bases at both the 2 start bases and 2 end bases in the sequence). Such a sequence would be weighted according to the formula:

[(Predicted siRNA length−minimum effective siRNA length)*(consecutive base matches)]/number of base mismatches+1.E.g.,in our example,a25mer with exact identity would score as follows[(25−19)*(25)]/1)=150.

If we had a 25 mer siRNA with the following sequence CCA TCG TTC CAA GGG TAC GGC ATA A (SEQ ID NO: 15), i.e., 1 base mismatch at the end, the value would look like [(25-19)*(24)]/2)=72. A sequence as follows CCA TCG TTC CAA GGG TAC GTC ATA A (SEQ ID NO: 16) would score [(25−19)*(19)]/2)=57 so a base mismatch further from the terminus would reduce the score. Further, a sequence like CCA TCG TTC CAA GGG TAC Gttccgg (SEQ ID NO: 17) where all of the last 6 bases match would be scored as [(25−19)*(19)]/6)=19. This provides an estimate of how to rank the siRNAs of interest to pursue against a viral strain. Additional weighting can be provided based on the prevalent disease strain in the general population (e.g. H1N1 versus H5N1 for example) or even within a strain the isolate that is being observed most frequently.

Figure 2:
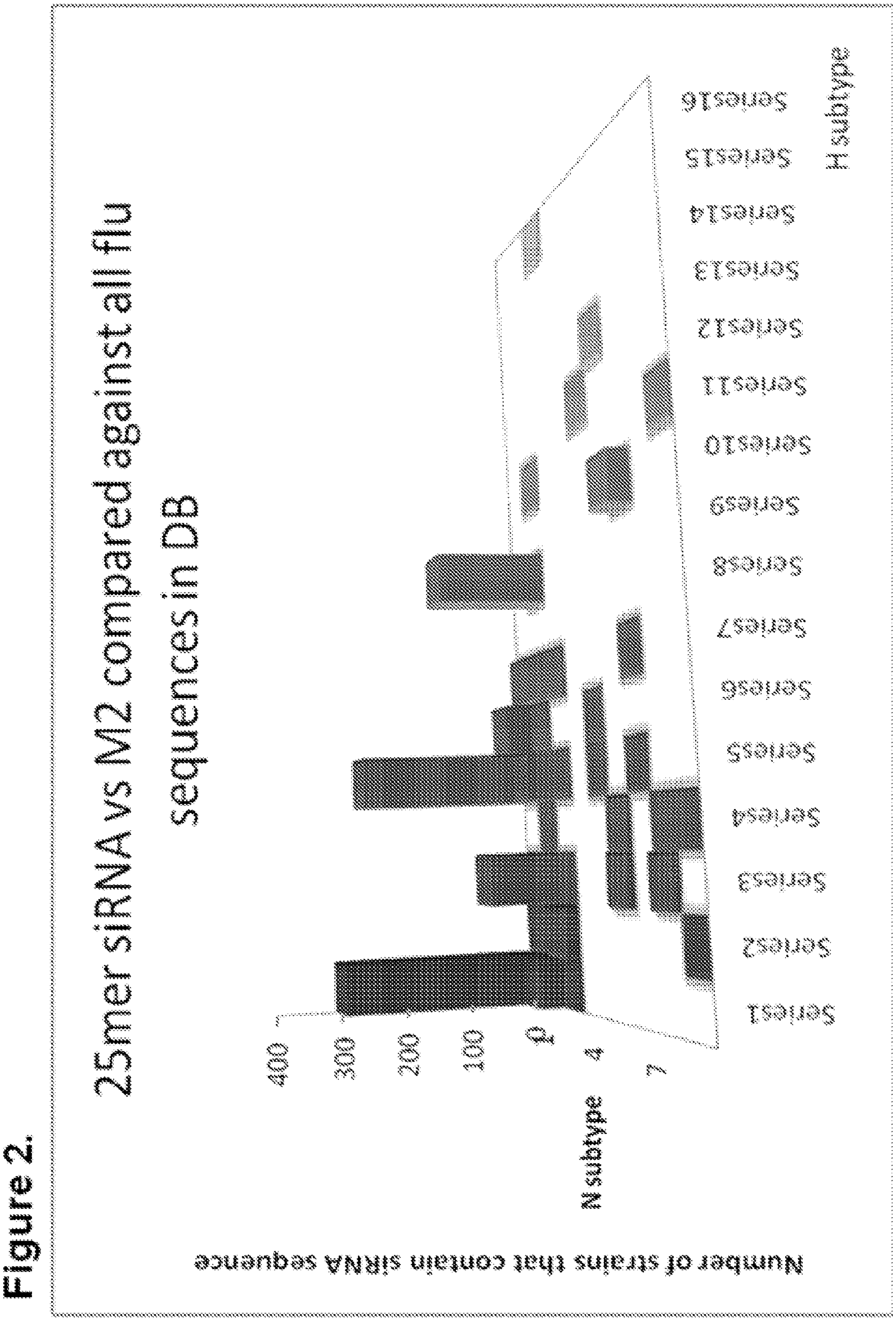
FIG. 2. A 25 mer M2 specific siRNA sequence has homology with the conserved region of many strains of influenza A FIG. 3. Combination of siRNA duplexes against M1/M2 gene and PB1/PB2 gene resulted in broader coverage of influenza A subtypes.

After identification of the siRNA sequences that meet our criteria, additional software tools allow comparison between these siRNA sequences and a database containing all gene sequences of sequenced strains of the influenza viruses (a combined list from the NCBI flu database and biohealthbase files). The bioinformatics tools identify influenza strains exhibiting 100% identity to the predicted siRNA sequences and output from the queries provided the viral gene the siRNA would recognize and the strain of the virus in which that sequence was found. Additionally we can get a value incorporating the weighting score which allows for siRNAs which are not identical to the entire gene region of interest. Interestingly, siRNAs against one viral gene did not show overlap with other viral genes. Furthermore, as shown below in FIG. 2, we could identify siRNAs this way that were able to react against a large number of strains of the virus (including demonstration of cross-reactivity between important strains including H1N1 (swine flu) and H5N1 (avian flu); In other cases (FIG. 3), we could identify siRNAs only against a single specific strain of the virus. By expanding the searches we perform against all genes and across all sequenced flu strains we can identify siRNAs that will be able to a) exhibit a broad strain specificity or b) be selective for a specific gene within a particular viral strain. By combining 1 siRNA from the list with broad strain activity (e.g. against M2) with an siRNA specific for another gene (e.g. NP, PB1 or PB2) from H1N1 together with a 3rd siRNA against another gene target in the virus we can produce a cocktail with broad efficacy against multiple strains of the virus yet the multitargeting will prevent the ability of viral mutation to escape therapeutic pressure.

Figure 3:
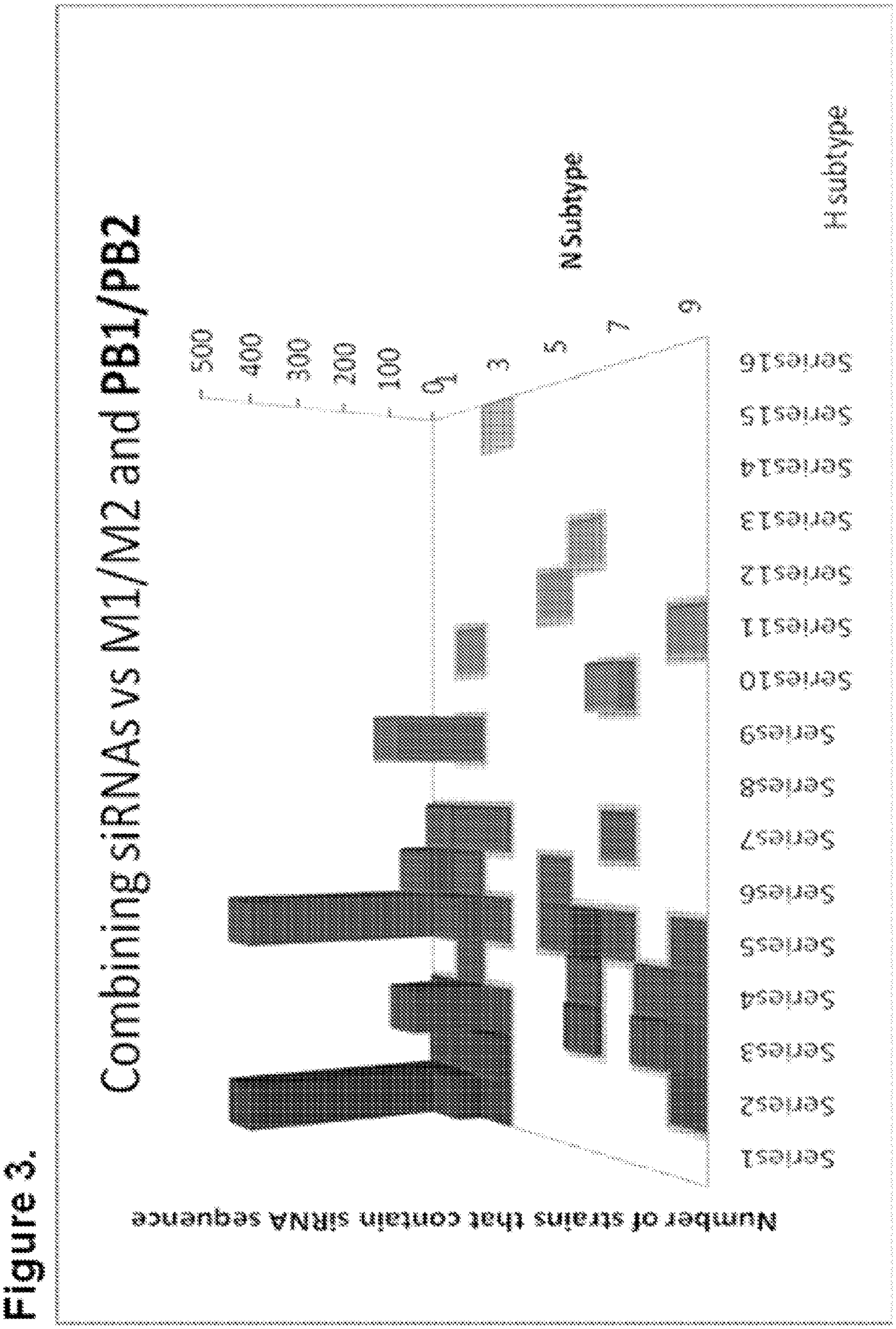

By identifying siRNA sequences against other key target genes within the virus and then looking at overlap between the number of strains of flu that these siRNA cocktails may then target we have shown that a combination of an siRNA against M2 with broad strain specificity (FIG. 2) when combined with an siRNA against PB1/2 also with broad strain specificity we can increase the potential strains that are targeted by one or both siRNA (FIG. 3).

We can see that strain coverage increases to ~500 fully sequenced flu viruses. The degree of coverage for H1N1 and H5N1 is about equal suggesting these selected siRNAs may be targeting conserved regions within many of these sequenced strains. We also see coverage of less pathogenic strains such as H3N2 with the combined sequences. Such conservation in gene regions may provide a point of vulnerability for the influenza virus since these regions may be expected to exhibit lower frequencies of mutation and make them better targets for therapeutic intervention. By multiplexing the therapeutic strategy (delivery of siRNAs against more than one viral gene) we can expect to further limit the potential escape of the virus from therapeutic pressure by mutation in a single gene. The prospect of mutation in two genes at point covered specifically by siRNA sequences is extremely unlikely.

Even by including these two siRNAs in a cocktail we may target as many as 500 of the ~1700 H1N1 strains in the biohealthbase database and a similar number of H5N1 strains. The cross-targeting between these 2 virus types means we will provide a single therapeutic against a geographically widespread but less pathogenic virus (H1N1**; producing 816 deaths in 134503 cases; or a 0.6% death rate) with cross reactivity against the less widespread but more lethal avian flu virus (H5N1; producing 254 deaths from 406 cases; a 62% death rate).

There are 2 ways to predict siRNAs against conserved regions of viral genes. One way is to align all the genes from multiple strains and identify overlapping regions within the gene and then determine whether siRNAs with relevant pharmacological properties can be designed against these specific regions. This approach severely limits the number of siRNAs that can be predicted and siRNAs designed with these criteria may exhibit lower potency in gene silencing.

The method we have chosen is to predict siRNAs de novo against each gene sequence within all sequenced viral strains applying the optimal thermodynamic criteria for siRNA potency. This provides a database containing siRNAs that can rapidly be pressed into use in a cocktail of multi-targeted siRNAs. After the siRNA sequences are predicted we then compare the predicted siRNA sequence across all genes in all viral strains to identify those that exhibit the ability to show identity to and silence the gene in the largest number of species. We will then compare the strain coverage that might be expected when we combine siRNAs against select genes into a cocktail targeting three distinct genes. Furthermore, we designed criteria into our selection algorithm that can provide a "weighting" for the most prevalent flu strain in the general population and allows tailoring of a cocktail to aid in treatment of flu. The ability to rapidly synthesize and characterize siRNAs together with the fact that an siRNA of the same length demonstrates similar charge and hydrophobicity as well as molecular weight makes the formulation of such siRNAs very much easier than a vaccine or small molecule. Consequently a delivery vehicle that shows delivery of one siRNA sequence to the lung may be expected to deliver an siRNA against a distinct sequence with equal efficacy. This benefit means that as the predominant flu virus changes—either seasonally or geographically—the siRNA therapeutic cocktail can also be rapidly tailored to ensure therapeutic benefit to patients.

Currently our algorithms and predictions have been based on siRNA sequence identity with the gene target within a virus gene. SiRNAs as short as 19mer have been demonstrated to effectively silence genes in vitro and in vivo. Since our siRNAs are 25 bases in length, there may be some sequence redundancy that will still allow complete silencing of a target gene. We are building tools to allow examination of regions that may not be 100% identical to the siRNA sequence across all bases but which show identity in 19 consecutive bases. The ability to identify those genes that do not exhibit complete identity along all 25 bases of the siRNA may increase the number of viral strains that can possibly be targeted by an siRNA. The prediction algorithm provides an increased weighting for genes with identity across all 25 bases and a weighting of the results based on a change in the expected thermodynamic properties can be made where shorter regions overlap (see above). Such a scoring scale allows increased scores for consecutive regions of identity.

The siRNAs predicted from our algorithms are further evaluated with in vitro assays and the algorithm modified to incorporate the empirical results based on efficacy of the siRNAs against viral titer. In this way possible regions within the viral genome with secondary structure that inhibits the pairing of the siRNA and the gene within DICER can be excluded from consideration for siRNA prediction. As we identify these regions their sequence may be included in an exclusion algorithm for the siRNAs to be tested. The data obtained from these studies will allow us to predict siRNAs with the greatest scope of viral inhibition to be included in a therapeutic cocktail that can be administered intranasally.

Figure 4:
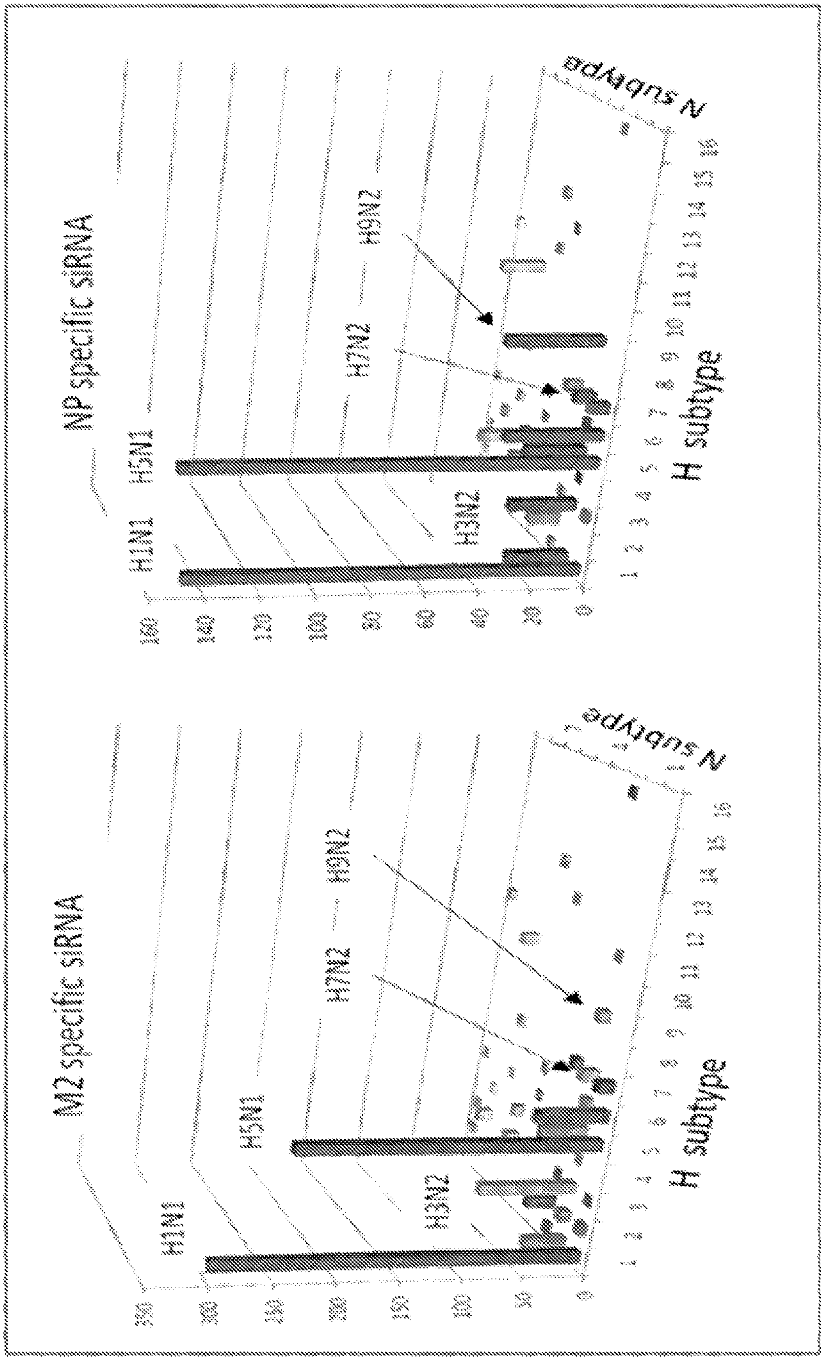
FIG. 4. The selected siRNA duplexes targeting M2 and NP genes of influenza A have homology to H5N1, H1N1, H3N2, H7N2 and H9N2, etc.

One study (FIG. 4.) has demonstrated that two siRNA duplexes selected based on their activities protecting MDCK cell from CPE after H1N1 challenge. The selected siRNA duplexes were targeting M2 and NP genes of influenza A and demonstrated homology to H5N1, H1N1, H3N2, H7N2 and H9N2, etc. These two sequences are the best candidates for the active pharmaceutical ingredients for siRNA therapeutics as the "resistance-proof" drug against influenza infection.

Example 2. Subcloning Influenza Viral Sequences as Surrogates for siRNA Potency Examination In Vitro The viral nucleic acid drug screening needs strict laboratory conditions, such as H5N1 or H1N1 may require BSL-3 condition. In order to screen siRNA inhibitors targeting the influenza virus in an ordinary (BL-2) laboratory, we used the viral gene segments amplified by PCR from cDNA of H1N1 viral genome and subcloned them into a Luciferase reporter gene vector. As a result, we were able to screen the siRNA inhibitors and other types of drugs against viruses in our BL-2 laboratories.

The psiCHECK™-2 Vector is designed to provide a quantitative and rapid approach for optimization of RNA interference (RNAi) activity. These vectors enable the monitoring of changes in expression of a target gene fused to the reporter gene. In this vector, *Renilla* Luciferase is used as a primary reporter gene, and the gene of interest can be cloned into the multiple cloning region located downstream of the *Renilla* Luciferase translational stop codon. Initiation of the RNAi process toward a gene of interest can result in cleavage and subsequent degradation of fusion mRNA. Measurement of decreased *Renilla* Luciferase activity is a convenient indicator of RNAi effect.

TABLE 1

Primers used for PCR amplification.

| Gene symbol | FORWARD 5'-3' | REVERSE 5'-3' |
|---|---|---|
| M | ATACATGCGATCGCA<br>TGAGTCTTCTAACC | AGCGCCGTTTAAACG<br>AGGATCACTTGAAT |
| NP | ATTAATGCGATCGCC<br>GGAATGGATCCCAG | AGCGCCGTTTAAACT<br>CCTCAACTGTCATA |
| NS | ATTAATGCGATCGCA<br>TGGACTCCAACACC | AGCGCCGTTTAAACT<br>TTCATTTCTGCTCT |
| PB1 | ATTAATGCGATCGCT<br>TCAATGGTGGAACA | GGCGCCGTTTAAACA<br>GTCATAAAGAGATT |
| PB2 | GCGCGTGCGATCGCA<br>TGGAGAGAATAAAA | AGCGCCGTTTAAACA<br>TTGATGGCCATCCG |
| NA | ATACATGCGATCGCA<br>TGAATCCAAACCAA | AGCGCCGTTTAAACT<br>TACTTGTCAATGGT |
| HA | ATACATGCGATCGCA<br>TGAAGGCAATACTA | GGCGCCGTTTAAACA<br>ATACATATTCTACA |

2.1 Materials and Methods

The cDNAs of H1N1 were kindly provided by Prof. BJ Zheng of University of Hong Kong. The restriction enzymes were obtained from Fermentas Corp. and were dissolved in the buffer supplied by the manufacturer. X-gal and IPTG were purchased from Solarbio Corp. (Solarbio Corp., Sigma Chemical Co.). All other enzymes and reagents used in this study were described previously. Hela cells were obtained from Institute of Biochemistry and Cell Biology, SIBS, CAS. Taq DNA polymerase, T4 DNA ligase and pMD19-T vector were purchased from Takara Co., Ltd. The psiCHECK™-2 Vector was purchased from Promega Corporation.

Amplification of Influenza Genes.

The cDNA of H1N1 was used as the template with primer sequences employed in the amplification designed with Primer 5.0 software. The primers were synthesized by Generay Biotechnology (Shanghai, China) and their sequences are shown in Table 1. Underlines were the SgfI site and PmeI site, respectively. The polymerase chain reaction (PCR) was carried out on a MG96+/LongGene Peltier Thermal Cycler (Hangzhou, China). NS, PB1 and M used the following PCR parameters 94° C. for 4 min followed by 35 cycles of 94° C. for 20 s, 58° C. for 30 s and 72° C. for 2 min, with a final extension step at 72° C. for 10 min. NP and NA used the following PCR parameters: 94° C. for 4 min followed by 35 cycles of 94° C. for 20 s, 54° C. for 30 s and 72° C. for 2 min, with a final extension step at 72° C. for 10 min. PB2 used the following PCR parameters: 94° C. for 4 min followed by 35 cycles of 94° C. for 20 s, 59° C. for 30 s and 72° C. for 2 min, with a final extension step at 72° C. for 10 min. HA used the following PCR parameters: 94° C. for 4 min followed by 35 cycles of 94° C. for 20 s, 57° C. for 30 s and 72° C. for 1.5 min, with a final extension step at 72° C. for 10 min.

Generation of Recombinant Vectors

The PCR products were separated on 1.5% (w/v) agarose gels. The relevant bands were extracted and recovered from the agarose gels using a UNIQ-10 DNA gel extraction kit (Shanghai Sangon Biological Engineering Technology and Service Co. Ltd, China). The purified gene fragments were inserted into the pMD19-T vector (Takara, Japan) according to the manufacturer's instructions. The recombinant T vectors were digested with restriction enzymes SgfI and PmeI. The relevant bands were extracted and recovered from the agarose gels using a UNIQ-10 DNA gel extraction kit (Shanghai Sangon Biological Engineering Technology and Service Co. Ltd, China). The purified gene fragments and the psiCHECK-2 vevtor was digested with the restriction enzymes SgfI and PmeI ligated at 16° C. with T4 DNA ligase. The vector was transformed into competent *E. coli* DH5a using a CaCl2 method and then transformed clones were selected on agar plates containing Amp+. The positive recombinant clones were confirmed by colony PCR and restriction enzyme digestion. The sequences of the inserted fragments were confirmed by digestion with SgfI and PmeI.

Cell Culture and Transfection Conditions

Hela cells were cultured on RPMI 1640 (HyClone) supplemented with 10% fetal bovine serum, 50 units/mL penicillin, and 50 Ag/mL streptomycin (HyClone). Cells were incubated in a humidified 5% CO2 atmosphere at 37° C. Cell transfection was performed with the plasmid (0.04 ug/50 ul medium) and siRNA (0.02 nM, 0.1 nM, 0.5 nM, 2.5 nM, 12.5 nM and 62.5 nM) using Lipofectamine 2000 (Invitrogen). The complexes of plasmids and Lipofectamine 2000 or siRNA and Lipofectamine 2000 were prepared according to the manufacturer's protocols. The solution of Lipofectamine 2000 was added dropwise to the solution of plasmid DNA or the solution of siRNA. 4-5 h later, the medium was replaced with RPMI 1640 medium containing 10% fetal bovine serum, and the cells were incubated for another 12 h.

Analysis of Luciferase Activity

For analysis of Luciferase activity, Hela cells were seeded in 96-well culture dishes (5000 cells each well) 12 h before transfection and transfected with recombinant vectors and siRNAs, every group had three repeats. Luciferase was measured using the Dual Luciferase Kit (Promega, Madison, Wis.) following manufacturer's instructions and read in a luminometer (Promega, Madison, Wis.). In this assay, the activities of *Photinus pyralis* and *Renilla reniformis* Luciferases are measured sequentially from a single sample. The firefly reporter is measured first by adding Luciferase Assay Reagent II to generate a luminescent signal. After quantifying the firefly luminescence, this reaction is quenched, and the *Renilla* Luciferase reaction is simultaneously initiated by adding Stop & Glo® Reagent to the same tube.

2.2. Results

Amplification of H1N1 Gene Sequences with PCR

Figure 5:
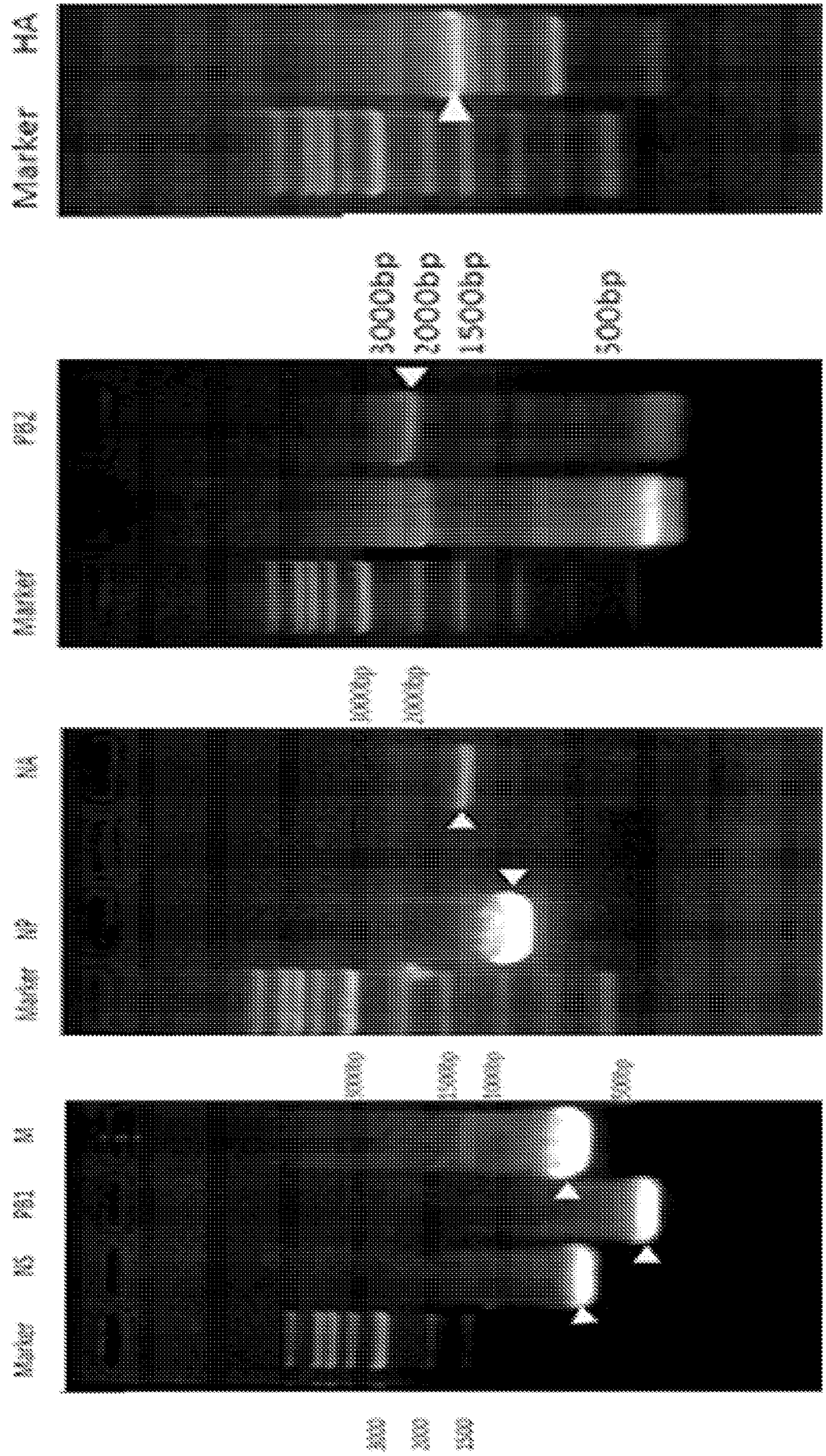
FIG. 5. Identification of PCR amplification from cDNA of H1N1. A: the influenza genes NS, PB1 and M respectively; B: the influenza genes NP and NA respectively; C, the influenza gene PB2; D, the influenza gene HA FIG. 6. Identification of the TA cloning inserts with SgfI and PmeI Digestions. The subcloned inserts have been demonstrated with gel electrophoresis assay: A, identification of NS gene; B, identification of PB1 gene; C, identification of M gene; D, identification of NP gene; E, identification of NA and HA genes; and F, identification of PB2 gene.

In order to amplify the influenza genes NS, PB1, M, NP, NA, PB2 and HA from the cDNA of H1N1, we designed the specific primer pairs (Table 1) for each of those gene sequences with the SgfI and PmeI restriction sites in either forward primers or reverse primers. Specific NS gene (~650 bp), PB1 gene (~350 bp) and M gene (~750 bp) sequences have been amplified (FIG. 5A); Specific NP gene (~1020 bp) and NA gene (~1400 bp) sequences have been amplified (FIG. 5B); Specific PB2 gene (~2270 bp) sequence has been amplified (FIG. 5C); Specific HA gene (~1700 bp) sequence had been amplified (FIG. 5D).

TA Cloning Obtained the Specific Subclones

Figure 6:
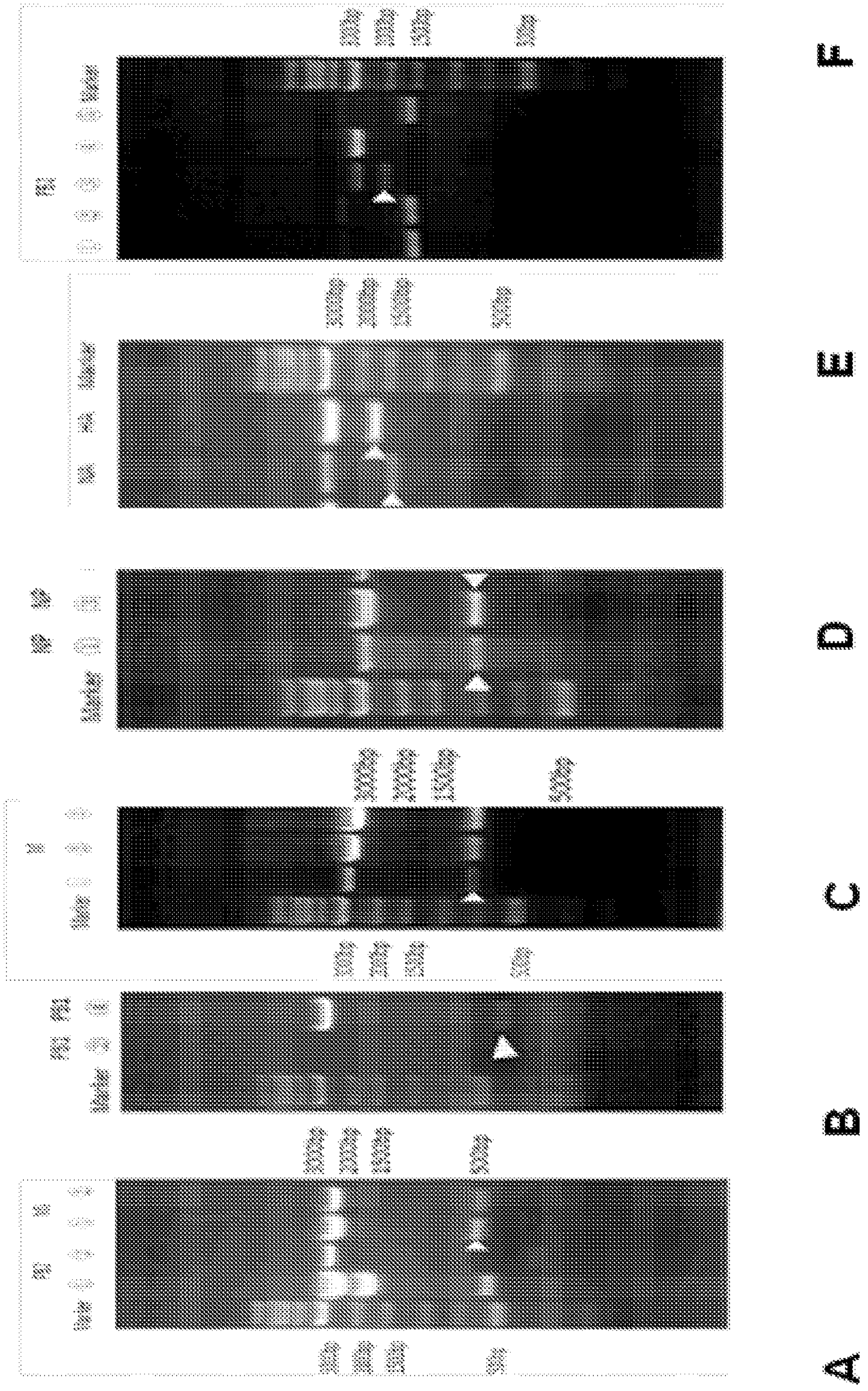

In order to identify whether the genes of interest have been subcloned, we performed the TA cloning with the amplified DNA fragments purified from the PCR products. After inserting the DNA fragments into the T vector, we digested the plasmids using restriction enzymes SgfI and PmeI and resulted in successful subclones with NS inserts about 2.7 kb and 650 bp respectively (FIG. 6A); PB1 inserts about 2.7 kb and 350 bp respectively (FIG. 6B); M inserts about 2.7 kb and 750 bp respectively (FIG. 6C); NP inserts about 2.7 kb and 1020 bp respectively (FIG. 6D); NA inserts about 2.7 kb and 1400 bp respectively (FIG. 6E); HA inserts about 2.7 kb and 1700 bp respectively (FIG. 6E); PB2 inserts about 2.7 kb and 2270 bp respectively (FIG. 6F), as expected. With sequencing and aligning analyses, the subcloned influenza gene sequences NS, PB1, M, NP, NA, PB2 and HA were confirmed.

Construction of the Recombinant Luciferase Vectors

Figure 7:
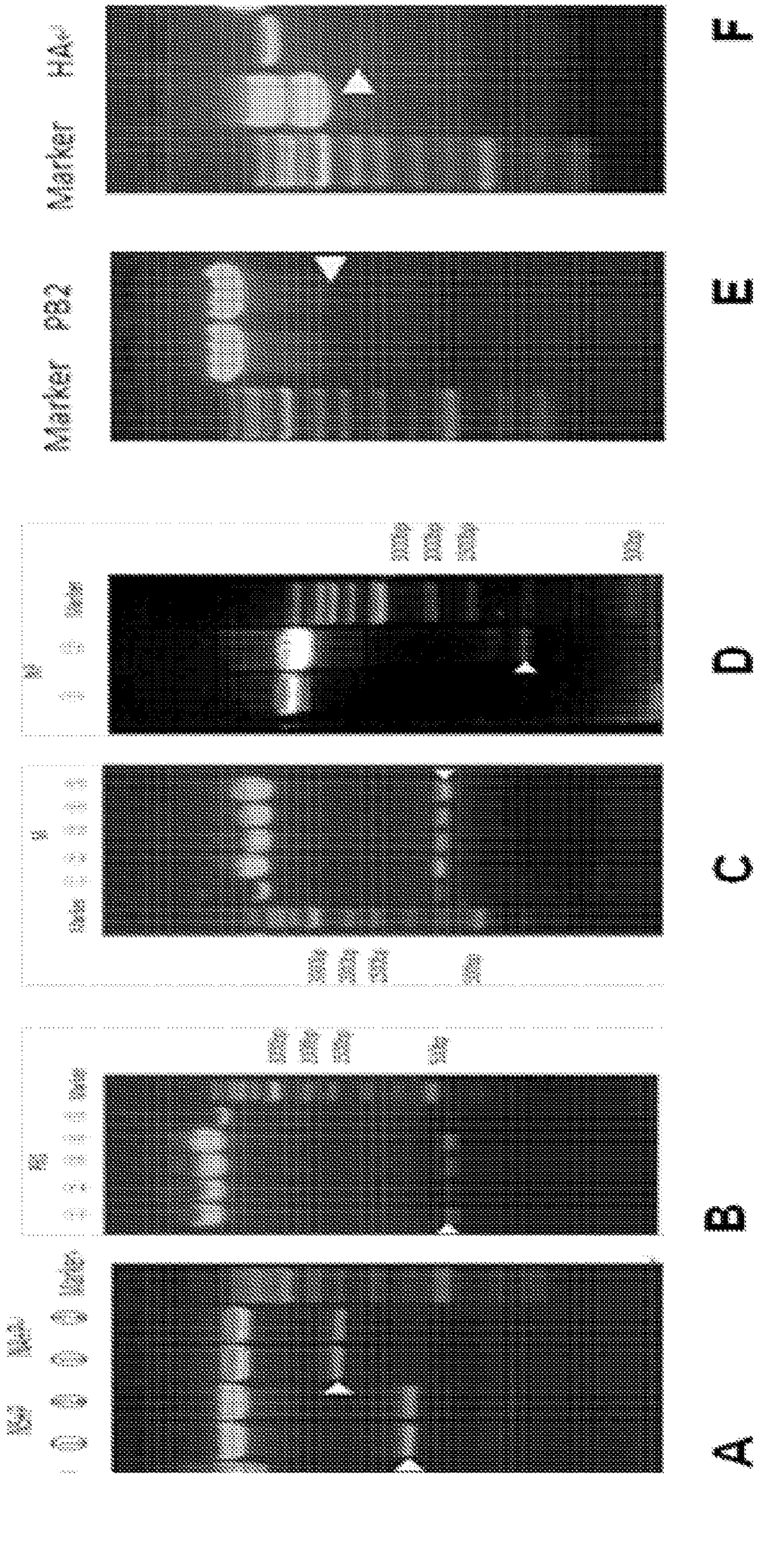
FIG. 7. Identification of influenza gene fragments after inserting the psiCHECK-2 vector with SgfI and PmeI double digestion. A, identification of NS and NA genes; B, identification of PB1 gene; C, identification of M gene; D, identification of NP gene; E, identification of PB2 gene; F, identification of HA gene.

Influenza gene fragments were inserted into the vector psiCHECK-2 efficiently. Digestions of these plasmids with SgfI and PmeI have confirmed that all plasmids contain two inserted DNA fragments. The NS inserts into psiCHECK-2 vector is about 6.3 kb and 650 bp respectively (FIG. 7A); The PB1 inserts into psiCHECK-2 vector is about 6.3 kb and 350 bp respectively (FIG. 7B); The M inserts into psiCHECK-2 vector is about 6.3 kb and 750 bp respectively (FIG. 7C); The NP inserts into psiCHECK-2 vector is about 6.3 kb and 1020 bp respectively (FIG. 7D); The NA inserts into psiCHECK-2 vector is about 6.3 kb and 1400 bp respectively (FIG. 7E); The HA inserts into psiCHECK-2 vector is about 6.3 kb and 1700 bp respectively (FIG. 7F), as expected. These results suggest that the recombinant Luciferase vectors psi-NS, psi-PB1, psi-M, psi-NP, psi-NA, psi-HA and psi-PB2 have been constructed.

Figure 8:
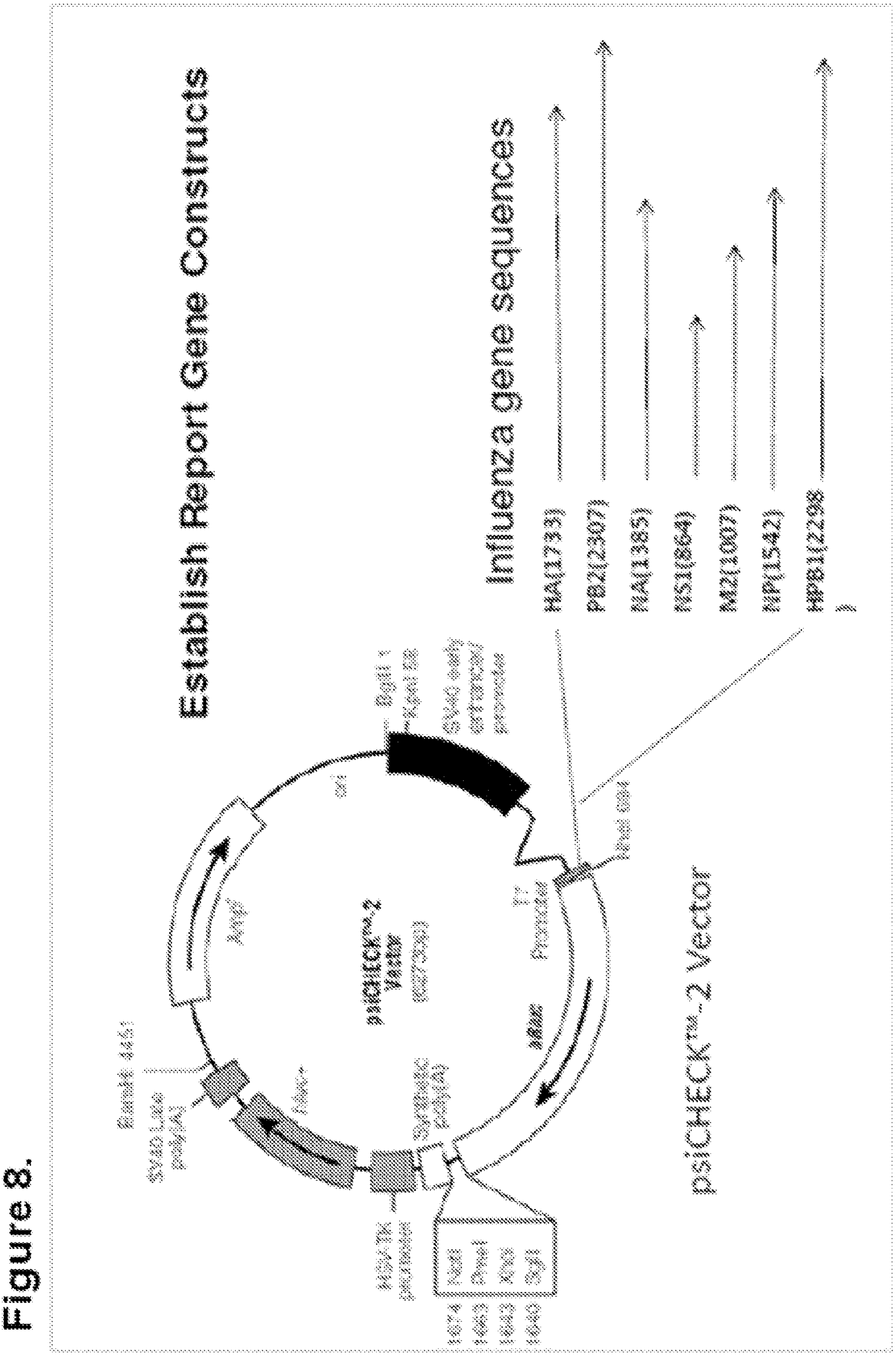
FIG. 8. A Plasmid expression vector for subcloning of influenza virus genes has been used for evaluation of siRNA-mediated gene silencing in cell culture.

After inserting the psiCHECK-2 vector with other gene sequences, the gel electroporation assay was applied for evaluation of the correct insertions. FIG. 8. indicated that using SgfI and PmeI double digestion is able to identify the right sequences were subcloned into the vector. A, identification of NS and NA genes; B, identification of PB1 gene; C, identification of M gene; D, identification of NP gene; E, identification of PB2 gene; F, identification of HA gene. FIG. 8. illustrates the structure and cloning site for insertion of influenza viral gene sequences. The correct restriction enzymes can be used for characterization of the insertion and subcloning.

Figure 9:
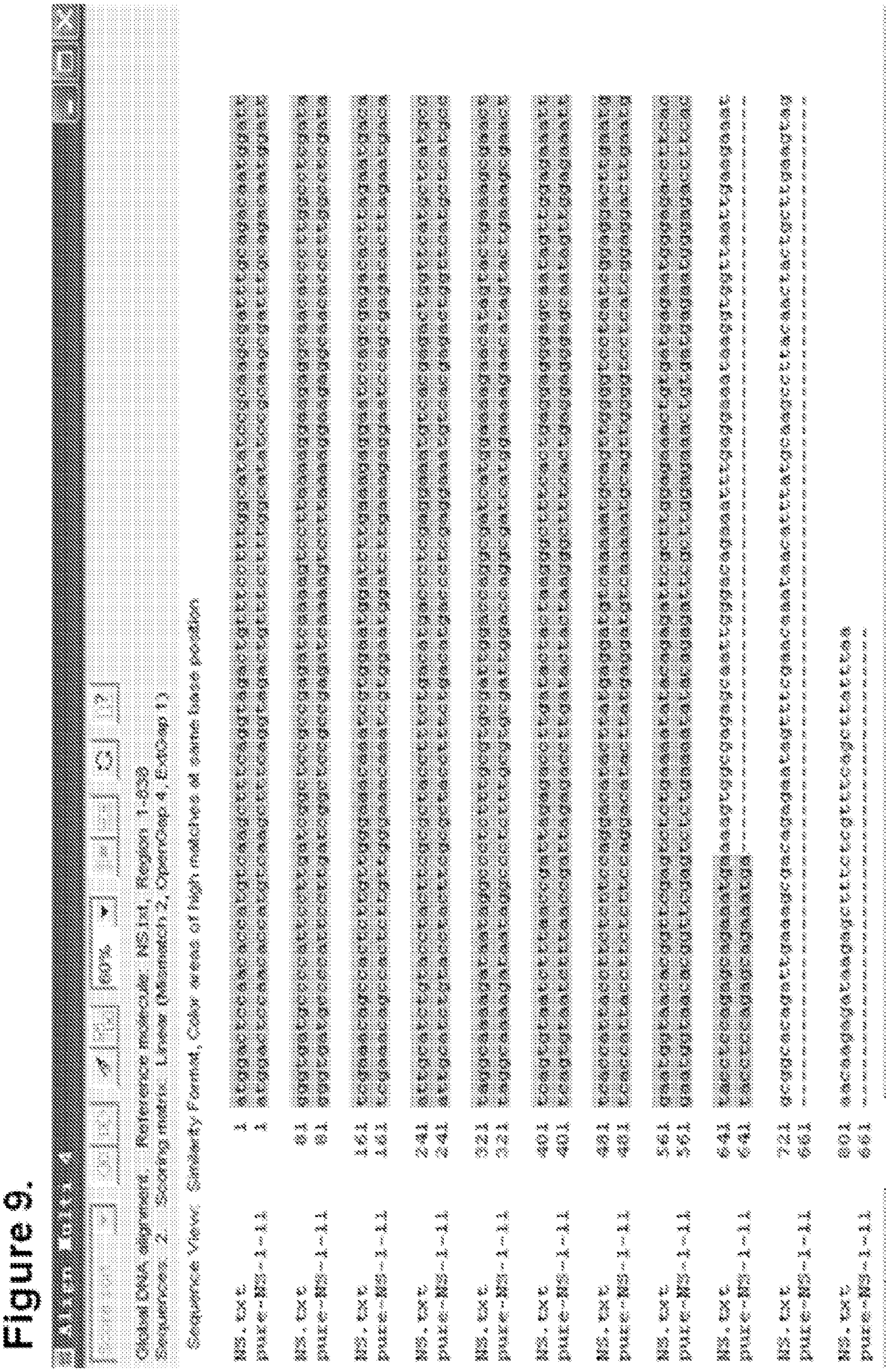
FIG. 9. The NS gene alignment of the subcloning sequence (SEQ ID NO: 76) with target gene sequence (SEQ ID NO: 75) was highlighted using blue marker.
Figure 10:
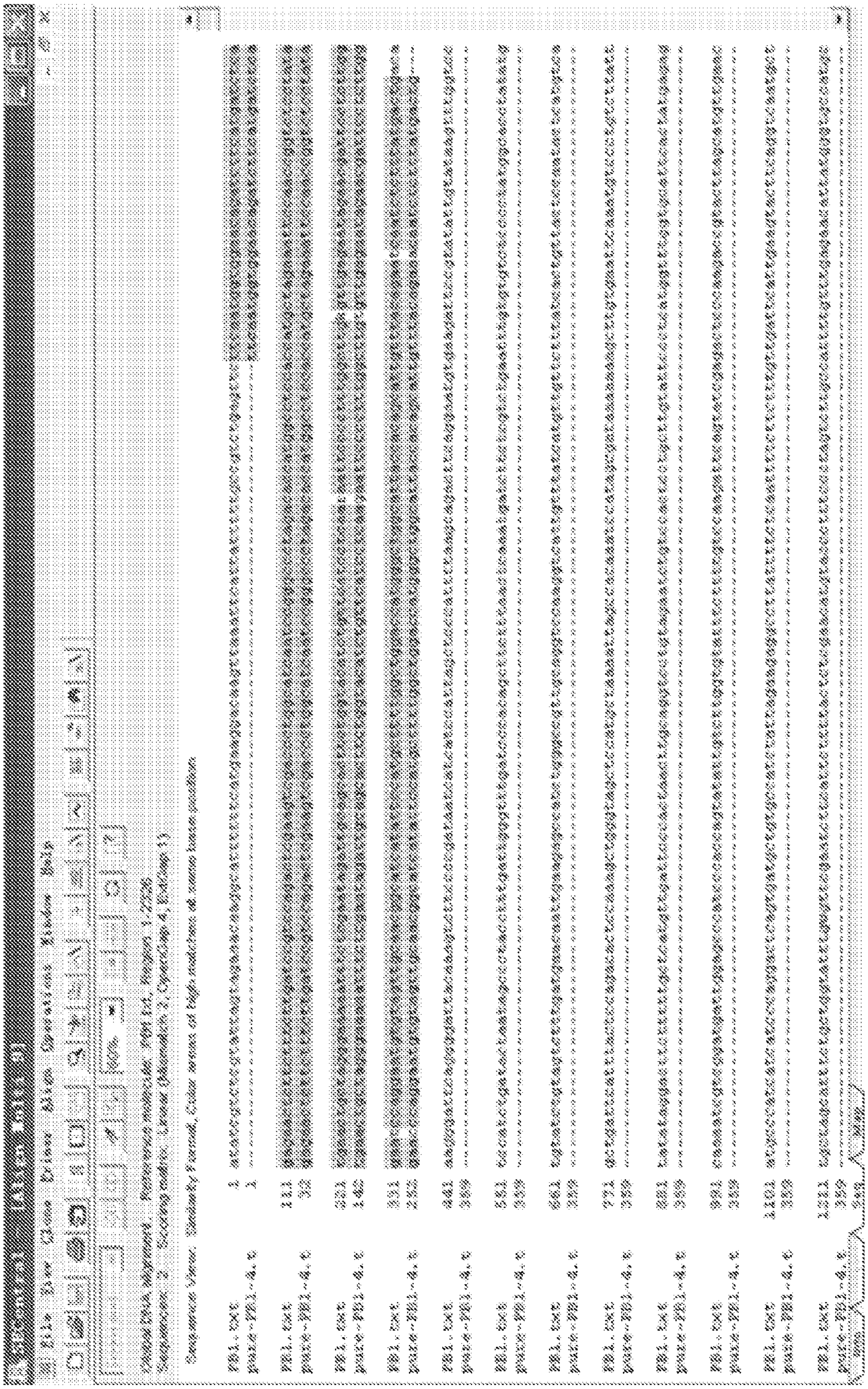
FIG. 10. The PB1 gene alignment of the subcloning sequence (SEQ ID NO: 78) with target gene sequence (SEQ ID NO: 77) was highlighted using blue marker.
Figure 11:
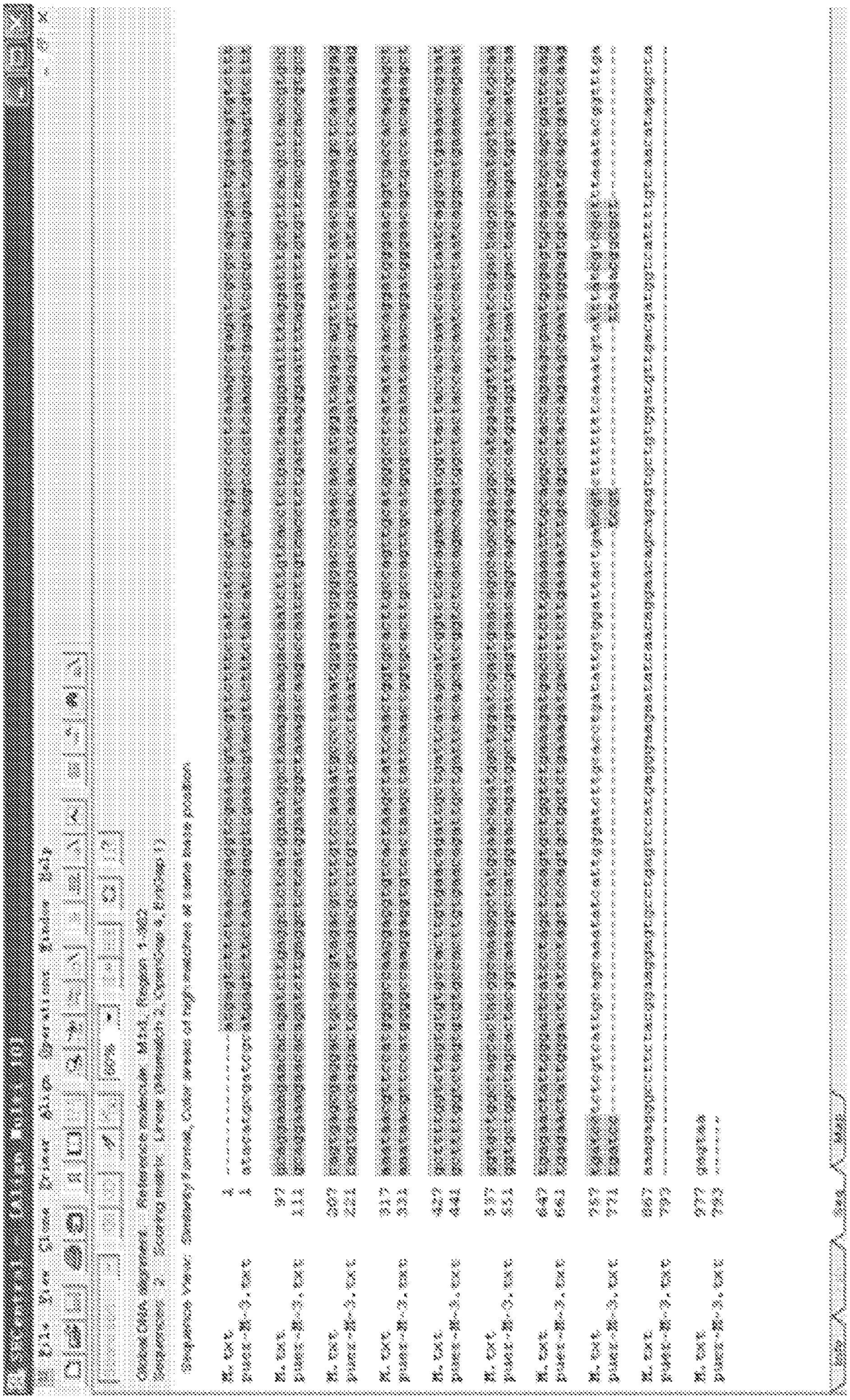
FIG. 11. The M gene alignment of the subcloning sequence (SEQ ID NO: 80) with target gene sequence (SEQ ID NO: 79) was highlighted using blue marker.
Figure 12:
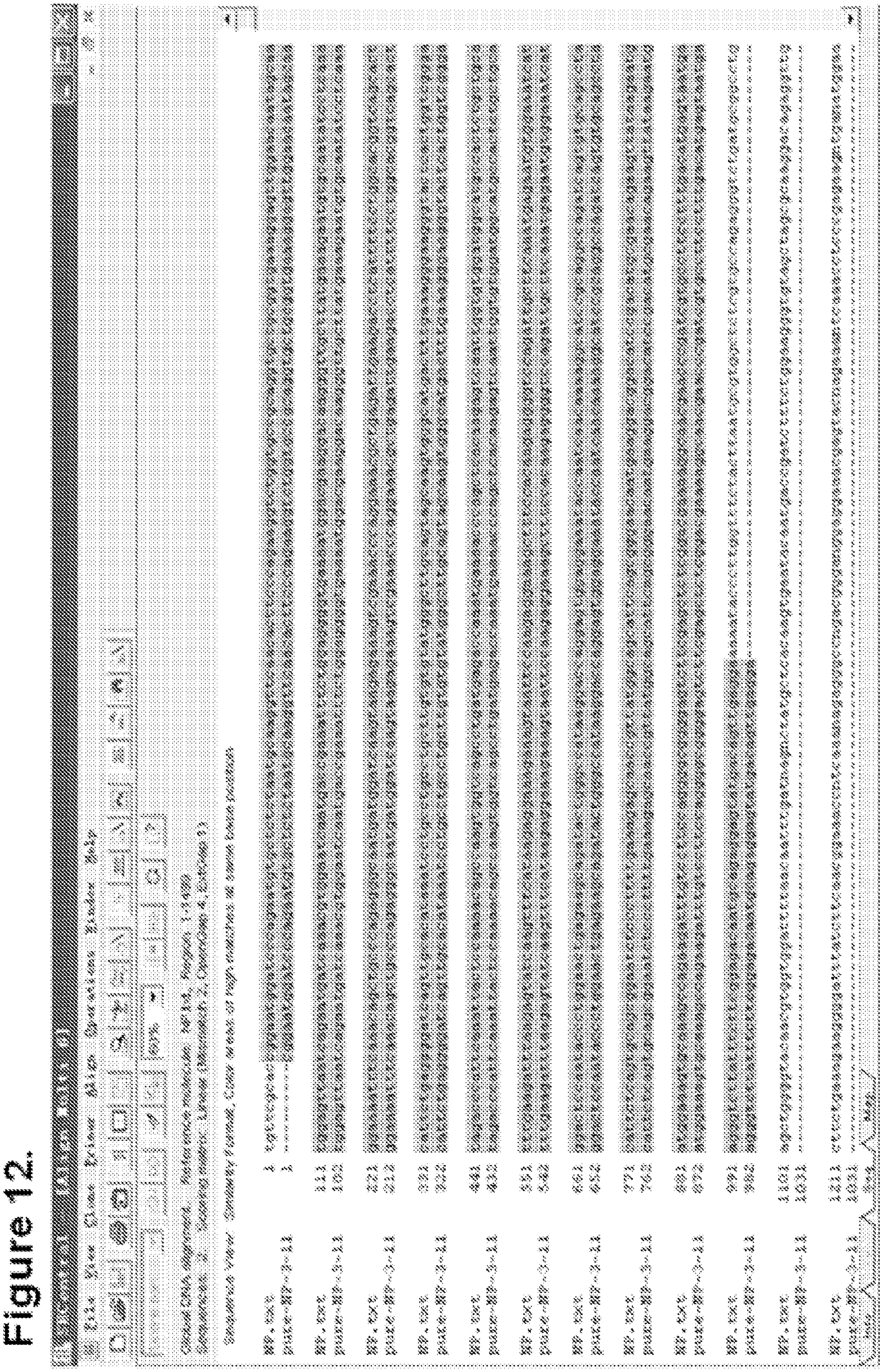
FIG. 12. The NP gene alignment of the subcloning sequence (SEQ ID NO: 82) with target gene sequence (SEQ ID NO: 81) was highlighted using blue marker.
Figure 13:
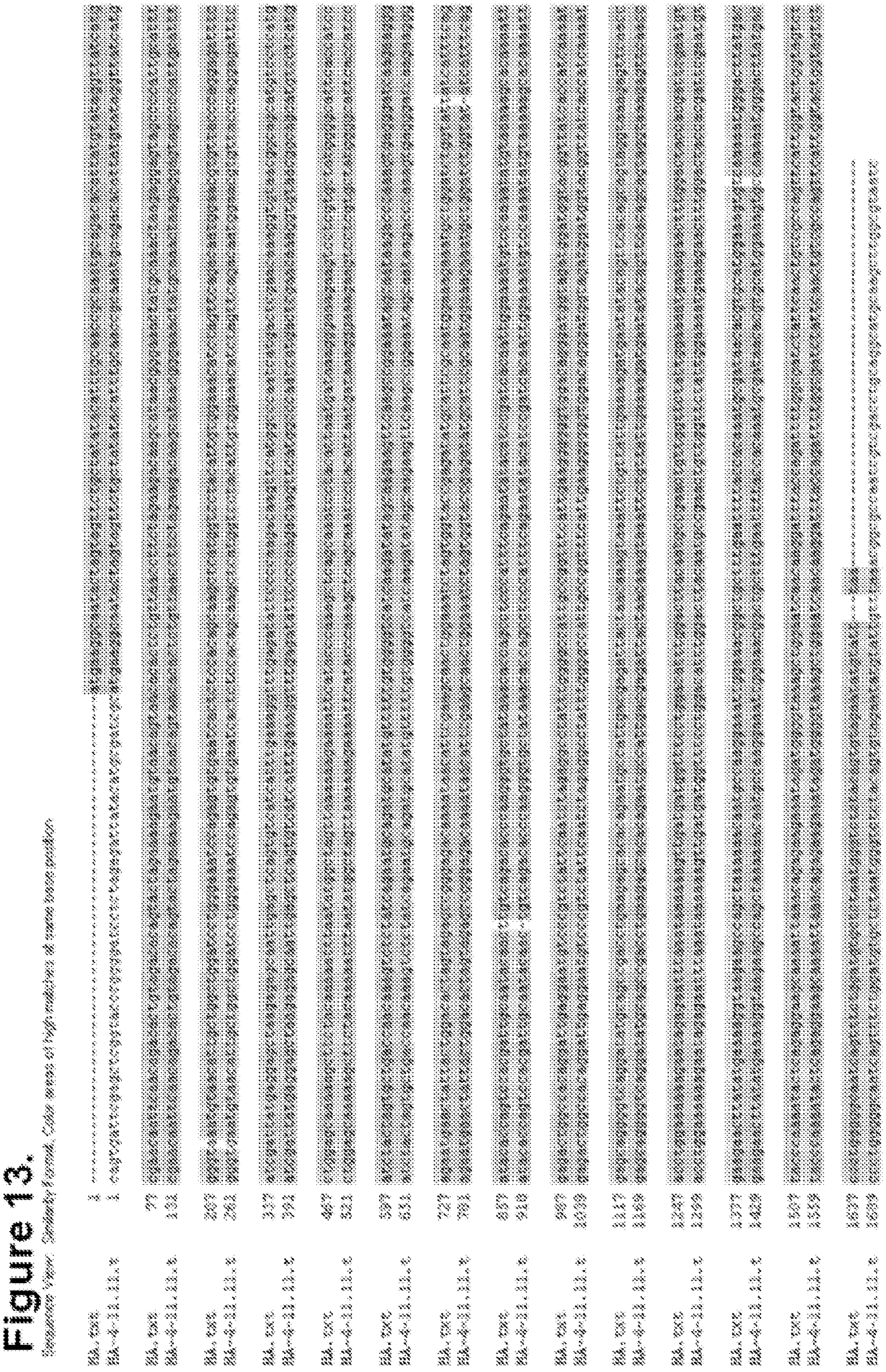
FIG. 13. The NA gene alignment of the subcloning sequence (SEQ ID NO: 84) with target gene sequence (SEQ ID NO: 83) was highlighted using blue marker.

Five Figures (from 9 to 13) were used to demonstrate that correct sequence alignments of the subcloning sequences covering NS (FIG. 9), PB1 (FIG. 10), M (FIG. 11), NP (FIG. 12) and NA (FIG. 13) genes.

Screening the Potent siRNAs by Dual-Luciferase Reporter Assay System

Figure 14:
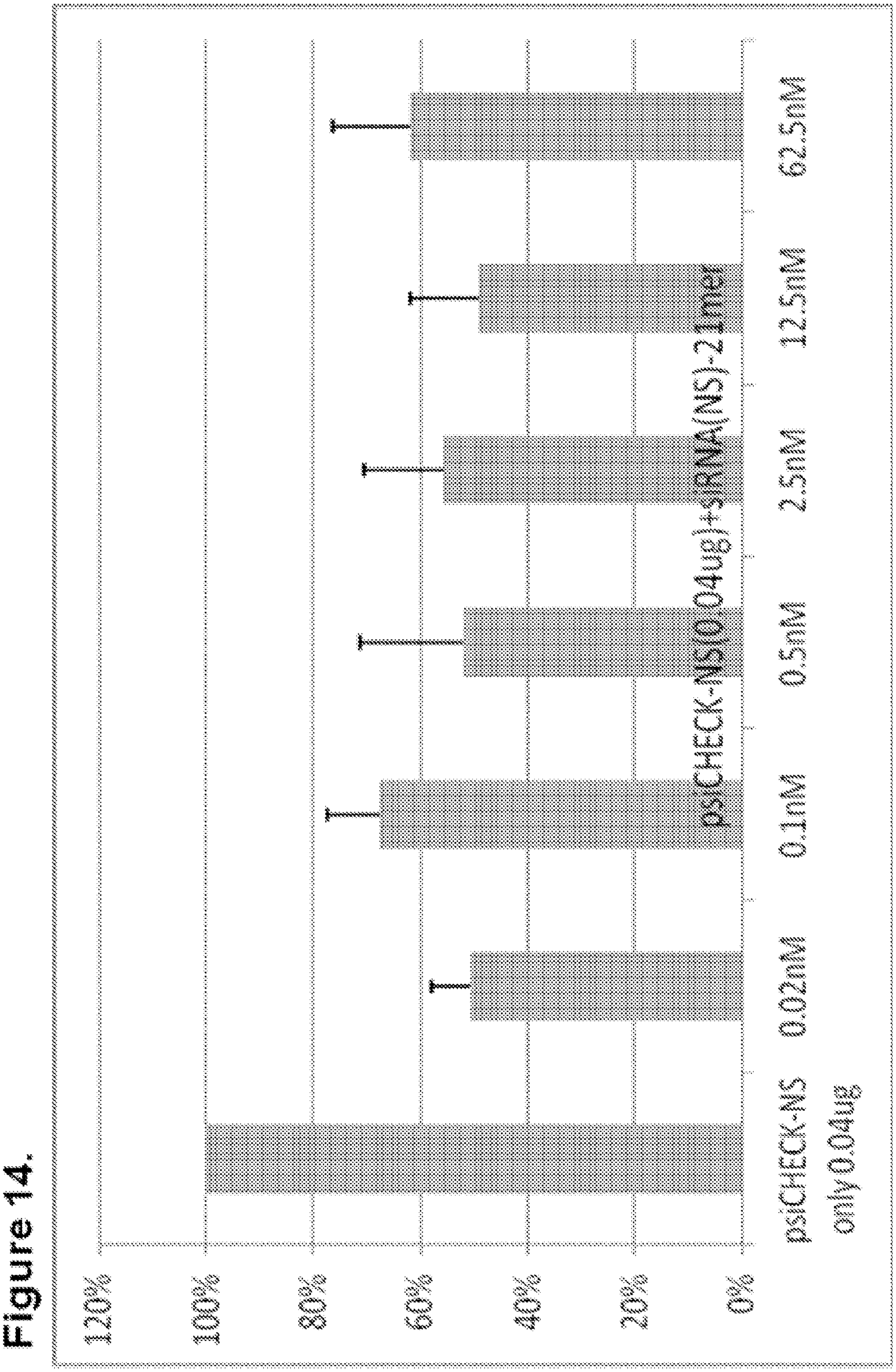
FIG. 14. Inhibition of NS expression after treatment with siRNA-21mer (HeLa cell culture). IC50(siRNA-NS-21 mer) =0.85 nM.
Figure 15:
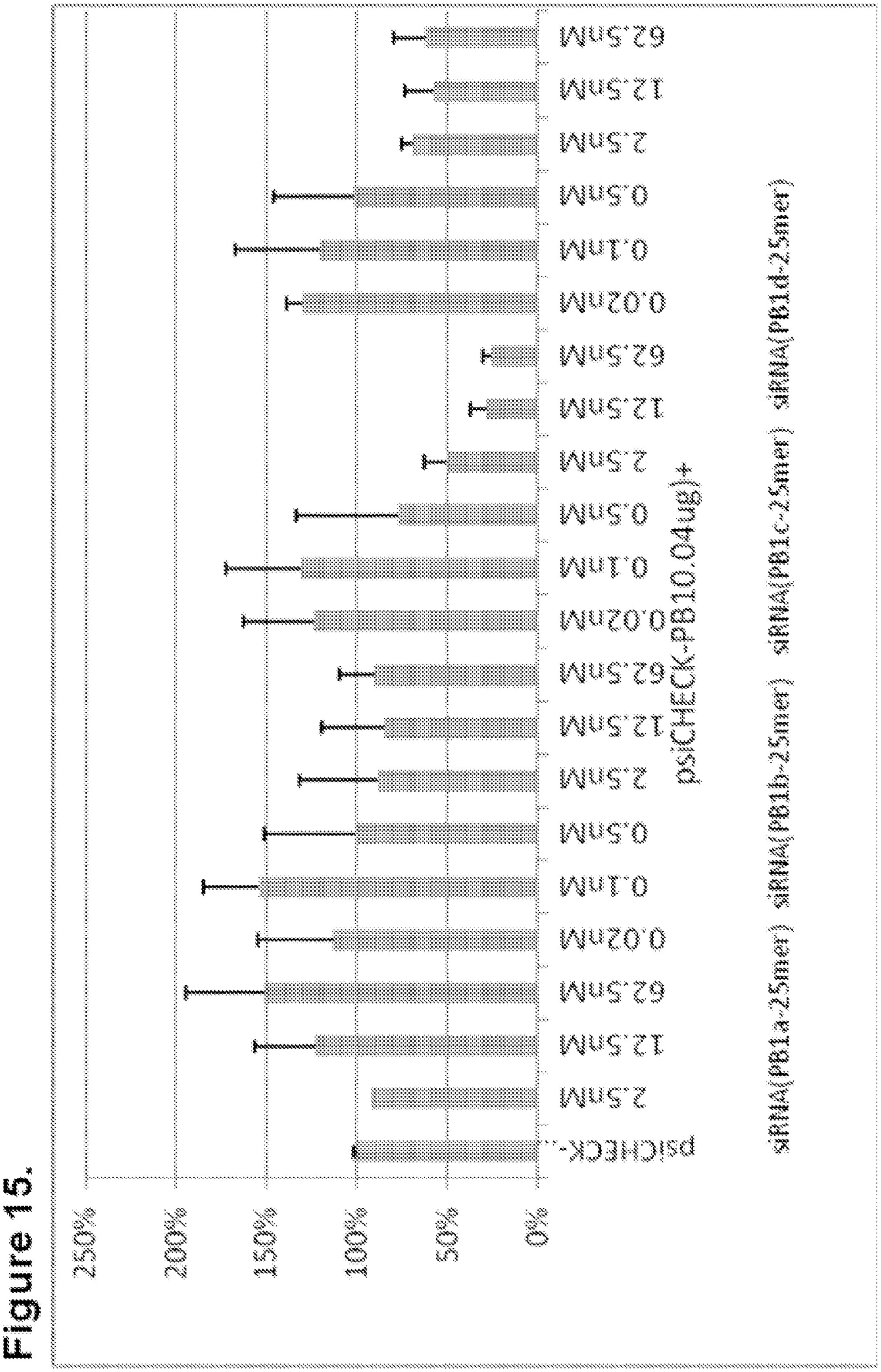
FIG. 15. Inhibition of PB1 expression after treatment with siRNA-25mer (HeLa cells). IC50(siRNA-PB1-25mer)=2.5 nM.
Figure 16:
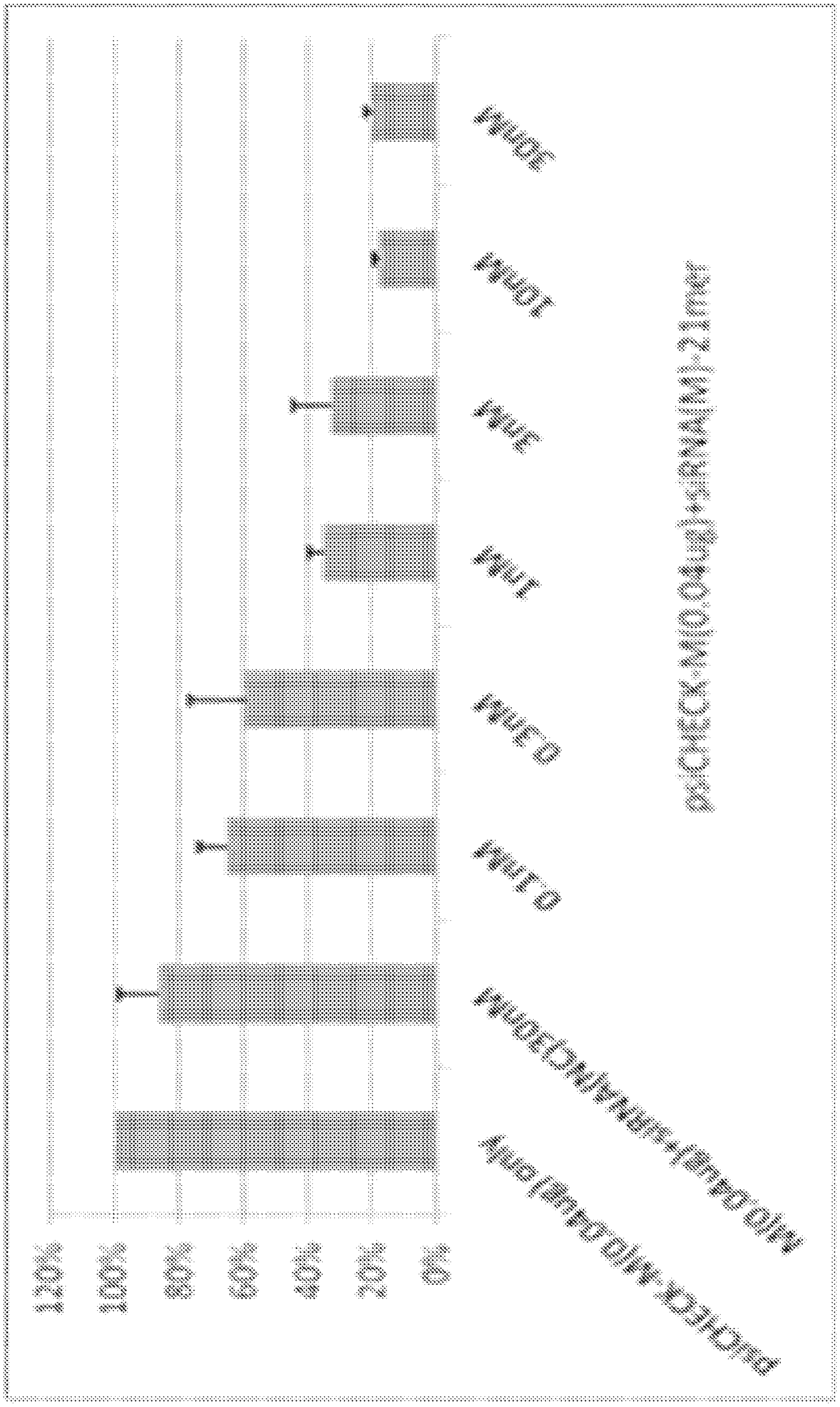
FIG. 16. Inhibition of M expression after treatment with siRNA-21 mer (HeLa cells). IC50(siRNA-M-21mer)=1.28 nM.
Figure 17:
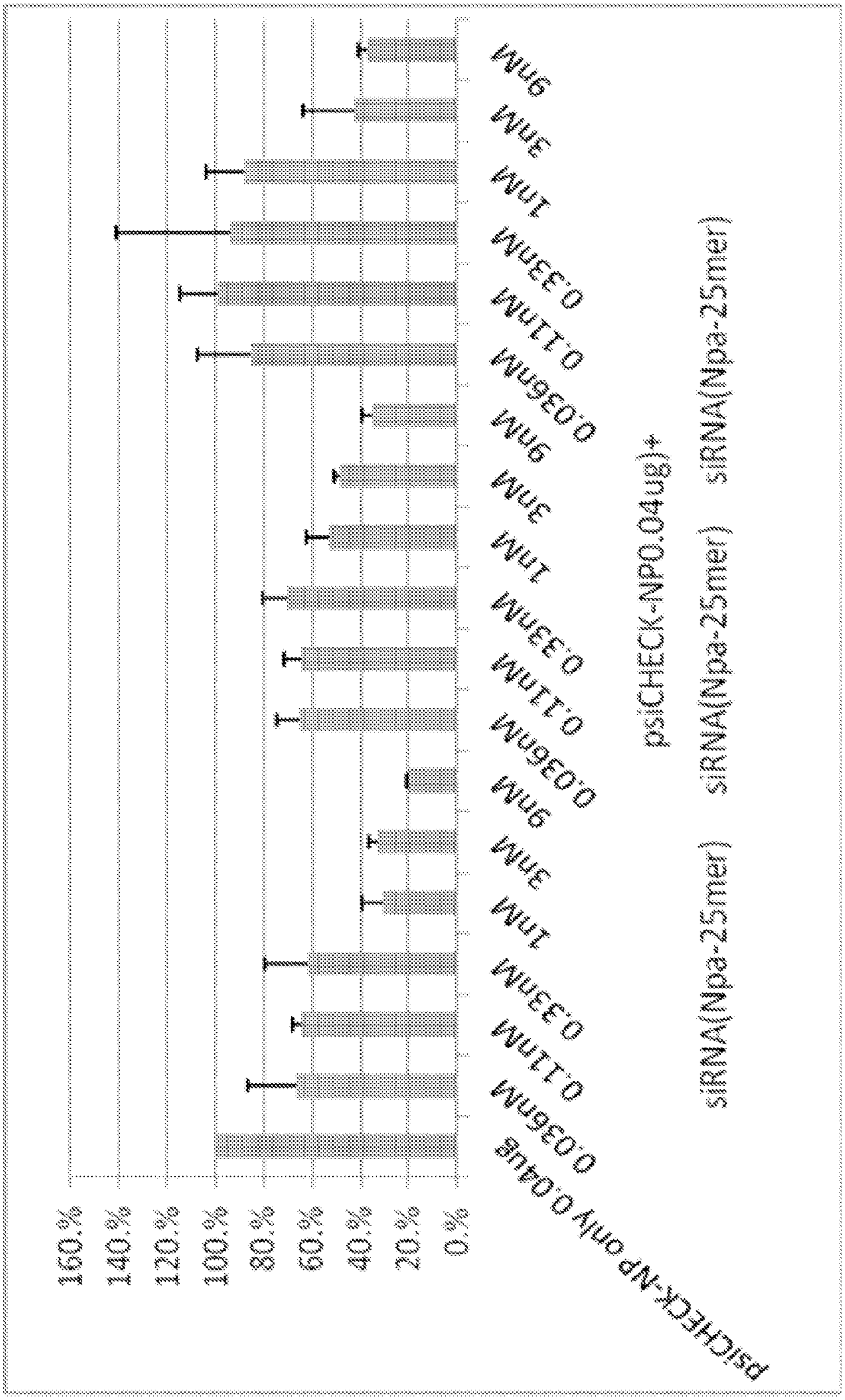
FIG. 17. Inhibition of NP expression after treatment with candidate siRNA-25mer (HeLa cells). IC50(siRNA-Npa-25mer)=0.38 nM; IC50(siRNA-NPb-25mer)=1.26 nM; IC50(siRNA-NPc-25mer)=2.67 nM.

We investigated whether the siRNAs designed could knock down the target genes by dual-Luciferase assay system. Co-transfection of siRNAs and recombinant Luciferase vectors in Hela cells was performed to examine the changes in Luciferase activities. Down regulation of the Luciferase expression was observed when the psicheck-2 vectors containing the NS gene fragment and a selected siRNA-NS were co-transfected in Hela cells (FIG. 14). The results showed that IC50 of the siRNA-NS for silencing NS sequence-mediated Luciferase expression in Hela cells was approximately 0.8 nM. Similarly, the decrease in Luciferase activity was slightly or significantly prevented with siRNA-M-21 mer, siRNA-Npa-25mer, siRNA-NPb-25mer, siRNA-NPc-25mer, siRNA-NP-21 mer, siRNA-Me-25mer, siRNA-PB1b-25mer, siRNA-PB1c-25mer and siRNA-PB1d-25mer, and IC50 of them on Hela cells were approximately 1.28 nM, 0.38 nM, 1.26 nM, 2.67 nM, 12.79, 0.04 nM, 100 nM, 2.56 nM and 20 nM (FIG. 15.). The results indicated that the siRNA-Me-25mer exhibits better knockdown of the target gene than siRNA-M-21 mer (FIG. 16). The effects of siRNAs-NP-25mers are better than siRNA-NP-21 mer, while the siRNA-Npa-25mer was the best one among siRNAs-NP-25mer (FIG. 17).

The viral nucleic acid drug screening needs strict laboratory conditions. We successfully constructed the influenza viral gene dual-Luciferase repoter vectors psi-NS, psi-PB1, psi-M, psi-NP, psi-NA, psi-HA and psi-PB2, so that we can screen the drugs against viruses in an ordinary laboratory. The results indicated that the effects siRNA-25mer inhibitors are seemingly better than siRNA-21 mer inhibitors.

Example 3. Using H1N1 Challenged MDCK Cells to Identify Potent siRNA Inhibitors (25Mer) by Q-RT-PCR Sixteen siRNA Oligos were Tested The siRNA sequences are 25 mer in length and listed in Table 2., were ordered from Qiagen (Germantown, Md.) covering multiple key genes of influenza A (H1N1). Table discloses SEQ ID NOS 32, 1, 33-37, 2, and 38-45, respectively, in order of appearance.

| | |
|---|---|
| M2a | **5'-GCCCAGUGAGCGAGGACUGCAGCGU-3'** |
| M2b | 5'-GAGCGAGGACUGCAGCGUAGACGCU-3' |
| M2c | 5'-GAUUCACAGCAUCGGUCUCACAGAC-3' |
| M2d | 5'-CGAAUGGGAGUGCAGAUGCAGCGAU-3' |
| M2e | 5'-CAGAUGCAGCGAUUCAAGUGAUCCU-3' |
| NPa | 5'-AUGGCGUCUCAAGGCACCAAACGAU-3' |
| NPb | 5'-AAUGAUGCCACAUAUCAGAGAACAA-3' |
| NPc | 5'-GUGUGGAUGGCAUGCCACUCUGCTG-3' |
| PAa | 5'-CCAAUGAUCGUCGAGCUUGCGGAAA-3' |
| PAb | 5'-CUUGCCGACCAAAGUCUCCCACCGA-3' |
| PAc | 5'-CCACCGAACUUCUCCAGCCUUGAAA-3' |
| PAd | 5'-GAGAGCAUGAUUGAGGCCGAGUCUU-3' |
| PB1a | 5'-GGCUUUCCUUGAAGAAUCCCACCCA-3' |
| PB1b | 5'-GAUGCCGUUGGAAUAUGAUGCCGUU-3' |
| PB1c | 5'-GGGGAAUUCUUGAGGAUGAACAGAU-3' |
| PB1d | 5'-GCAUGGUGGAGGCCAUGGUGUCUAG-3' |

Cell Lines and Viruses Used in the Experiments

MDCK was maintained in MEM or DMEM (Invitrogen, USA) supplemented with 10% heat-inactivated fetal bovine serum_(FBS) and antibiotics (100 U penicillin G/mL and 100 μg streptomycin/mL). Influenza virus strain A/New Caledonia/_20/1999 (H1N1) used in the experiment was prepared in MDCK cells and virus titers were determined by TCID50. All experiments with H1N1 virus were performed in BSL-3 laboratory. The siRNAs were reverse transfected to MDCK cells using Lipofectamine™ RNAiMAX (Invitrogene, USA) as described in the company's instruction. After incubating the cells for 16, 18 hrs, the cells were infected with the viruses and followed by detection of viral replication. 24 hours after infection, RNA were extracted from the cells and followed by real time RT-PCR to detect the relative quantities of replicated viral RNA.

Real-time RT-PCR

Figure 18:
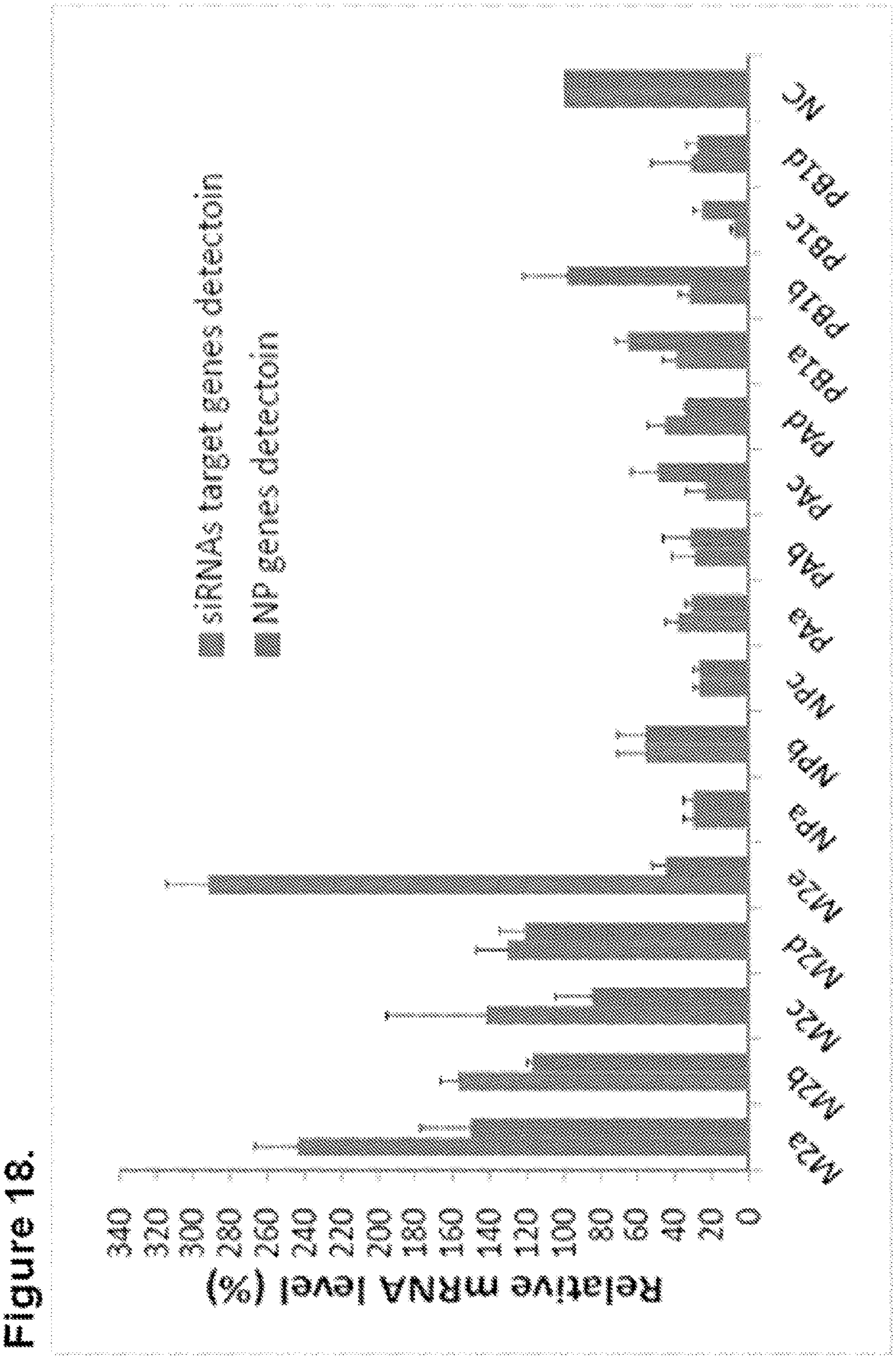
FIG. 18. Measurement of siRNA-mediated inhibition of H1N1 virus was conducted in MDCK cell culture using viral RNA quantification by Q-RT-PCR.

Real-time RT-PCR was carried out as described previously [39]. Briefly, H1N1 infected MDCK and Mock MDCK were harvest at 24 hr after infection. Total RNA was extracted from the infected cell samples using RNeasy RNA isolation Kit (Qiagen, Germany) and reverse transcribed using Superscript II Reverse Transcriptase and Oligo dT primer (Invitrogene, USA), according to the manufacturer's protocol. Viral mRNA copies were measured by SYBR green M63000 Real-Time PCR System (Stratagene, USA), using primers NP-Forward: 59-GAC CAG GAG TGG AGG AAA CA-39 (SEQ ID NO: 46), NP-Reverse: 59-CGG CCA TAA TGG TCA CTC TT-39 (SEQ ID NO: 47); M2-Forward: 59-CGT CGC TTT AAA TAC GGT TTG-39 (SEQ ID NO: 48), M2-Reverse: 59-CGT CAA CAT CCA CAG CAT TC-39 (SEQ ID NO: 49), b-Actin-Forward: 59-CGT ACC ACT GGC ATC GTG AT-39 (SEQ ID NO: 50), b-Actin-Reverse: 59-GTG TTG GCG TAC AGG TCT TTG-39 (SEQ ID NO: 51). The reactions were performed at 95° C. 10 mins, 40 cycles of 95° C. 1 min, 60° C. 1 min, 72° C. 1 min, followed by melting curve analysis according to instrument documentation (Stratagene M63000). All reactions were done in triplicates and the results were normalized by b-action. FIG. 18 demonstrated the viral copies measured by Q-RT-PCR after transfections of all sixteen siRNA oligos into the H1N1 challenged MDCK cells. The blue bars indicate the knockdown of the target genes with different siRNA duplexes, such as M2a, M2b, M2c, M2d and M2e which correspond to regions within the M2 gene. The Y axis represents the level of target gene knockdown. The red bars indicate the virus NP gene changes after siRNA-mediated gene silencing. Since NP gene is responsible for viral entry, replication and viral release, and NP gene expression has been used as an indicator for viral replication. In general, more than 50% of target gene silencing could be considered as an obvious inhibition. From the statistic analysis, we can see that the significant target gene silencing has been achieved with siRNA duplexes specific to NPa, NPc PAa, PAb, Pac, Pad, PB1a, PB1b, PB1c and PB1d sequences. In addition, all those gene silencing resulted in NP gene down regulation except PB and PB1b siRNAs. In summary, siRNA duplexes specific to NPa, NPc, PAa, PAb, PAc, Pac, PB1c and PB have resulted in strong gene silencing and inhibition of viral replication. The above results can be verified with Western-Blotting and viral titer measurement.

Based on these results, we can determine at certain degree the potencies of some siRNA oligos for silencing the viral genes which may inhibit viral replication and infection. As indicated in FIG. 18, siRNA-NPa, siRNA-NPc, siRNA-PAa, siRNA-PAb, siRNA-PAc, siRNA-PB1c and siRNA-PB1d exhibited potent antiviral activities in the MDCK cell culture, based on the quantification of the viral RNA changes after H1N1 viral infection of the cell. However, the Q-RT-PCR results are only reflecting the changes of viral copy numbers or viral RNAs in the infected cells, in our case in the infected MDCK cells, but not the biological impacts of the viral infection. We next use the Cytopathic Effects (CPE) to evaluate the inhibition of viral killing of the infected cells using siRNA oligos.

Example 4. Evaluation of the Potencies of siRNA Oligos (25Mer) with H1N1 Challenged MDCK Cells Using CPE Assay and HA Protein Detection The same group of siRNA oligos as shown in Table 2 was tested in a different laboratory.

Cell Lines and Viruses Used in the Experiments

MDCK was maintained in MEM or DMEM (Invitrogen, USA) supplemented with 10% heat-inactivated fetal bovine serum_(FBS) and antibiotics (100 U penicillin G/mL and 100 μg streptomycin/mL). Influenza virus strain A/New Caledonia/_20/1999 (H1N1) used in these experiments was prepared in MDCK cells and virus titers_were determined by TCID50. All experiments with H1N1 virus were performed in BSL-3 laboratory.

Preparation and Transfection of siRNAs

The siRNAs targeting M, NP, or PA, or PB1 gene of H1N1 influenza virus (Table 2) were ordered from Qiagen. The siRNAs were reverse transfected to MDCK cells using Lipofectamine™ RNAiMAX (Invitrogen, USA) as described in company's instruction. After incubating the cells for 16'18 hrs, the cells were infected with the viruses and followed by detection of viral replication. 24 hours after infection, RNA were extracted from the cells and followed by real time RT-PCR to detect the relative quantities of replicated viral RNA.

Influenza Virus Infection and Viral Load Detection

MDCK cell line in 24-well plates was infected with viruses at moi of 0.005, 0.5 (2 mg/mL trypsin was used in the infection process of H1N1). After incubation for 1 hr, the infected medium was removed and MEM without FBS was added. Cell supernatants were collected at different time points. The viral load was detected by hemagglutination (HA) and/or plaque assays as described previously [39]. Briefly, the HA assay was carried out in U-bottom 96 well plates. Serial 2-fold dilutions of virus samples were mixed with an equal volume of a 0.5% suspension of turkey erythrocytes (Lampire Biologic Laboratories, Pipersville, USA) and incubated at room temperature (RT) for 45 mins. Wells containing an adherent, homogeneous layer of erythrocytes were scored as positive. For plaque assay, serial 10-fold dilutions of virus sample were added into a monolayer of MDCK cells. After 1 hr incubation, the virus was removed and the cultures were overlaid with 1% semi solid agar-MEM. Three days after infection, plaques were visualized by staining of crystal violent.

TABLE 3

Selected siRNA Oligos Showing Potent Anti-influenza H5N1 Activity

| siRNA uM | NP a | | NP c | | M2 b | | M2 d | |
|---|---|---|---|---|---|---|---|---|
| 400 | | | | | | | | |
| 200 | 2 | 4 | | | | | | |
| 100 | 8 | 8 | 0 | 0 | | | | |
| 50 | 16 | 16 | 16 | 16 | 0 | 8 | 4 | 8 |
| 25 | 16 | 16 | 32 | 32 | 0 | 32 | 8 | 8 |
| 12.5 | | | 16 | 32 | 32 | 32 | 16 | 16 |
| 6.25 | | | | | 16 | 32 | 16 | 16 |
| 3.125 | | | | | | | | |

The siRNA oligos were reverse transfected to MDCK cells using Lipofectamine™ RNAiMAX (Invitrogene, USA) as described in company's instruction. After incubated the cells for 16, 18 hrs, the cells were infected with the viruses and followed by detection of viral replication. The NPa-siRNA and NPc-siRNA have IC50 around 50-100 μM. The M2b-siRNA and M2d-siRNA have IC50 about 25 μM (see labels in Table 3). These observations are consistent with the other evaluations demonstrated in the FIG. 18.

Example 5. Evaluation of the Potencies of siRNA Oligos (21 Mer) with H1N1 Challenged MDCK Cells Using CPE Assay and HA Protein Detection A similar procedure was applied for evaluation of 36 siRNA oligos with homologues to PB1 and PA genes of influenza A virus for their antiviral activities with MDCK cell culture. The potent siRNA oligos (Table 4) were selected based on their IC50 for silencing PB1 and PA genes of influenza A virus (H1N1) resulting viral titer downregulation in the cell culture. Interestingly, PB1 siRNAs are more potent (IC50<12.5 μM) than PA siRNAs (IC50<25 μM), and all 8 siRNA oligos have exhibited potent anti-H1N1 activity with IC50<25 μM. Based on this study and the previous study with 25mer siRNA, we can see that the length of siRNA duplexes did not show significant difference regarding their antiviral activities. Therefore, in our future in vivo study, we will test both 21 mer and 25mer siRNA oligos for their antiviral potencies.

Cell Dissociation

Culture medium from 90% confluence MDCK culture was discarded. Cells were washed with 10 ml PBS. MDCK was dissociated using by 4 ml Trypsin/EDTA at 37° C. for 20 to 30 minutes. Trysin activity was neutralized by 20 ml MEM medium+10% FBS+P/S, and cells pelleted by centrifugation at 300×g, 5 minutes. Cells were resuspended in MEM medium+10% FBS, counted with a haemocytometer and normalized cell to $2\times10^5$ cell per ml for reverse transformation.

siRNA Preparation siRNA (20 numole) was dissolved in 200 ul DEPC-treated water to give 100 pmole per ul stock. Lipofectamine RNAimax was diluted 1:1000 with Opti-MEMi medium. On a 96 well round bottom suspension culture plate, 195 ul diluted lipofectamine was added to to row A, and 100 ul to each well from row B to row H. 5 ul dissolved siRNA each from the siRNA panel was added to a well in row A. The samples were mixed thoroughly by pipette up-and-down.

Virus Challenge (Performed in P3 Lab)

All siRNA transfected cells were washed with PBS twice. SOHI H1N1 (p6,2×105 PFU/ml) was diluted with MEM containing 2 ug/ml TPCK-Trypsin to final 200 PFU/ml. 100 ul diluted virus was added to each well, to give a final 20 PFU/well (~0.001 moi). After incubation for 48 hours at 37° C., in a CO2 incubator, the cytopathic effect (CPE) was scored, and the rough viral titre was checked with haemagglutination assay. The viral titer can also be quantified by real-time PCR.

TABLE 4

Eight siRNA Oligos were Selected According to Their Anti-H1N1 Activity (Table discloses SEQ ID NOS 3, 52, 4, 53, 5, 54, 6, 55, 56-57, 56, 58, 8, 59, 9, and 60. respectively, in order of appearance.

| | SiRNA sequences | Homologous to H1N1 2009 | IC50 (μM) |
|---|---|---|---|
| PB1-845s | UGGCAAAUGUUGUGAGAAAdTdT | 99.71 | ≤12.5 |
| PB1-845as | UUUCUCACAACAUUUGCCAdTdT | | |
| PB1-857s | UGAGAAAGAUGAUGACUAAdTdT | 99.27 | ≤12.5 |
| PB1-857as | UUAGUCAUCAUCUUUCUCAdTdT | | |
| PB1-1563s | UGACAUGAGUAUUGGAGUAdTdT | 99.56 | ≤12.5 |
| PB1-1563as | UACUCCAAUACUCAUGUCAdTdT | | |
| PB1-1406s | CCUGCAAGUUAGUGGGAAUdTdT | 98.84 | ≤12.5 |
| PB1-1406as | AUUCCCACUAACUUGCAGGdTdT | | |
| PB1-1783s | GGACCAAACUUAUACAAUAdTdT | 99.42 | ~25 |
| PB1-1783as | UAUUGUAUAAGUUUGGUCCdTdT | | |
| PA-1265s | GGAUAGAACUUGAUGAAAUdTdT | 99.7 | ≤25 |
| PA-1265as | AUUUCAUCAAGUUCUAUCCdTdT | | |
| PA-1054s | GAGAAGAUCCCAAGGACAAdTdT | 98.82 | ≤25 |
| PA-1054as | UUGUCCUUGGGAUCUUCUCdTdT | | |
| PA-1887s | GGAAGGCUCUAUUGGGAAAdTdT | 99.7 | ≤25 |
| PA-1887s | UUUCCCAAUAGAGCCUUCCdTdT | | |

Example 6. In Vivo siRNA Delivery Using Histidine-Lysine Polymer (HKP)

HKP-siRNA Nanoparticle

Figure 19:
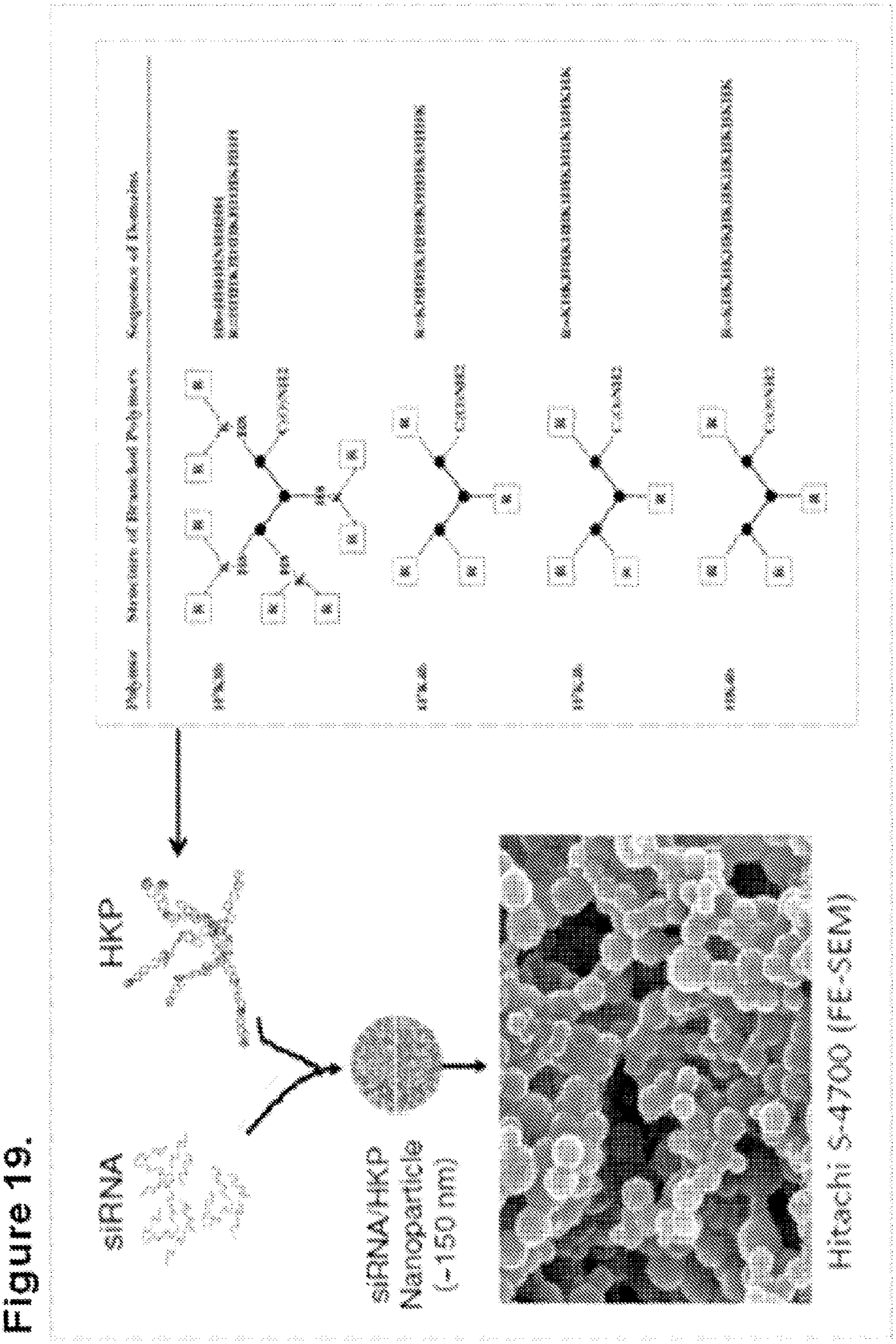
FIG. 19. HKP-siRNA Structures and Nanoparticle Appearance illustrated by Electron Microscopy. HKP-siRNA can be self assembled into nanoparticles.
Figure 20:
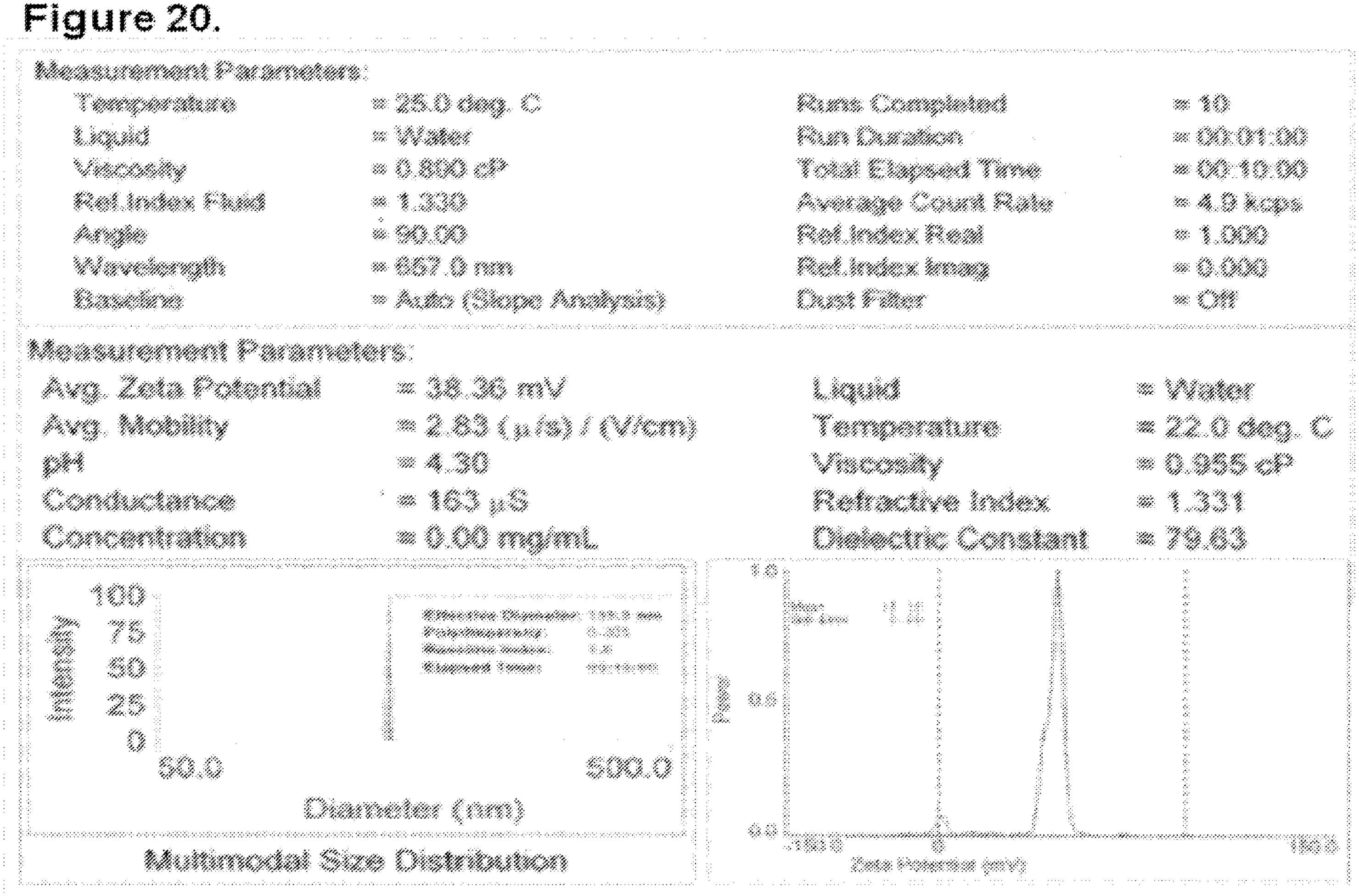
FIG. 20. Physicochemical Characterizations of HKP-siRNA nanoparticle using particle size measurement and zeta-potential measurement.
Figure 22:
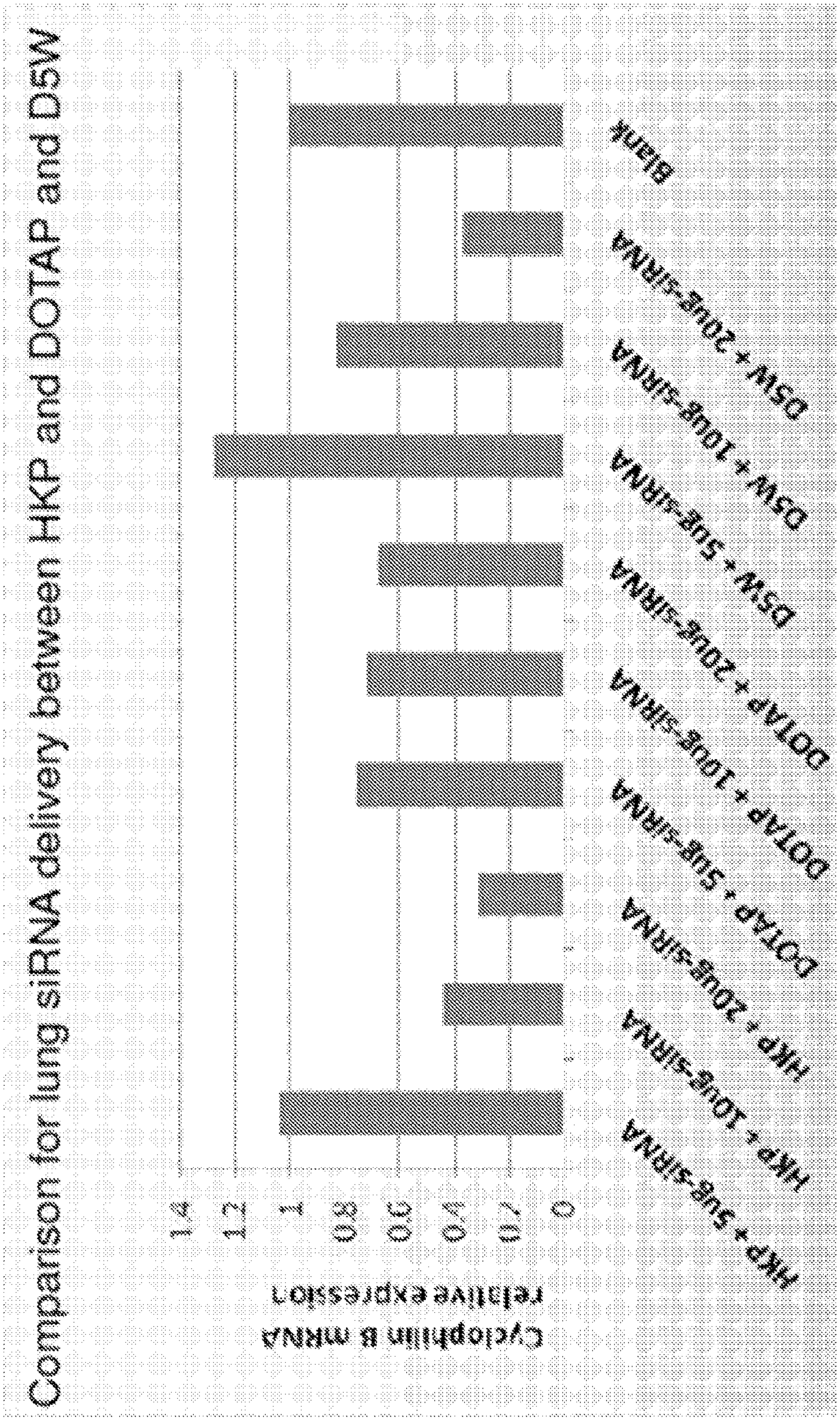
FIG. 22. HKP-siRNA is the Best for Airway siRNA Delivery Comparing DOTAP and D5W. The mouse lung endogenous gene Cyclophilin D was used as the in vivo gene silencing marker. Both HKP and D5W exhibited dose-dependent gene silencing activity.
Figure 23:
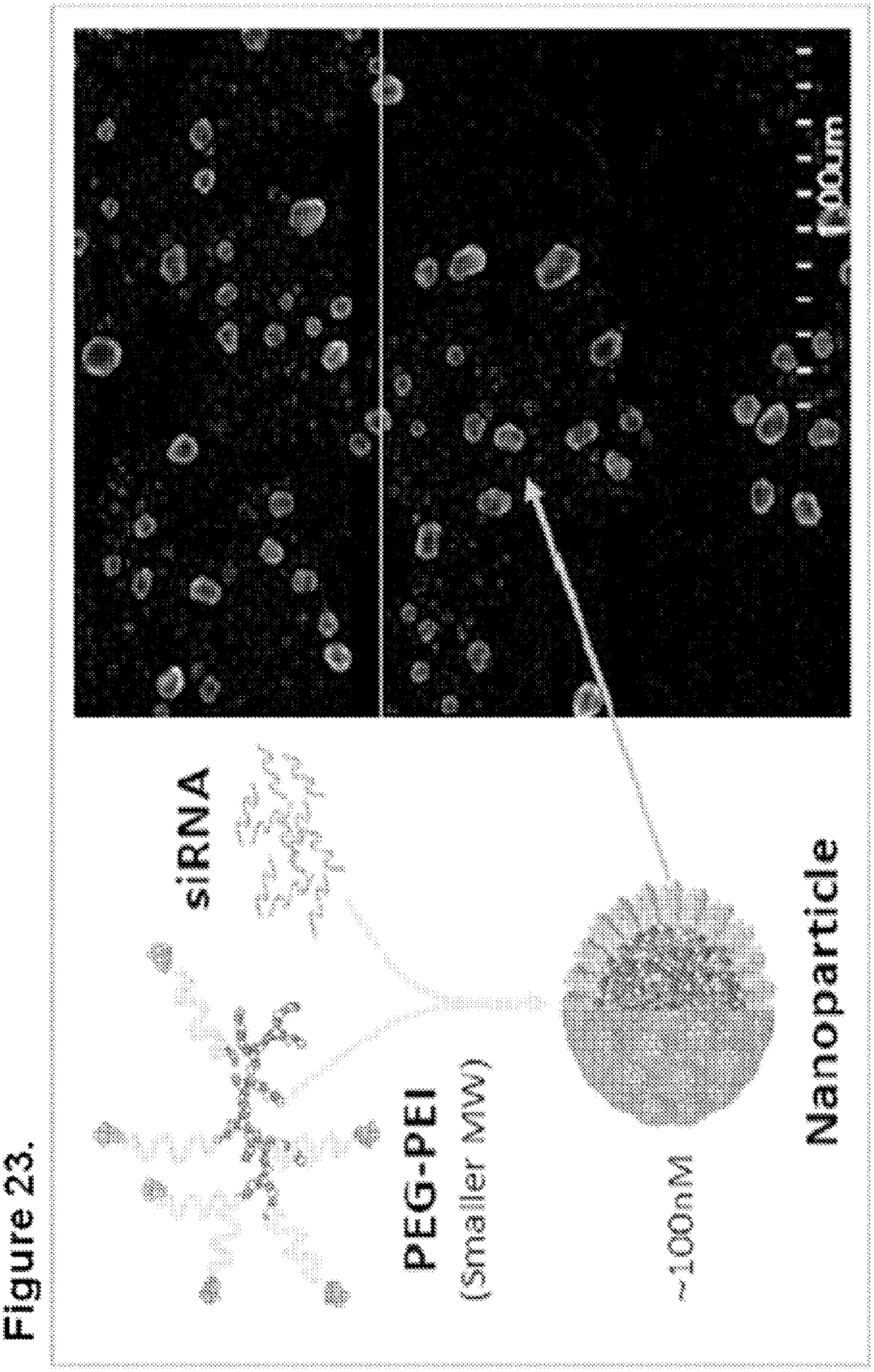
FIG. 23. PEG-PEI Structure and Topography PEG-PEI-siRNA Nanoparticle Structure and its SEM Image.

Histidine-lysine polymers (HKP) have been applied for siRNA delivery in vitro and in viva A pair of the HK polymer species, H3K4b and H3K(+H)4b, has a Lysine backbone with four branches containing multiple repeats of Histidine, Lysine or Asparagine. When this HKP aqueous solution was mixed with siRNA at a N/P ratio of 4:1 by mass, the nanoparticles (average size of 150 nm in diameter) were self-assembled (FIG. 19). Optimal branched histidine-lysine polymer, HKP, was synthesized on a Ranin Voyager synthesizer (PTI, Tucson, Ariz.). The two species of the HKP used in the study were H3K4b and H3K(+H)4b with a structure of (R)K(R)-K(R)-(R)K(X), for H3K4b where R=KHHHKHHHKHHHKHHHK; and for H3K(+H)4b where R=KHHHKHHHKHHH(H)KHHHK, X=C(O)NH2, K=lysine and H=histidine. The particle size and zeta-potential were measured with Blookheaven's Particle Sizer 90 Plus (FIG. 20.). The HKP-siRNA aqueous solution was semi-transparent without noticeable aggregation of precipitate, and can be stored at 4° C. for at least three months. We applied H3K4b and H3K(+H)4b for respiratory siRNA delivery in comparison with D5W (5% glucose solution) and DOTAP (FIG. 22).

Measurement of HKP-siRNA Nanoparticles

Using Brookhaven Particle Sizer 90 Plus, we have measured HKP-siRNA nanoparticles for their average size and Zeta-potential in addition to the electron microscopic observation.

Primary Cell siRNA Delivery with HKP

Figure 21:
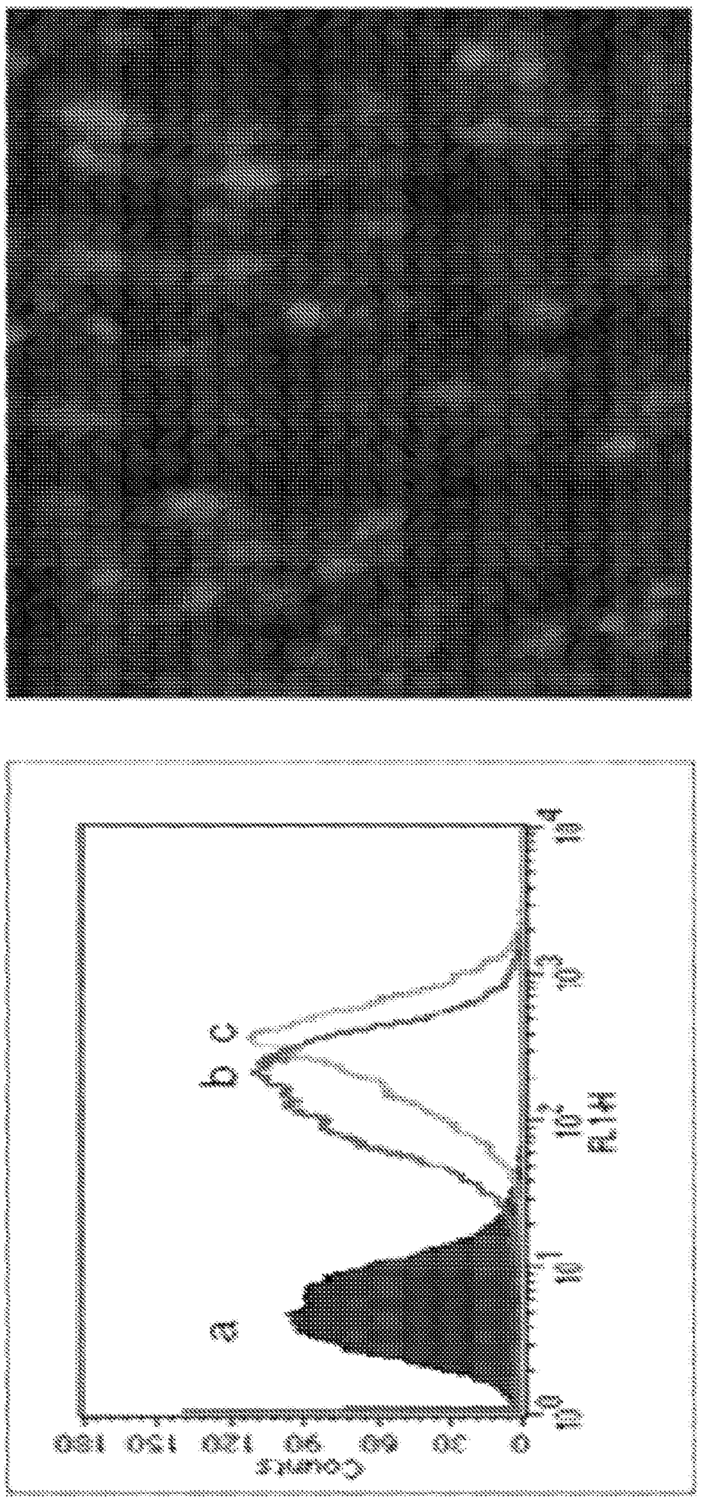
FIG. 21. Transfection Efficiency of HKP in MEF cells with florescent siGLO siRNA as an indicator. A: Measured by flow cytometry analysis; B: Observed by microscope image.

To establish in vitro silencing system, we explored cells for both tranfectability and responsiveness to IL-13 stimulation with mouse embryo fibroblast (MEF) cell model. Cell responsiveness to IL-13 was seen with high transfection efficiency with Ribojuice and HKP. Over many cell lines studied, MEF cells released eotaxin from IL-13 induction in a dose-dependent response (data not shown). Next, we tested the transfection efficiency in vitro with available transfection reagents, among them, ribojuice (similar to jetPEI) and HKP have given best results. Over 93% of MEF cells have been transfected with those two reagents using florescent siGLO siRNA as an indicator, measured by flow cytometry analysis (FIG. 21A) and under microscope image (FIG. 21B).

Respiratory Tract siRNA Delivery

We further tested HKP-siRNA nanoparticle for respiratory track delivery. To compare the delivery efficiency of HKP-siRNA, we also included D5W (5% glucose) and DOTAP in the testing groups. The Kunming mice (25 g in average) were treated by HKP-siRNA nanoparticle solution, D5W and DOTAP with Cyclophilin B specific siRNAs, through both intranasal and intratracheal deliveries. The device used in the study came from BioLITE Intubation Illumination System, HKP-siRNA formulation was administrated with 50 μl in volume each time. From FIG. 22, it is very clear that HKP-siRNA was able to deliver siRNA against Cyclophilin B, an endogenously expressed gene, and resulted in the best silencing activities. A dose dependent response was observed with HKP delivered Cyclophilin B specific siRNA. The other two treatments with DOTAP and D5W delivered Cyclophiin B specific siRNA also presented the dose dependent response curves. However, DOTAP did not provide stronger silencing activity. At a higher dose (20 μg per lung), HKP and D5W exhibited similar silencing activities. With HKP-siRNA treated animals, we did not see any toxicity effect in lung tissue nor other tissues. Using the endogenous gene marker, Cyclophilin B, has allowed us to evaluate the target knockdown throughout the whole lung but not only the epithelium layers of the lung tissue.

Example 7. In Vivo siRNA Delivery Using Small Molecular Weight Pegylated-PEI

Small Molecular Weight PEG and PEI

The PEG8 and PEI1.8K is one pair and PEG4.57-PEI25K represents another pair for the small molecular weight PEG-PEI conjugation. The preferred N/P ratio for this type of PEG-PEI/siRNA nanoplex is 7 to 10. To calculate the N/P ratio for the first carrier using the following formula: $N/P=325\times\{[(m/17800)\times 41.86]/n\}$. Where N is mole number of N in the co-polymer molecule and P is mole number of P in the siRNA, (m) is the gram number of PEG-PEI, and (n) is the gram number of siRNA. For example: N/P is 10, and siRNA is 0.00003 (30 μg), you have: $10=325\times\{[(m/17800)\times 41.86]/0.00003\}$, therefore: $M=[(10/325)\times 0.00003]/41.86]\times 17800=0.000392$ g (392 μg). We can translate the N/P ratio (10) for PEG8-PEI1.8K/siRNA into the w/w ratio: 393/30=13/1.

Prepare PEG-PEI-siRNA Solution

An aqueous solution of siRNA was added drop-wise to DEPC-treated water containing PEG-PEI while vortexing. Different copolymer concentrations were used to provide polymer-siRNA nanocomplexes with different N/P ratios. After addition, the mixture was vortexed for an additional 20 seconds and then allowed to incubate at room temperature for 30 minutes before analyses or use. When N/P ration 10, When using 3 μg siRNA per dose, 39 μg of PEG-PEI should be used, When using 10 μg siRNA per dose, 130 μg of PEG-PEI should be used, When using 30 μg siRNA per dose, 390 μg of PEG-PEI should be used. Total volume for each dose should be 100 μl. When N/P ration 7, When using 3 μg siRNA per dose. 27 μg of PEG-PEI should be used. When using 10 μg siRNA per dose, 90 μg of PEG-PEI should be used. When using 30 μg siRNA per dose, 270 μg of PEG-PEI should be used. Total volume for each dose should be 100 μl.

For the Second Carrier

To calculate the N/P ratio for the second carrier using the following formula: $N/P=325\times\{[(m/34140)\times 581.39]/n\}$. Where N is mole number of N in the co-polymer molecule and P is mole number of P in the siRNA, (m) is the gram number of PEG-PEI, and (n) is the gram number of siRNA. For example: N/P is 10, and siRNA is 0.00003 (30 μg), you have: $10=325\times\{[(m/34140)\times 581.39]/0.00003\}$, therefore: $M=[(10/325)\times 0.00003]/581.39]\times 34140=0.0000542$ g (54 μg), We can translate the N/P ratio (10) for PEG4.57-PEI25K/siRNA into the w/w ratio: 54/30=1.8/1. An aqueous solution of siRNA (300 μg/mL) was added drop-wise to DEPC-treated water containing PEG-PEI (395 μg/ml) while vortexing. Different copolymer concentrations were used to provide polymer-siRNA nanocomplexes with different N/P ratios. After addition, the mixture was vortexed for an additional 20 seconds and then allowed to incubate at room temperature for 30 minutes before analyses or use. When N/P ration 10: When using 3 μg siRNA per dose, 4.8 μg of PEG-PEI should be used; When using 10 μg siRNA per dose, 18 μg of PEG-PEI should be used; When using 30 μg siRNA per dose, 54 μg of PEG-PEI should be used. Total volume for each dose should be 100 μl. When N/P ration 7: When using 3 μg siRNA per dose, 3.9 μg of PEG-PEI should be used; When using 10 μg siRNA per dose, 13 μg of PEG-PEI should be used; When using 30 μg siRNA per dose, 39 μg of PEG-PEI should be used. Total volume for each dose should be 100 μl. Optional: Particle size was determined by dynamic light scattering (DLS) on a 90 plus particle size analyzer (Brrokhaven Instruments, Holtzville, N.Y. USA)

Example 8. Mouse Model with Influenza a Virus Challenge for Evaluation of siRNA Therapeutics Mouse Model with H5N1 Viral Challenge Female Balb/c mice at age of 4-6 weeks were used for establishment of H5N1 challenged model for evaluation of the prophylactic and therapeutic benefit of siRNA therapeutic in vivo. Most cohort groups had five mice and a couple of them had ten mice. The mice were challenged with H5N1 virus (strain A/Vietnam/1194/04) at a 10 times of LD50. All 5 animals in the control group died between 7-10 days after viral inoculation through nasal drops.

Prevention Treatment

Figure 24:
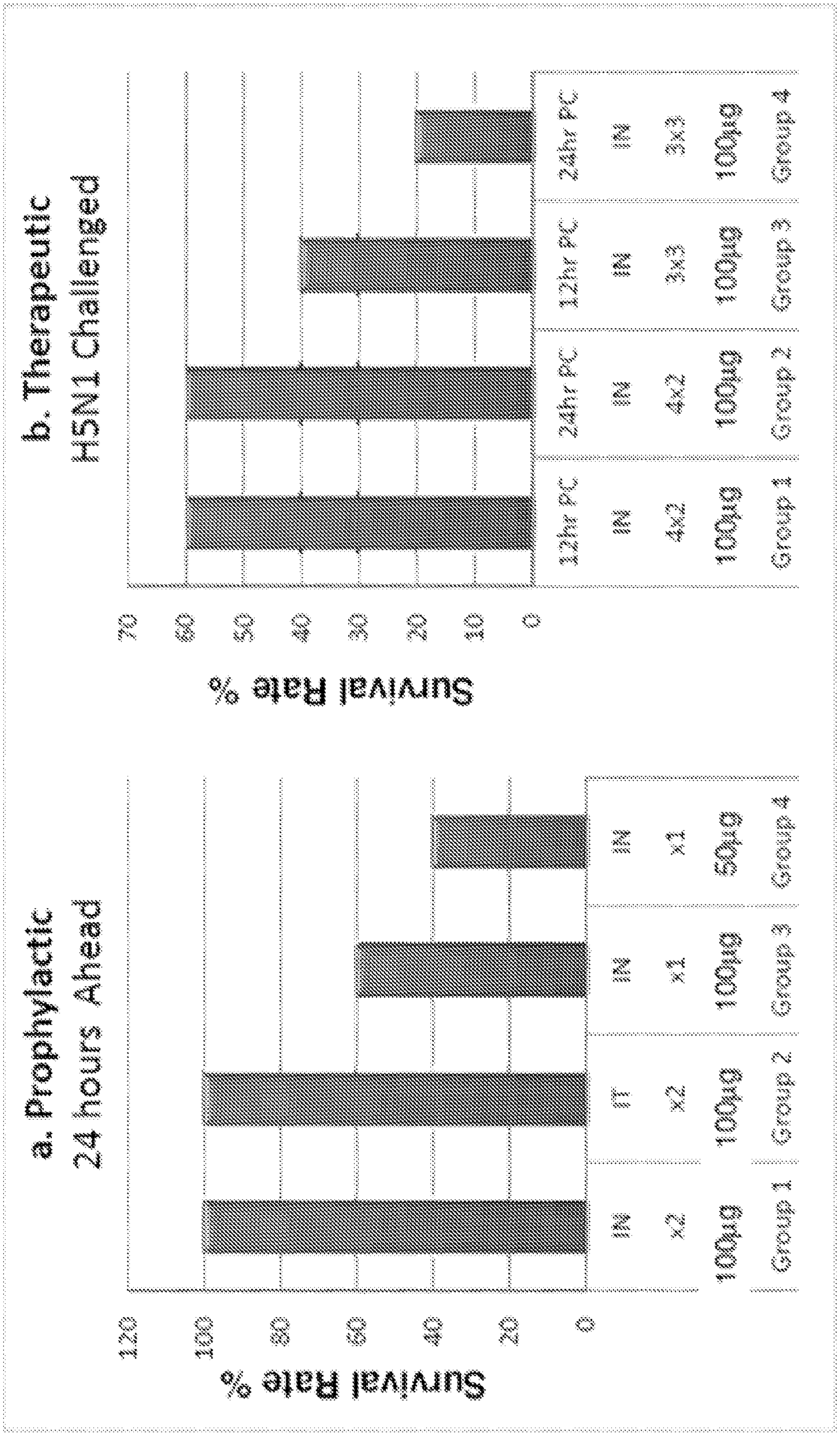
FIG. 24. Prophylactic and Therapeutic Treatments of H5N1 Challenged Mice Measured for Their Survival Rate. A. the prevention treatment demonstrated 100% survival in H5N1 challenged mice with a clear dose dependent response. B. therapeutic treatment with higher and more frequent dosages allowed 60% survival regardless of starting point at 12 hour or 24 hour post viral challenge. An initial higher dose appears more important than longer treatment time for better survival rate.

Mice were given PEG-PEI-siRNA via intra-tracheal instillation with 100 μg (siRNA)/100 μl D5W solution one day before viral inoculation and then additional 100 μg (siRNA)/100 μl D5W solution was given at the same time of the viral inoculation. The siRNA used in this study was selected from a number of previous studies and it is a 21 mer siRNA containing a "potency-enhancing motif". When 100 μg of NP specific siRNA packaged with PEG-PEI nanoparticle formulation was intranasally or intratracheally addressed (100 μg/dose×2) to the healthy mice before the viral challenge, 100% of the testing mice were survived and fully recovered, even if they were viral challenged later. If only one of 100 μg/dose was used, the survival rate dropped to 60%. If the dosage of siRNA was further decreased, the survival rate is further dropped into 40% (FIG. 24).

Therapeutic Treatment

After the viral challenge for 12 hours or 24 hours, various dosages of PEG-PEI-siRNA were used for therapeutic treatment evaluation. When 100 μg/dose at 4 times/daily for two days was applied, 60% of mice were survived. When 100 μg/dose at 3 times/daily for three days was applied, only 40% of mice were survived (FIG. 24).

Example 9. A "Potency Enhancing Motif" (PEM) Results in a Better Survival Rate of the Viral Challenged Mice An Interesting Motif Due to the protection potency of certain siRNA sequences, a 5 nucleotide motif was identified: Sense, 5'-ACUCC-3'; Antisense, 5'-GGAGU-3'. Although the exact mechanism of action of this motif for improving the infected animal survival is not clear, the experiments for prophylactic and therapeutic benefits are very substantial.

Prophylactic Treatment with or without the Motif

We selected siRNA oligos against for influenza genes: NP, PB1, PB2 and PA. Three siRNA oligos were selected to target each of these genes with one oligo containing the motif but other two oligos are not. For prevention treatment, 100 μg of PEG-PEI-siRNA was intratracheally administrated to the animals one day before the viral inoculation. Another 100 μg of PEG-PEI-siRNA was intranasally administrated to the animals at the same time as the viral inoculation.

Therapeutic Treatment with or without the Motif

Figure 25:
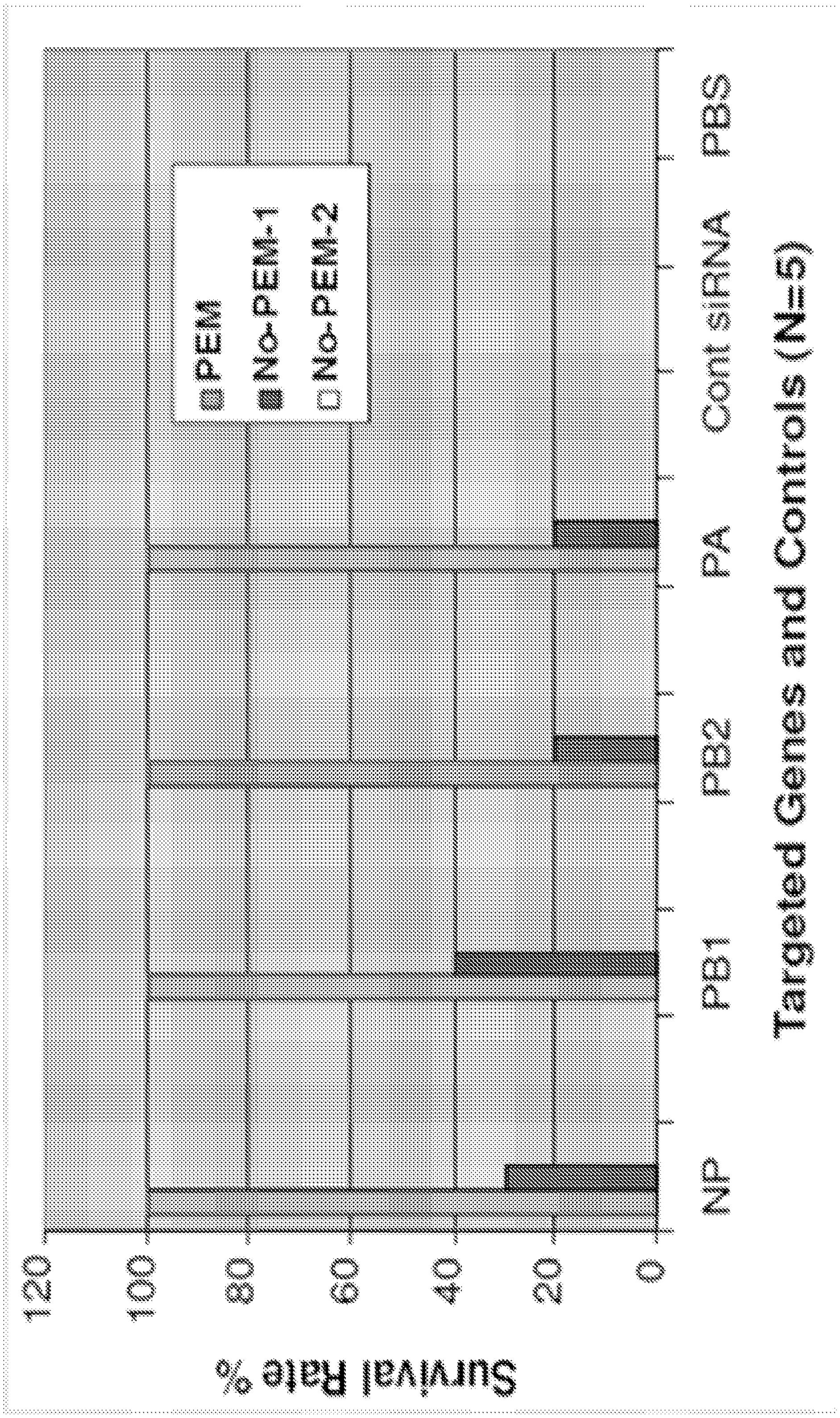
FIG. 25. Potency Enhancing Motif (PEM) Containing siRNAs Showed Potent Protection Benefit. SiRNAs against four gene targets provided similar results that PEM containing siRNA oligos protected viral challenged mice with 100% of survival, comparing 40% and 0% of survival treated with different siRNA oligos.

Based upon the prophylactic treatment result, we selected siRNA specific to NP gene of influenza A for the therapeutic treatment evaluation. At 24 hour time point post viral inoculation, we dose animals with PEG-PEI-siRNA with different regimens: on day one, 200 μg for intravenous administration and 100 μg for intranasal administration; on day two, 100 μg for intranasal administration; on day four, 100 μg for intranasal administration; and on day six, 100 μg for intranasal administration. As the result, animals treated with PEG-PEI-siRNA containing PEM have 60% survival rate, otherwise 0% survival in the control group. The study were conducted twice with N=10 and N=5 with the same results (FIG. 25).

Example 10. Comparing siRNA Therapeutics with Existing Flu Therapeutics

Figure 26:
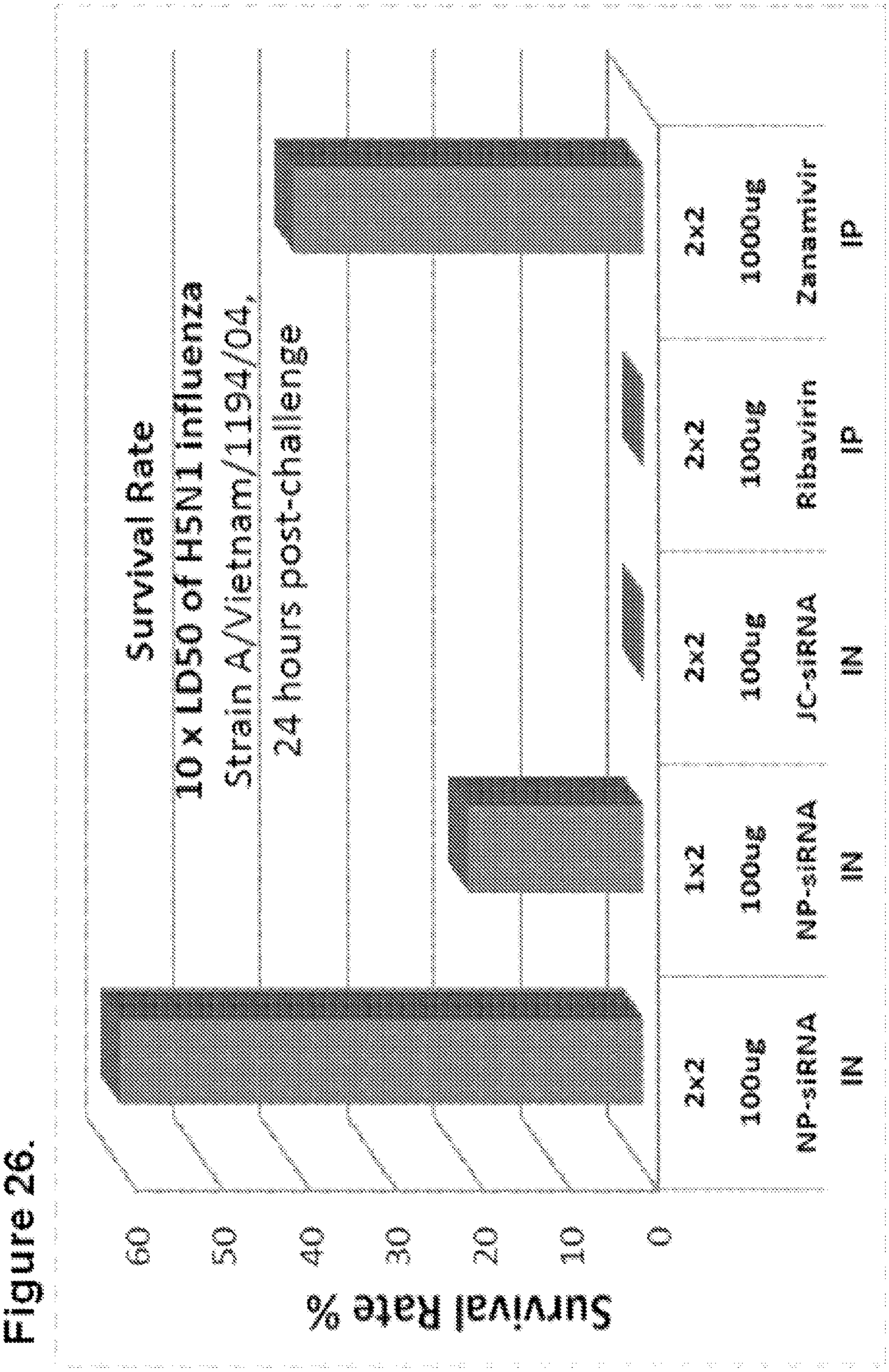
FIG. 26. The PEG-PEI-siRNA nanoparticle formulations exhibited better efficacy than other chemodrugs against influenza H5N1 This therapeutic benefit tested with H5N1 challenged mouse indicated that siRNA can be a better therapeutic for flu treatment.

Based upon the studies on the prophylactic and therapeutic treatments with or without PEM, we decided to compare the selected siRNA drug (PEG-PEI-siRNA$_{NP}$) with Ribavirin, Zanamivir and a different siRNA inhibitor (also targeting NP gene of influenza A) published by a different group. Ten mice per group were challenged by 10 times LD50 of H5N1 virus strain A/Vietnam/1194/04. 24 hours after viral inoculation, the mice were treated with regimens illustrated in FIG. 26.

Example 11. Predication of siRNA Duplexes Against Influenza Viral Sequences

Figure 27:
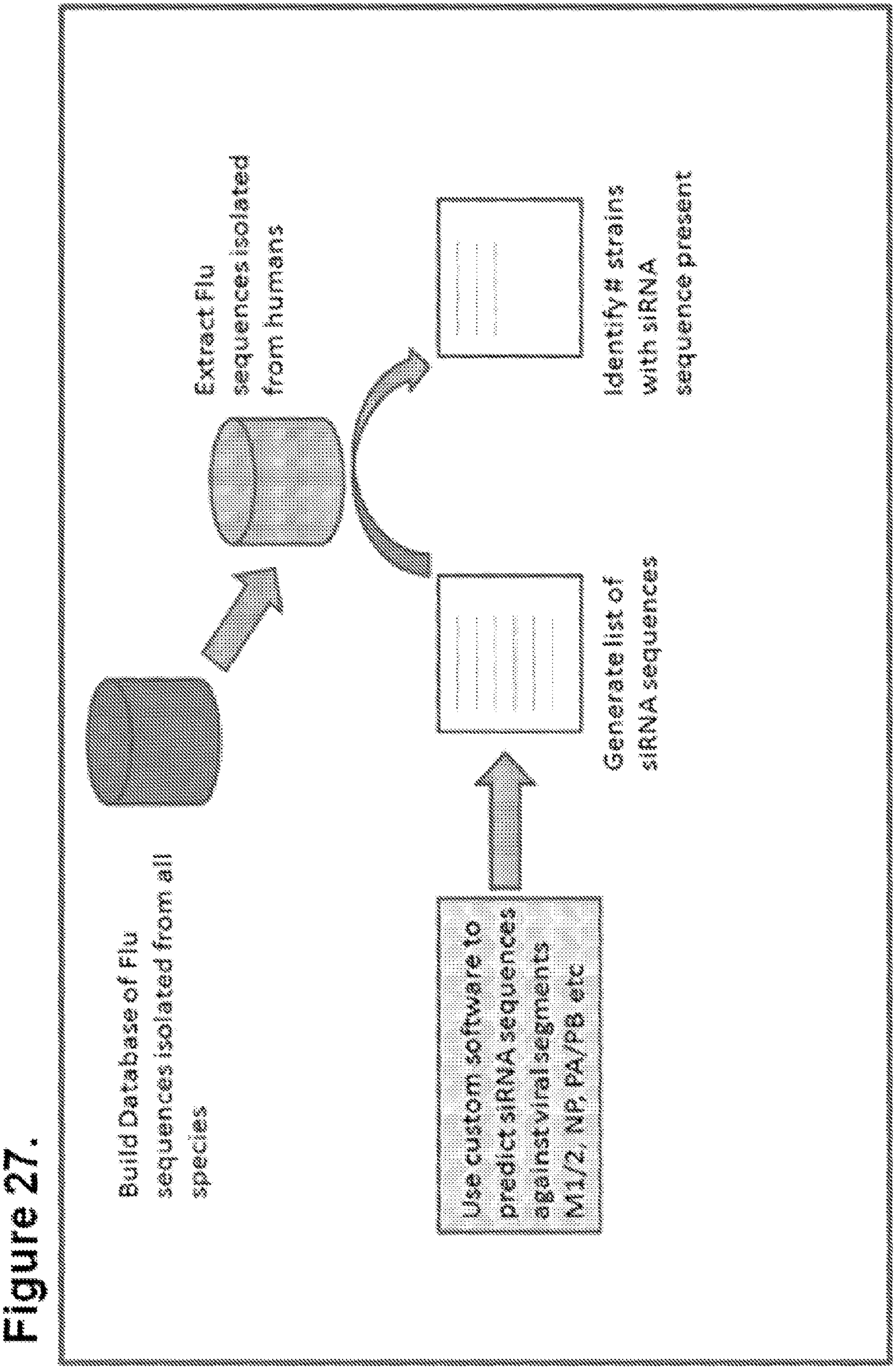
FIG. 27. Process for siRNA prediction against influenza A viruses. siRNAs predicted against a gene segment across multiple flu strains are then compared for viral coverage across a database of flu strain sequences. The siRNAs with broadest strain specificity were selected.
Figure 28:
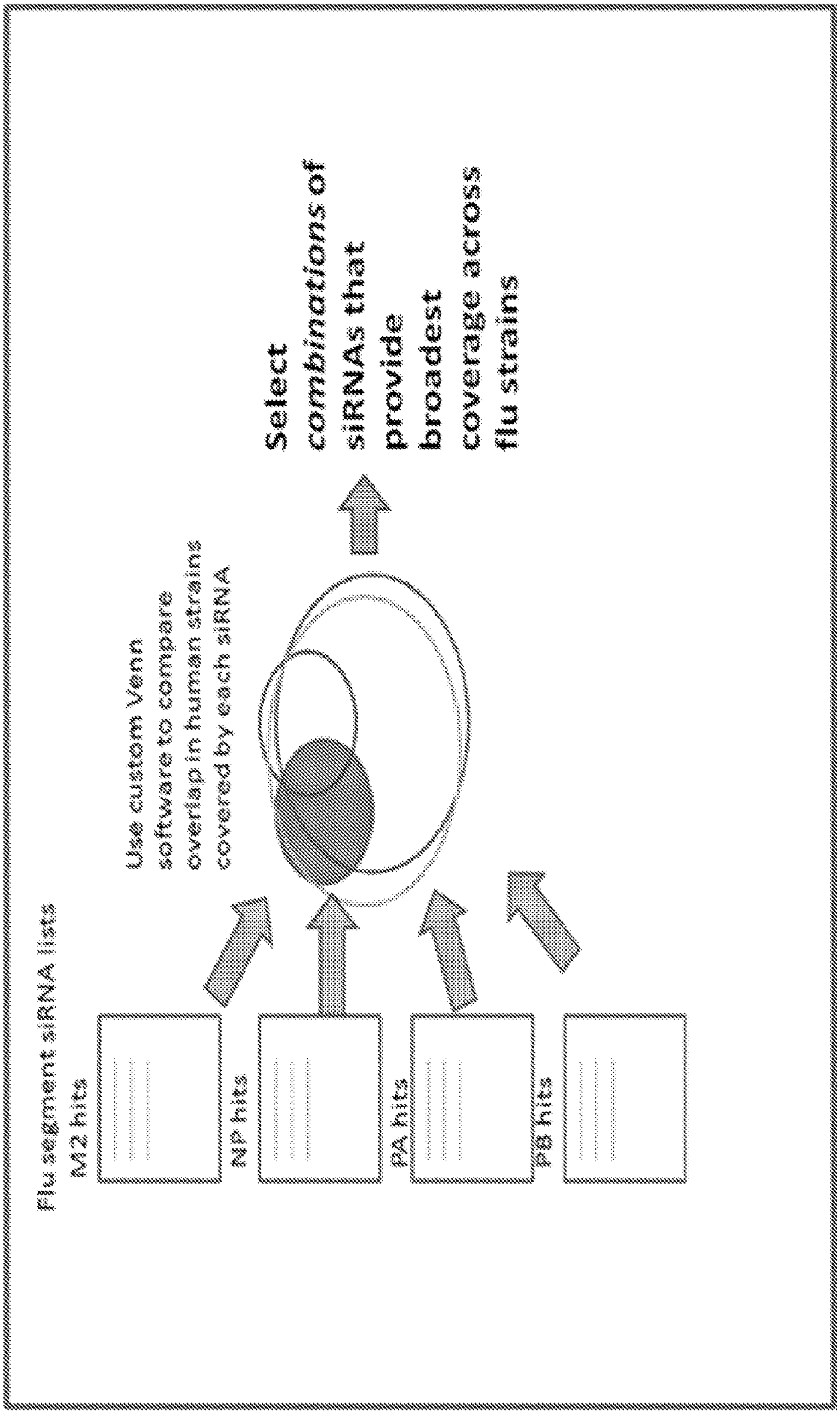
FIG. 28. In house novel algorithm using proprietary software. We took lists of the flu strains covered and examined the coverage for each siRNA alone and in combination with each other siRNA (against distinct segments). This results in the identification of combinations of siRNAs that provide broadest strain coverage.
Figure 29:
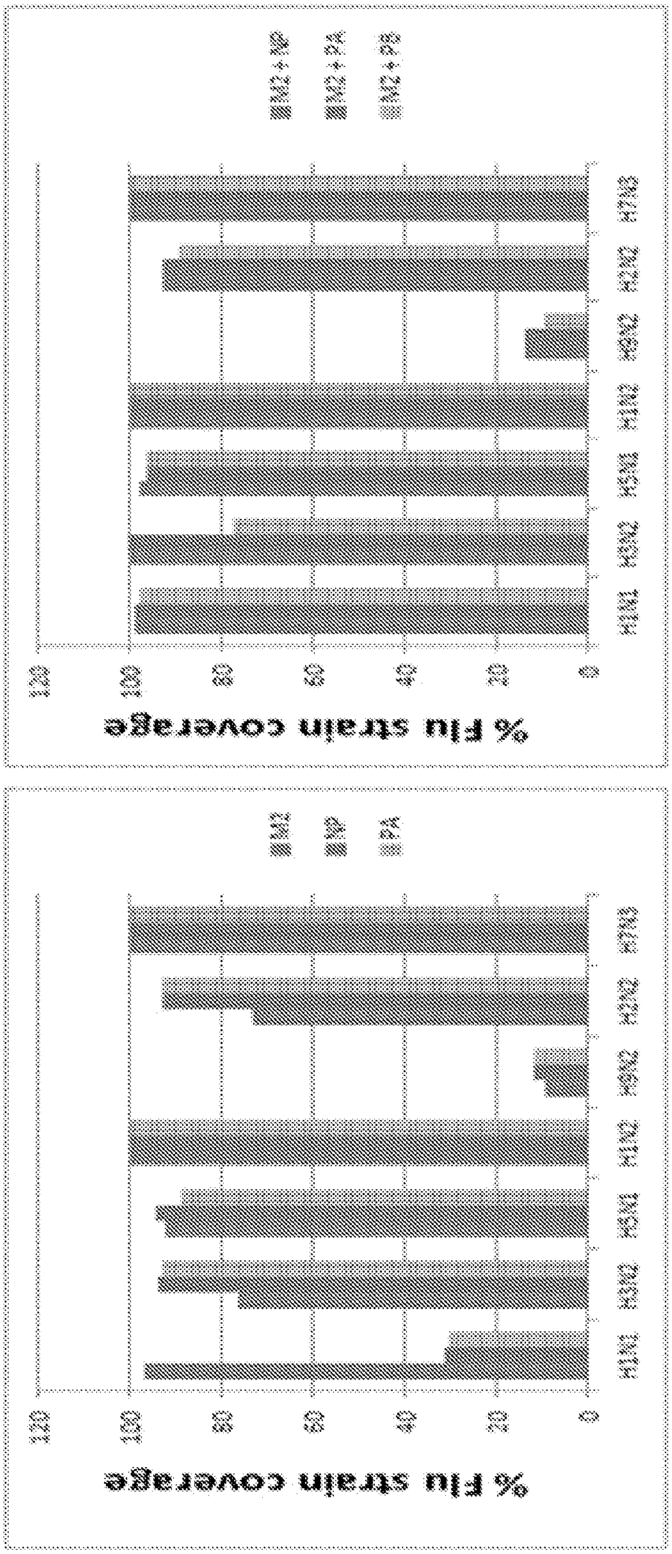
FIG. 29. Left panel. % of all human flu strains predicted to have sequence identity with single siRNA against one flu segment. Note H3N2/H5N1 coverage by a single siRNA is 95% max for each. Right panel. Combining siRNAs against 2 flu segments improves predicted flu strain coverage. Note M2+NP coverage versus H3N2/H5N1 increases to 99-100%. Note M2+NP and M2+PA provide best coverage. M2+PB sequence was not quite as good.

We use the following figures to explain how we identify potent siRNA sequences with broad coverage against most influenza viral genes. FIG. 27 demonstrates Process for siRNA prediction. siRNAs predicted against a gene segment across multiple influenza A strains are then compared for viral coverage across a database of flu strain sequences. The siRNAs with broadest strain specificity were selected. FIG. 28 indicates that using proprietary software we took lists of the flu strains covered and examined the coverage for each siRNA alone and in combination with each other siRNA (against distinct segements). This results in the identification of combinations of siRNAs that provide broadest strain coverage. FIG. 29 further demonstrated the selected siRNA sequences may be able cover above 90% of corresponding strains reported within the database. Sequence Homology with Influenza A virus strains reported in Genebank. On the left panel, blue represents M2 specific siRNA sequence, red represents NP specific siRNA sequence, and green represents PA specific siRNA sequence. The bars indicate percentages of each siRNA covered within Genebank published viral sequences. On the right panel, blue represents M2 and NP specific siRNA pair, red represents M2 and PA specific siRNA pair, and green represents M2 and PB specific siRNA pair. The percentage of covered viral sequences are further increased by each pair.

Example 12. Screening Anti-H1N1 siRNA Using MDCK Cells

In order to select a group of siRNA sequences with potent anti-influenza virus using cell culture assays, Influenza virus A/California/07/09(H1N1)pmd09 from the viral strain collection of the Center for Disease Control (CDC, Atlanta, Ga., USA) was cultivated in the allantoic cavity of the 9-11 day old chicken embryos for 48 hours at 36° C. MDCK cell line (ATCC CLL-34) from the collection of the Research Institute of Influenza RF MPHSD (RII) was used. Cells were cultured in the Minimum Essential Medium (MEM) in 24 and 96-well plates until the formation of a cell monolayer and then used for the further experiments. For cell transfection, siRNA duplexes (Table 5)-polycation complexes were prepared at the ratio N:P=3:1. To investigate transfection efficiency with the fluorescently labeled siRNA, the cells were incubated with the complexes for 24 hours. Complexes against the cellular genes siRNAc were also incubated with the cells for 24 hours. When studying the antiviral activity of siRNA as a prophylactic or therapeutic, the cells were incubated with the complexes for 1 hour and 24 hours respectively. Transfection of MDCK cells with Lipofectamine was performed in accordance with manufacturer recommendations.

TABLE 5

The siRNA sequences identified above were tested for their abilities to silence the flu gene target of interest and to determine the effect on viral replication in vitro. Table discolses Sense sequenses as SEQ ID NOS 14, 61-66, 12, and 67, and Antisense sequences as SEQ ID NOS 11, 68-73, 13, and 74, all respectively, in order of appearance.

| Name | siRNA Sense Sequences | siRNA Antisense Sequences |
|---|---|---|
| 89 | 5'-UACGCUGCAGUCCUCGCUCACUGGG-3' | 5'-CCCAGUGAGCGAGGACUGCAGCGUA-3' |
| 91 | 5'-AUGGCCAUCCGAAUUCUUUUGGUCG-3' | 5'-CGACCAAAAGAAUUCGGAUGGCCAU-3' |
| 93 | 5'-UUGAUGGCCAUCCGAAUUCUUUUGG-3' | 5'-CCAAAAGAAUUCGGAUGGCCAUCAA-3' |
| 95 | 5'-GCUGACCCUGAAGUUCAUCUGCAUU-3' | 5'-AAUGCAGAUGAACUUCAGGGUCAGC-3' |
| 97 | 5'-AUCCACAGCAUUCUGCUGUdTdT-3' | 5'-ACAGCAGAAUGCUGUGGAUdTdT-3' |
| 99 | 5'-UUCGACCUCGGUUAGAAGAdTdT-3' | 5'-UCUUCUAACCGAGGUCGAAdTdT-3' |
| 101 | 5'-GGGAACAGAUGUACACUCCdTdT-3' | 5'-GGAGUGUACAUCUGUUCCCdTdT-3 |
| 103 | 5'-GCAAUUGAGGAGUGCCUGAdTdT-3' | 5'-UCAGGCACUCCUCAAUUGCdTdT-3' |
| 105 | 5'-GGAUCUUAUUUCUUCGGAGATdT-3' | 5'-CUCCGAAGAAAUAAGAUCCdTdT-3' |

Figure 30:
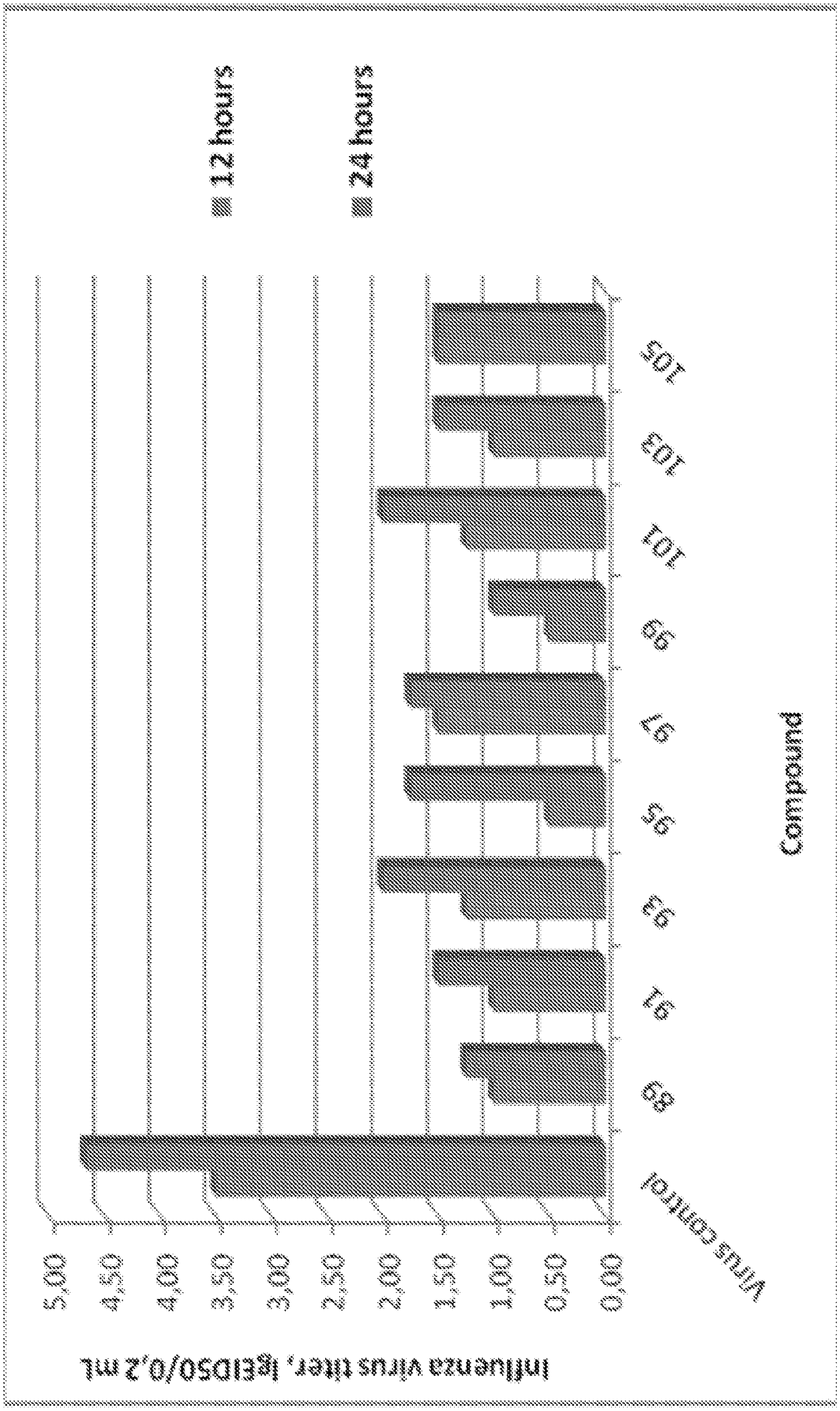
FIG. 30. Using MDCK Cells to test siRNA anti-influenza virus activity in vitro. In Vitro testing of the siRNAs identifies potent sequences with viral titer reduced up to 86% within the first 12 h. All siRNAs tested reduced viral titer by >55% within 12 h and similar levels of inhibition were observed at 24 h.

To study antiviral activity of siRNA cells, MDCK cells were inoculated with the virus dose of 0.1 TCID50 (50% of tissue culture infective dose) per cell. After 1-hour incubation, unattached virus was removed by washing with PBS. Then, siRNA-polycation complexes or siRNA complexes with lipofectamine were mixed with virus cultivation medium and the composed medium was added to each well with infected MDCK cells. Virus cultivation medium consisted of MEM containing 0.5% albumin (Calbiochem), 1 μl/ml trypsin (Fluka No293610), and 16 mM HEPES pH 7. 4 (Sigma NoH4034-500G) and 20 μg/ml ciprofloxacin. Plates were incubated in CO2 incubator at 37° C. and 5% CO2, and the culture fluid was collected after 24 hours incubation. To determine the virus infectious titers, ten-fold serial dilutions (10-1-10-6) were prepared from the samples of the culture fluid with the culture medium. MDCK cells were infected with diluted samples and incubated for 48 hours. After that, virus replication was measured by hemagglutination in the plates. The hemagglutination reaction was performed with 1% chicken red blood cells (RBC). Virus titer was considered as reciprocal to the final dilution of the inoculumable to cause cytopathogenic effect in 50% of cells and was expressed as 50% infecting doses. The antiviral activity of the studied complexes was determined by their ability to exhibit a lower infectious viral titer in comparison with the control values (FIG. 30).

Figure 31:
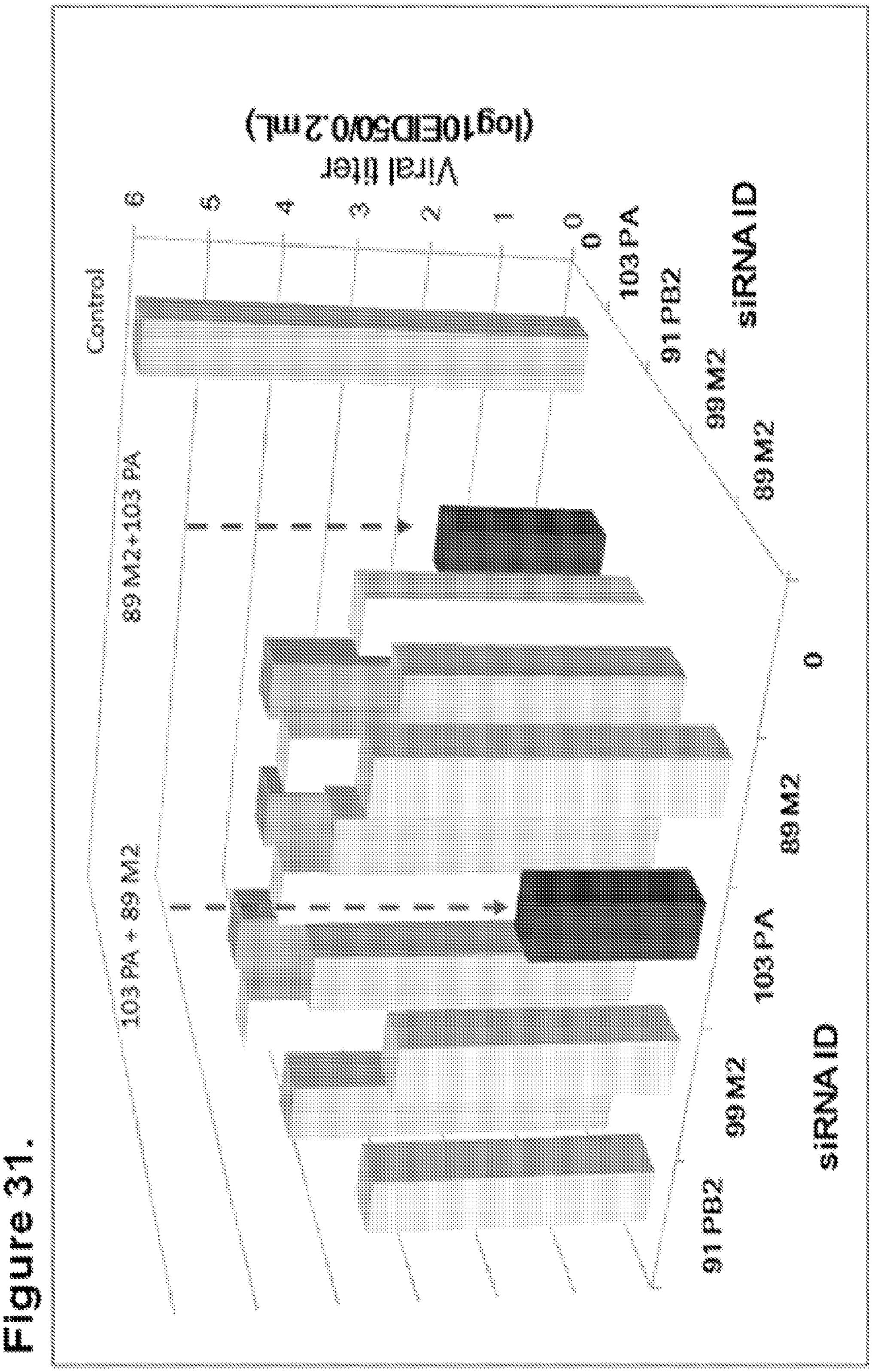
FIG. 31. Identification of an siRNA Pair with Stronger Antiviral Activity. When we tested siRNA duplexes with two-two pairing using H1N1 challenged MDCK cell culture, the 89/103 pair exhibited further enhanced anti-influenza activity.

Example 13. Selection of the Most Effective siRNA Pair Against Influenza Viruses Through two-two pairing, we are able to identify a pair of siRNA duplexes with further improved antiviral activity in H1N1 challenged MDCK cell culture. The combination of #89/#103 siRNA pair demonstrated stronger anti-influenza activity than either single siRNA at the same concentration (FIG. 31). The sequence of #89 siRNA targeting the influenza M2 gene with homology to sense: 5'-UACGCUGCAGUCCUCGCUCACUGGG-3' (SEQ ID NO: 14) and antisense: 5'-CCCAGUGAGCGAGGACUGCAGCGUA-3' (SEQ ID NO: 11). The sequence of #103 siRNA targeting the influenza PA gene with homology to sense: 5'-GCAAUUGAGGAGUGCCUGAdTdT-3' (SEQ ID NO: 12) and antisense: 5'-UCAGGCACUCCUCAAUUGCdTdT-3' (SEQ ID NO: 13).

Effects of combining 2 siRNAs (one against M2 and the other against PA) on antiviral effects against Influenza strains H1N1 (left), H3N2 (middle) and H5N2 (right). siRNAs were administered in PAA at various concentrations ranging between 5 nM and 40 nM. The bar at the rear right of each figure represents the viral titer measured in the presence of the vehicle alone. As the concentration of each siRNA is increased we see a dose dependent decrease in viral titer against each viral strain. Notice that in each case a combination of 20 nM of each of the siRNAs was more potent than 40 nM of either siRNA alone (front left bar in each figure).

Figure 32:
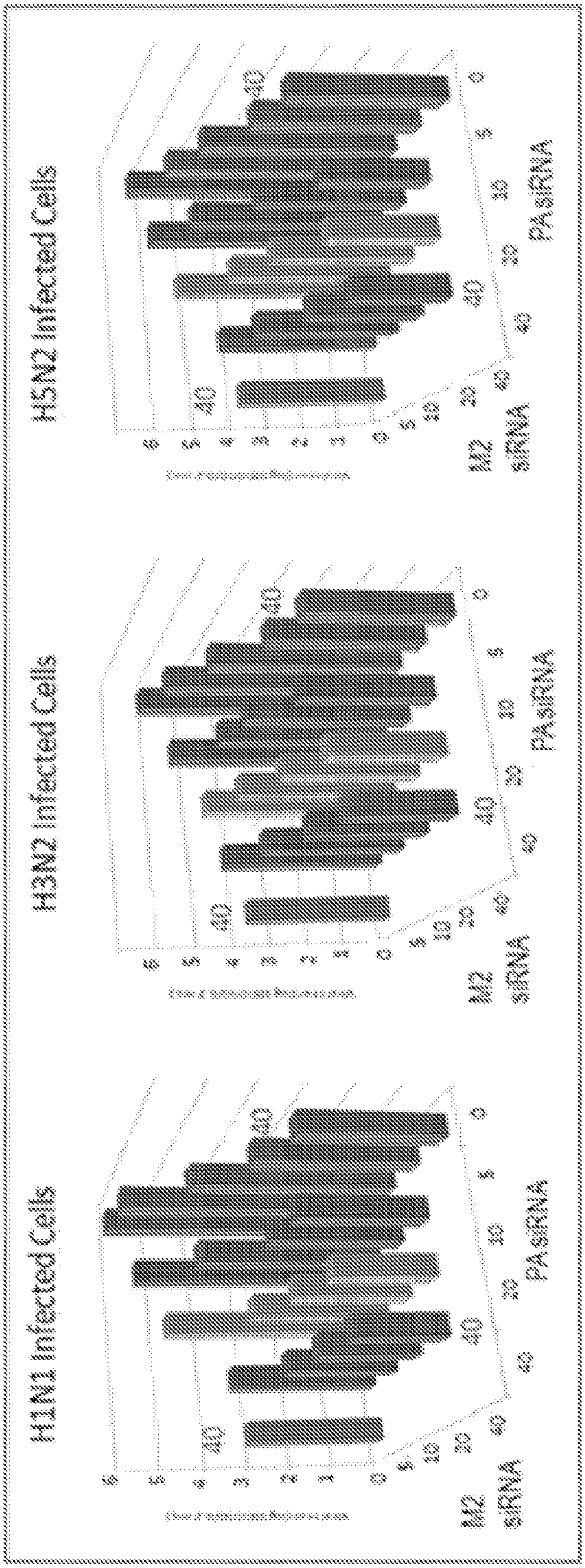
FIG. 32. The Combination of siRNA #89 and #103 targeting both M2 viral RNA and PA viral RNA at the same time exhibited stronger anti-viral effect. Within the H1N1 challenged MDCK cell culture, the combined siRNA pair at 40 nM concentration (20 nM M2-siRNA+20 nM PA-siRNA) resulted in stronger viral inhibition than those single siRNA duplex at the same concentration (40 nM M2-siRNA or 40 nM PA-siRNA). More interestingly, this synergistic effect can be observed not only with H1N1 but H3N2 and H5N2 viral strains.
Figure 33:
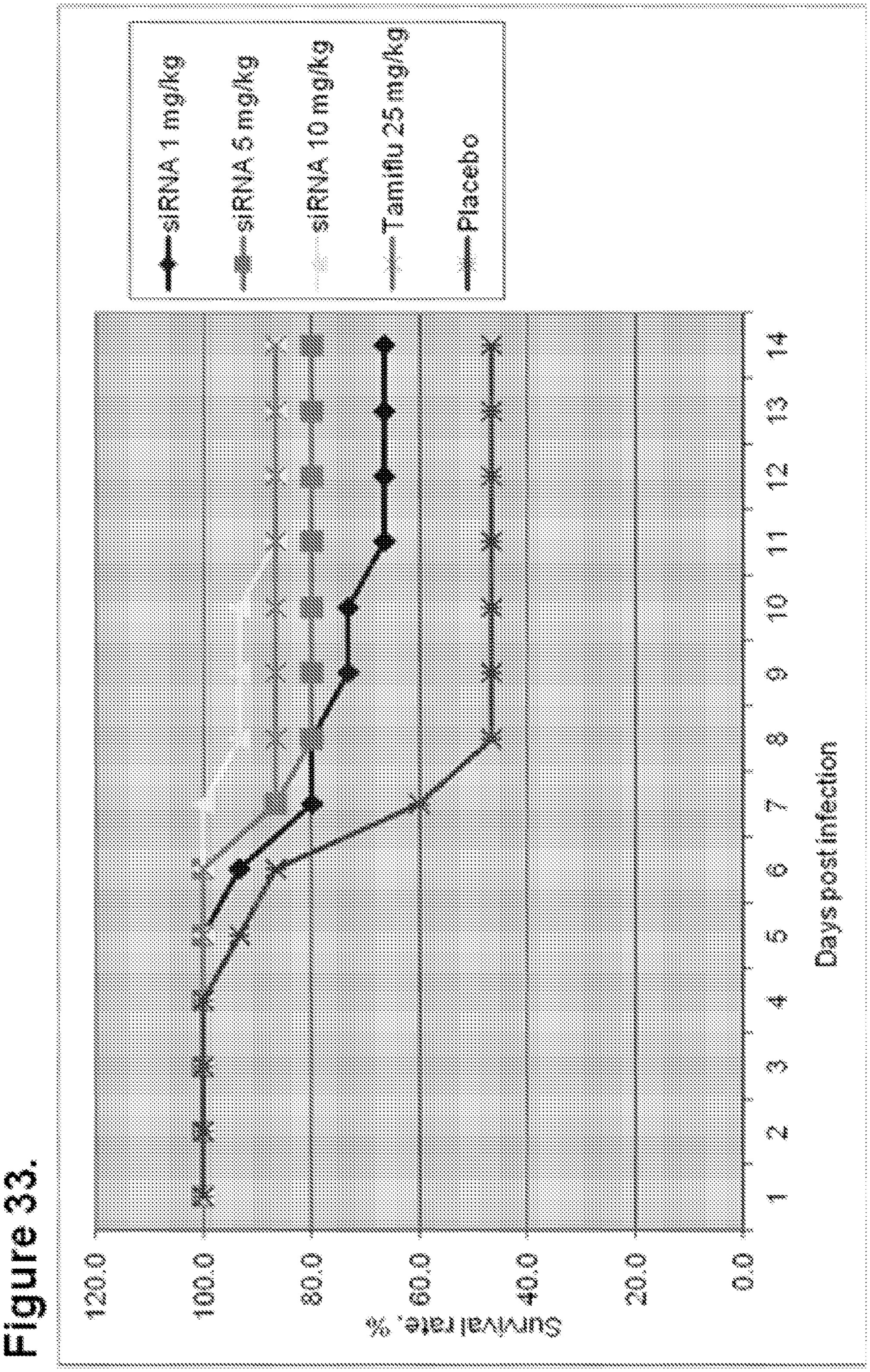
FIG. 33. Dose Dependence of the combined #89/#103 siRNA treatment. Using mice challenged by influenza virus (H1N1) to evaluate the therapeutic benefit of the combined siRNA pair at three different dosages, in comparison with the gold standard (Tamiflu) therapeutic efficacy.
Figure 34:
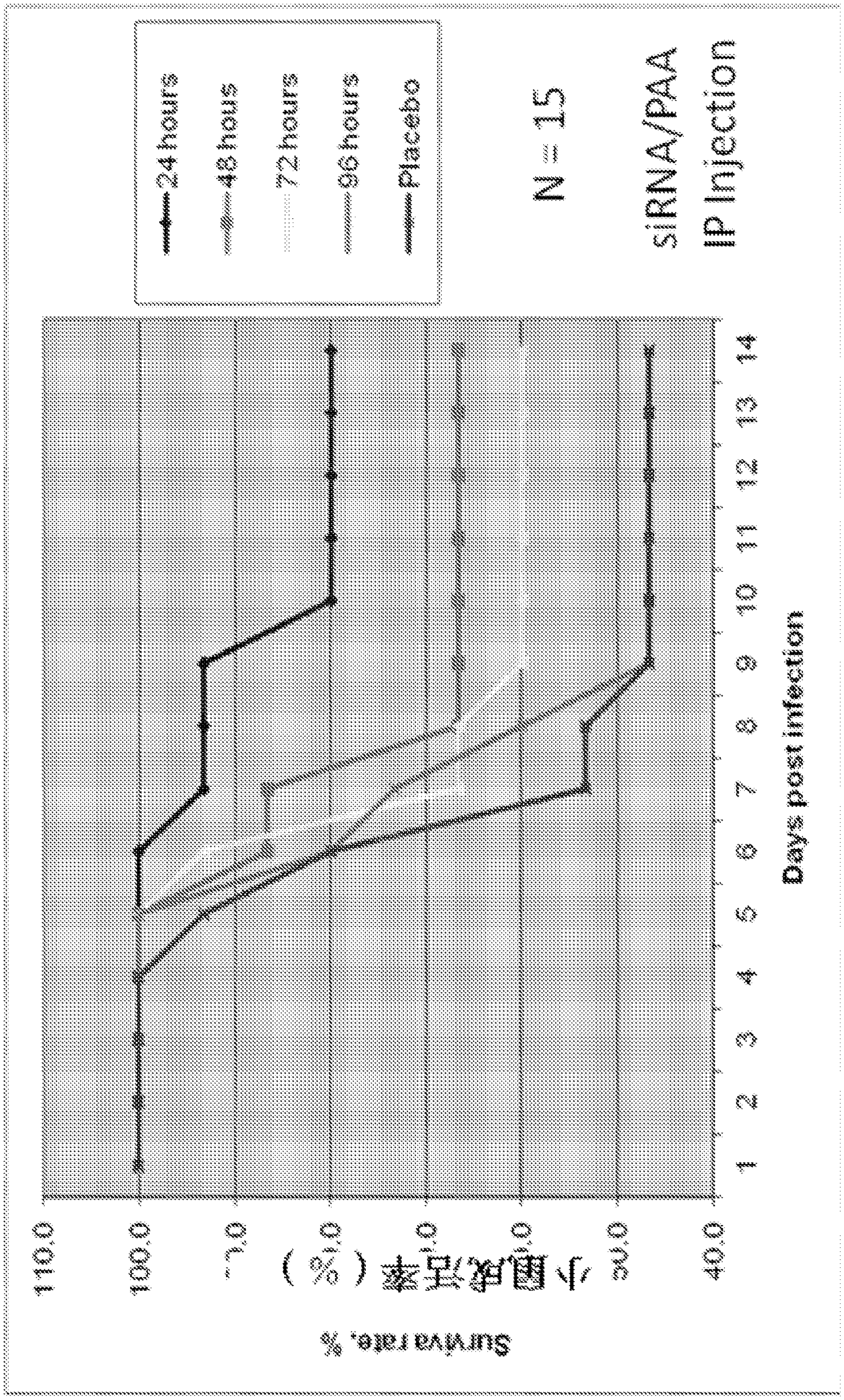
FIG. 34. The Critical Time Point for siRNA Therapeutic Intervention. The mice challenged by Influenza Virus A/California/07/09 (H1N1)pdm09 were subjected to treatment with the combined #89/#103 siRNA pair, at 24, 48, 72 and 96 hours post viral challenge.

Example 14. Evaluate Antiviral Activities of Combined #891#103 siRNA Pair Using Mouse Model We tested the antiviral activity of combined #89/#103 siRNA pair packaged with PAA through I.P. administration of siRNAs against M2 And PA genes, we observed a dose-dependent inhibition of lethality in mice exposed to H1N1. The PAA packaged siRNAs were administered through I.P. injection to mice exposed to a mouse-adpated H1N1 strain (A/California/07/09 (H1N1)pdm09). In placebo treated animals~50% died 8 days after exposure. Administration of 10 mg/Kg of the combination siRNAs 24 h post exposure to the virus resulted in >80% survival after 11 days and this value was equivalent to the effect seen using 25 mg/Kg of Tamiflu (FIG. 32). To further evaluate the best timing for therapeutic intervention, we also treated mice exposed to the lethal dose of mouse-adpated H1N1 strain (A/California/07/09 (H1N1)pdm09) at 24, 48, 72 and 96 hours post viral challenge. The result clearly indicated that 24 hours was the time with the most efficacious effect (FIG. 33).

Example 15. The Active siRNA Duplexes Against H1N1 are also Efficacious to H7N9

Between late March and early May of 2013, a newly identified form of influenza, H7N9, was responsible for an outbreak in China that produced respiratory disease in patients with with more than 30% mortality. We therefore quickly screened the siRNA duplexes that have been tested active against H1N1 using H7N9 challenged MDCK cell culture. The bioinformatics search identified 100% homology among 7 different strains of H7N9 reported in China (Table 6).

TABLE 6

Selected siRNA sequences also share homology with recently reported H7N9 viral genes. The three siRNA sequences have been validated for their potent anti-influenza activities in vitro and in vivo using H1N1 challenged MDCK cell culture model. Green color highlights indicated 100% homology between the selected siRNA sequences against H1N1and H7N9 viral RNA.

| | | Does siRNA match? | | |
|---|---|---|---|---|
| H7N9 coverage Strain | Genome ID | MP siRNA #89 | PA siRNA #103 | NP siRNA #105 |
| A/blue winged teal/Ohio/566/2006 | UNK22171 | YES | NO | YES |
| A/environment/Maryland/566/2006 | UNK20066 | YES | NO | YES |
| A/turkey/Minnesota/1/1988 | AV12223 | YES | NO | YES |
| A/goose/Czech Republic/1848/2009 | AV34330 | YES | YES | YES |
| A/northern shoverl/Mississippi/110S145/2011 | CY133652.1 | YES | YES | YES |
| China, A/Shanghai/1/2013, | EPI_ISL_138737 | No | YES | YES |
| China, A/Shanghai/2/2013, | PI_ISL_138738 | No | YES | YES |
| China, A/Anhui/1/2013, | EPI_ISL_138739 | No | YES | YES |
| China, A/Hangzhou/1/2013, | EPI_ISL_138977 | No | YES | YES |
| China, A/Chicken/2013 | EPI_ISL_138983 | No | YES | YES |
| China, A/Environment/2013 | EPI_ISL_138984 | No | YES | YES |
| China, \| A/Pigeon/2013 | EPI_ISL_138985 | No | YES | YES |

The siRNA therapeutics we used with PEG-PEI mediated intranasal instillation into the H5N1 viral challenged mice, using a regimen of 100 ug per dose, twice a day for two days, started 24 hours post viral challenge, exhibited 60% survival rate of treated mice, compared to the results of 40% for Zanamivir treatment, 0% for Ribavirin and other siRNA attempts.

Therefore, both siRNA #103 (specific to PA gene) and siRNA#105 (specific to NP gene) have homology to both H1N1 and H7N9 viral sequences. Where #105 has been validated with either H1N1 or H7N9 challenged MDCK cells resulted in potent anti-influenza activity with IC50<7 nM. We hypothesize that a combination of the siRNA #103/#105 pair will be very active against both H1N1 and H7N9.

REFERENCES

1. Balicer, R. D., Reznikovich, S., Berman, E., Pirak, M., Inbar, A., Pokamunski, S., and Grotto, I. 2007. Multifocal avian influenza (H5N1) outbreak. *Emerg Infect Dis* 13(10): 1601-1603.
2. Birmingham, A., Anderson, E., Sullivan, K., Reynolds, A., Boese, Q., Leake, D., Karpilow, J. and Khvorova, A. (2007) A protocol for designing siRNAs with high functionality and specificity. *Nat Protoc,* 2, 2068-2078.
3. Bitko, V., Musiyenko, A., Shulyayeva, O., and Batik, S. 2005 Inhibition of respiratory viruses by nasally administered siRNA. *Nat Med* 11(1): 50-55.
4. Boden, D., Pusch, O., Lee, F., Tucker, L., and Ramratnam, B. 2003. Human immunodeficiency virus type 1 escape from RNA interference. *J Virol* 77(21): 11531-11535.
5. Cheng, C., Yao, L., Chen, A., Jia, R., Huan, L., Guo, J., Bo, H., Shu, Y., and Zhang, Z. 2009 Inhibitory effect of small interfering RNA specific for a novel candidate target in PB1 gene of influenza A virus. *J Drug Target* 17(2): 133-139.
6. Cohen, L. and Castro, M. 2003. The role of viral respiratory infections in the pathogenesis and exacerbation of asthma. *Semin Respir Infect* 18(1): 3-8.
7. Colman, P. M. 2009. New antivirals and drug resistance. *Annu Rev Biochem* 78: 95-118.
8. Das, A. T., Brummelkamp, T. R., Westerhout, E. M., Vink, M., Madiredjo, M., Bernards, R., and Berkhout, B. 2004. Human immunodeficiency virus type 1 escapes from RNA interference-mediated inhibition. *J Virol* 78(5): 2601-2605.
9. Dawood, F. S., Jain, S., Finelli, L. et al. 2009. Emergence of a novel swine-origin influenza A (H1N1) virus in humans. N Engl J Med 360(25): 2605-15
10. Elbashir, S. M., Lendeckel, W., and Tuschl, T. 2001. RNA interference is mediated by 21- and 22-nucleotide RNAs. *Genes Dev* 15(2): 188-200.
11. Fedorov, Y., Anderson, E. M., Birmingham, A., Reynolds, A., Karpilow, J., Robinson, K., Leake, D., Marshall, W. S. and Khvorova, A. (2006) Off-target effects by siRNA can induce toxic phenotype. *Rna,* 12, 1188-1196.
12. Fiegel, J., Ehrhardt, C., Schaefer, U. F., Lehr, C. M., and Hanes, J. 2003. Large porous particle impingement on lung epithelial cell monolayers—toward improved particle characterization in the lung. *Pharm Res* 20(5): 788-796.
13. Filipowicz, W. 2005. RNAi: the nuts and bolts of the RISC machine. *Cell* 122(1): 17-20.
14. Ge, Q., Filip, L., Bai, A., Nguyen, T., Eisen, H. N., and Chen, J. 2004 Inhibition of influenza virus production in virus-infected mice by RNA interference. *Proc Natl Acad Sci USA* 101(23): 8676-8681.
15. Ge, Q., McManus, M. T., Nguyen, T., Shen, C. H., Sharp, P. A., Eisen, H. N., and Chen, J. 2003. RNA interference of influenza virus production by directly targeting mRNA for degradation and indirectly inhibiting all viral RNA transcription. *Proc Natl Acad Sci USA* 100(5): 2718-2723.
16. Gitlin, L., Stone, J. K., and Andino, R. 2005. Poliovirus escape from RNA interference: short interfering RNA-target recognition and implications for therapeutic approaches. *J Virol* 79(2): 1027-1035.
17. Griesenbach, U., Kitson, C., Escudero Garcia, S., Farley, R., Singh, C., Somerton, L., Painter, H., Smith, R. L., Gill, D. R., Hyde, S. C. et al. 2006. Inefficient cationic lipid-mediated siRNA and antisense oligonucleotide transfer to airway epithelial cells in vivo. *Respir Res* 7: 26.
18. Griffiths, P. D. 2009. A perspective on antiviral resistance. *J Clin Virol.*
19. Grimm, D., Pandey, K., Nakai, H., Storm, T. A., and Kay, M. A. 2006. Liver transduction with recombinant adeno-associated virus is primarily restricted by capsid serotype not vector genotype. *J Virol* 80(1): 426-439.
20. Harper, S. A., Fukuda, K., Uyeki, T. M., Cox, N. J., and Bridges, C. B. 2004. Prevention and control of influenza: recommendations of the Advisory Committee on Immunization Practices (ACIP). *MMWR Recomm Rep* 53(RR-6): 1-40.
21. Hayden, F. G. and Hay, A. J. 1992. Emergence and transmission of influenza A viruses resistant to amantadine and rimantadine. *Curr Top Microbiol Immunol* 176: 119-130.
22. Howard, K. A., Rahbek, U. L., Liu, X., Damgaard, C. K., Glud, S. Z., Andersen, M. O., Hovgaard, M. B., Schmitz, A., Nyengaard, J. R., Besenbacher, F. et al. 2006. RNA interference in vitro and in vivo using a novel chitosan/siRNA nanoparticle system. *Mol Ther* 14(4): 476-484.
23. Jackson, A. L., Bartz, S. R., Schelter, J., Kobayashi, S. V., Burchard, J., Mao, M., Li, B., Cavet, G. and Linsley, P. S. (2003) Expression profiling reveals off-target gene regulation by RNAi. *Nat Biotechnol,* 21, 635-637.
24. Jackson, A. L., Burchard, J., Leake, D., Reynolds, A., Schelter, J., Guo, J., Johnson, J. M., Lim, L., Karpilow, J., Nichols, K. et al. (2006) Position-specific chemical modification of siRNAs reduces "off-target" transcript silencing. *Rna,* 12, 1197-1205.
25. Jinek, M. and Doudna, J. A. 2009. A three-dimensional view of the molecular machinery of RNA interference. *Nature* 457(7228): 405-412.
26. Judge, A. and MacLachlan, I. (2008) Overcoming the innate immune response to small interfering RNA. *Hum Gene Ther,* 19, 111-124.
27. Konishi, M., Wu, C. H., Kaito, M., Hayashi, K., Watanabe, S., Adachi, Y., and Wu, G. Y. 2006. siRNA-resistance in treated HCV replicon cells is correlated with the development of specific HCV mutations. *J Viral Hepat* 13(11): 756-761.
28. Kunisaki, K. M. and Janoff, E. N. 2009. Influenza in immunosuppressed populations: a review of infection frequency, morbidity, mortality, and vaccine responses. *Lancet Infect Dis* 9(8): 493-504.
29. Lackenby, A., Hungnes, O., Dudman, S. G., Meijer, A., Paget, W. J., Hay, A. J., and Zambon, M. C. 2008a. Emergence of resistance to oseltamivir among influenza A(H1N1) viruses in Europe. *Euro Surveill* 13(5).
30. Lackenby, A., Thompson, C. I., and Democratis, J. 2008b. The potential impact of neuraminidase inhibitor resistant influenza. *Curr Opin Infect Dis* 21(6): 626-638.
31. Lee, Y. S., Nakahara, K., Pham, J. W., Kim, K., He, Z., Sontheimer, E. J., and Carthew, R. W. 2004. Distinct roles for *Drosophila* Dicer-1 and Dicer-2 in the siRNA/miRNA silencing pathways. *Cell* 117(1): 69-81.
32. Leonard, J. N., Shah, P. S., Burnett, J. C., and Schaffer, D. V. 2008. HIV evades RNA interference directed at TAR by an indirect compensatory mechanism. *Cell Host Microbe* 4(5): 484-494.
33. Li, B. J., Tang, Q., Cheng, D., Qin, C., Xie, F. Y., Wei, Q., Xu, J., Liu, Y., Zheng, B. J., Woodle, M. C. et al. 2005. Using siRNA in prophylactic and therapeutic regimens against SARS coronavirus in Rhesus macaque. *Nat Med* 11(9): 944-951.
34. Li S, Tan Y, Viroonchatapan E, Pitt B R, Huang L. 2000. Targeted gene delivery to pulmonary endothelium by anti-PECAM antibody. *Am J Physiol Lung Cell Mol Physiol* 278: L504-11.
35. Li S, Wu S P, Whitmore M, Loeffert E J, Wang L, Watkins S C, Pitt B R, Huang L. 1999. Effect of immune response on gene transfer to the lung via systemic administration of cationic lipidic vectors. Am J Physiol 276: L796-804.
36. Lin, X., Ruan, X., Anderson, M. G., McDowell, J. A., Kroeger, P. E., Fesik, S. W. and Shen, Y. (2005) siRNA-mediated off-target gene silencing triggered by a 7 nt complementation. *Nucleic Acids Res,* 33, 4527-4535.
37. Lomas-Neira, J. L., Chung, C. S., Wesche, D. E., Perl, M., and Ayala, A. 2005. In vivo gene silencing (with siRNA) of pulmonary expression of MIP-2 versus KC results in divergent effects on hemorrhage-induced, neutrophil-mediated septic acute lung injury. *J Leukoc Biol* 77(6): 846-853.
38. Ma Z, Zhang J, Alber S, Dileo J, Negishi Y, Stolz D, Watkins S, Huang L, Pitt B, Li S. 2002. Lipidmediated delivery of oligonucleotide to pulmonary endothelium. *Am J Respir Cell Mol Biol* 27: 151-159.
39. Mam Z., Li, J., He, F., Wilson, A., Pitt, B., Li, S. 2005. Cationic lipids enhance siRNA-mediated interferon response in mice. Biochem Biophys Res Commun 330(3): 755-9.
40. Massaro, D., Massaro, G. D., and Clerch, L. B. 2004. Noninvasive delivery of small inhibitory RNA and other reagents to pulmonary alveoli in mice. *Am J Physiol Lung Cell Mol Physiol* 287(5): L1066-1070.
41. McSwiggen, J. A. and Seth, S. 2008. A potential treatment for pandemic influenza using siRNAs targeting conserved regions of influenza A. *Expert Opin Biol Ther* 8(3): 299-313.
42. Michaelis, M., Doerr, H. W., and Cinatl, J., Jr. 2009. Novel swine-origin influenza A virus in humans: another pandemic knocking at the door. *Med Microbiol Immunol* 198(3): 175-183.
43. Parvin, J. D., Moscona, A., Pan, W. T., Leider, J. M., and Palese, P. 1986. Measurement of the mutation rates of animal viruses: influenza A virus and poliovirus type 1. *J Virol* 59(2): 377-383.
44. Perl, M., Chung, C. S., Lomas-Neira, J., Rachel, T. M., Biffl, W. L., Cioffi, W. G., and Ayala, A. 2005. Silencing of Fas, but not caspase-8, in lung epithelial cells ameliorates pulmonary apoptosis, inflammation, and neutrophil influx after hemorrhagic shock and sepsis. *Am J Pathol* 167(6): 1545-1559.
45. Pham, J. W., Pellino, J. L., Lee, Y. S., Carthew, R. W., and Sontheimer, E. J. 2004. A Dicer-2-dependent 80 s complex cleaves targeted mRNAs during RNAi in *Drosophila. Cell* 117(1): 83-94.
46. Robbins, M., Judge, A., Ambegia, E., Choi, C., Yaworski, E., Palmer, L., McClintock, K., and MacLachlan, I. 2008. Misinterpreting the therapeutic effects of small interfering RNA caused by immune stimulation. *Hum Gene Ther* 19(10): 991-999.
47. Schirmer, P. and Holodniy, M. 2009. Oseltamivir for treatment and prophylaxis of influenza infection. *Expert Opin Drug Saf* 8(3): 357-371.
48. Siomi, H. and Siomi, M. C. 2009. On the road to reading the RNA-interference code. *Nature* 457(7228): 396-404.
49. Sui, H. Y., Zhao, G. Y., Huang, J. D., Jin, D. Y., Yuen, K. Y., and Zheng, B. J. 2009. Small interfering RNA targeting m2 gene induces effective and long term inhibition of influenza A virus replication. *PLoS One* 4(5): e5671.

50. Tomari, Y., Du, T., Haley, B., Schwarz, D. S., Bennett, R., Cook, H. A., Koppetsch, B. S., Theurkauf, W. E., and Zamore, P. D. 2004a. RISC assembly defects in the *Drosophila* RNAi mutant armitage. *Cell* 116(6): 831-841.
51. Tomari, Y., Matranga, C., Haley, B., Martinez, N., and Zamore, P. D. 2004b. A protein sensor for siRNA asymmetry. *Science* 306(5700): 1377-1380.
52. Tompkins, S. M., Lo, C. Y., Tumpey, T. M., and Epstein, S. L. 2004. Protection against lethal influenza virus challenge by RNA interference in vivo. *Proc Natl Acad Sci USA* 101(23): 8682-8686.
53. Torchilin V P, Levchenko T S, Lukyanov A N, Khaw B A, Klibanov A L, Rammohan R, Samokhin G P, Whiteman K R. 2001. p-Nitrophenylcarbonyl-PEG-PE-liposomes: fast and simple attachment of specific ligands, including monoclonal antibodies, to distal ends of PEG chains via pnitrophenylcarbonyl groups. *Biochim Biophys Acta* 1511: 397-411.
54. Uyeki, T. M. 2009. Human infection with highly pathogenic avian influenza A (H5N1) virus: review of clinical issues. *Clin Infect Dis* 49(2): 279-290.
55. von Eije, K. J., ter Brake, O., and Berkhout, B. 2008. Human immunodeficiency virus type 1 escape is restricted when conserved genome sequences are targeted by RNA interference. *J Virol* 82(6): 2895-2903.
56. Webster, R. G., Bean, W. J., Gorman, O. T., Chambers, T. M., and Kawaoka, Y. 1992. Evolution and ecology of influenza A viruses. *Microbiol Rev* 56(1): 152-179.
57. Westerhout, E. M., Ooms, M., Vink, M., Das, A. T., and Berkhout, B. 2005. HIV-1 can escape from RNA interference by evolving an alternative structure in its RNA genome. *Nucleic Acids Res* 33(2): 796-804.
58. Wilson, J. A. and Richardson, C. D. 2005. Hepatitis C virus replicons escape RNA interference induced by a short interfering RNA directed against the NS5b coding region. *J Virol* 79(11): 7050-7058.
59. Wu, H. L., Huang, L. R., Huang, C. C., Lai, H. L., Liu, C. J., Huang, Y. T., Hsu, Y. W., Lu, C. Y., Chen, D. S., and Chen, P. J. 2005. RNA interference-mediated control of hepatitis B virus and emergence of resistant mutant. *Gastroenterology* 128(3): 708-716.
60. Xu, C. X., Jere, D., Jin, H., Chang, S. H., Chung, Y. S., Shin, J. Y., Kim, J. E., Park, S. J., Lee, Y. H., Chae, C. H. et al. 2008. Poly(ester amine)-mediated, aerosol-delivered Aktl small interfering RNA suppresses lung tumorigenesis. *Am J Respir Crit Care Med* 178(1): 60-73.
61. Zhang, X., Shan, P., Jiang, D., Noble, P. W., Abraham, N. G., Kappas, A., and Lee, P. J. 2004. Small interfering RNA targeting heme oxygenase-1 enhances ischemia-reperfusion-induced lung apoptosis. *J Biol Chem* 279(11): 10677-10684.
62. Zhang, X., Shan, P., Jiang, G., Zhang, S. S., Otterbein, L. E., Fu, X. Y., and Lee, P. J. 2006. Endothelial STAT3 is essential for the protective effects of HO-1 in oxidant-induced lung injury. *Faseb J* 20(12): 2156-2158.
63. Zhou, H., Jin, M., Yu, Z., Xu, X., Peng, Y., Wu, H., Liu, J., Liu, H., Cao, S., and Chen, H. 2007. Effective small interfering RNAs targeting matrix and nucleocapsid protein gene inhibit influenza A virus replication in cells and mice. *Antiviral Res* 76(2): 186-193.
64. Zhou, K., He, H., Wu, Y., and Duan, M. 2008. RNA interference of avian influenza virus H5N1 by inhibiting viral mRNA with siRNA expression plasmids. *J Biotechnol* 135(2): 140-144.

All publications, including issued patents and published patent applications, and all database entries identified by url addresses or accession numbers are incorporated herein by reference in their entirety.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A pharmaceutical composition comprising at least two different siRNA molecules and a pharmaceutically acceptable polymeric carrier, wherein one of the at least two different siRNA molecules targets a conserved region of an influenza A virus gene and is selected from the group consisting of molecules 89 (SEQ ID NOS 14 and 11) and 91 (SEQ ID NOS 61 and 68) as shown in Table 5 and the other of the at least two different siRNA molecules targets a conserved region of a different influenza A virus gene and is selected from the group consisting of molecules 93 (SEQ ID NOS 62 and 69), 95 (SEQ ID NOS 63 and 70), 97 (SEQ ID NOS 64 and 71), 99 (SEQ ID NOS 65 and 72), 101 (SEQ ID NOS 66 and 73), 103 (SEQ ID NOS 12 and 13), and 105 (SEQ ID NOS 67 and 74) as shown in Table 5.

2. The composition of claim 1, wherein the at least two different siRNA molecules comprise molecules 89 (SEQ ID NOS 14 and 11) and 103 (SEQ ID NOS 12 and 13) or molecules 91 (SEQ ID NOS 61 and 68) and 105 (SEQ ID NOS 67 and 74) as shown in Table 5.

3. The composition of claim 2, wherein the composition comprises a nanoparticle.

4. The composition of claim 3, wherein the genes are in the same virus strain.

5. The composition of claim 3, wherein the genes are in two different virus strains.

6. The composition of claim 3, wherein at least one of the siRNA molecules includes an immune-stimulating motif.

7. The composition of claim 3, wherein at least one of the siRNA molecules includes a potency-enhancing motif.

8. The composition of claim 3, wherein the sequences comprising the siRNA molecules have no homology to a mammalian gene.

9. The composition of claim 3, wherein the polymeric carrier comprises a Histidine-Lysine co-polymer.

10. The composition of claim 1, wherein the genes are in the same virus strain.

11. The composition of claim 1, wherein the genes are in two different virus strains.

12. The composition of claim 1, wherein the composition comprises a nanoparticle.

13. The composition of claim 12, wherein the polymeric carrier comprises a Histidine-Lysine co-polymer.

14. A method of treating a mammal with an influenza A infection comprising administering to the mammal a pharmaceutically effective amount of the composition of claim 1.

15. The method of claim 14, wherein the mammal is a human.

16. A prophylactic method of reducing the severity of an influenza A infection in a mammal comprising administering to the mammal a pharmaceutically effective amount of the composition of claim 1.

17. The method of claim 16, wherein the mammal is a human.

18. A method of treating a mammal with an influenza A infection comprising administering to the mammal a pharmaceutically effective amount of the composition of claim 3.

19. The method of claim 18, wherein the mammal is a human.

20. The method of claim 19, wherein the composition is administered via the human's airway.

21. A prophylactic method of reducing the severity of an influenza A infection in a mammal comprising administering to the mammal a pharmaceutically effective amount of the composition of claim 3.

22. The method of claim 21, wherein the mammal is a human.

* * * * *